United States Patent [19]

Kubokawa et al.

[11] Patent Number: 5,035,231
[45] Date of Patent: Jul. 30, 1991

[54] ENDOSCOPE APPARATUS

[75] Inventors: Hiroaki Kubokawa; Takashi Tsukaya, both of Hachioji; Yasuhiro Ueda, Kokubunji; Yutaka Ohshima, Hachioji; Takeaki Nakamura, Hino; Hiroki Hibino; Shuichi Takayama, both of Hachioji; Tadao Hagino, Yokohama, all of Japan

[73] Assignee: Olympus Optical Co., Ltd., Tokyo, Japan

[21] Appl. No.: 186,332

[22] Filed: Apr. 25, 1988

[30] Foreign Application Priority Data

| Apr. 27, 1987 | [JP] | Japan | 62-104033 |
|---|---|---|---|
| Apr. 28, 1987 | [JP] | Japan | 62-105868 |
| Apr. 28, 1987 | [JP] | Japan | 62-105870 |
| Jul. 15, 1987 | [JP] | Japan | 62-176532 |
| Jul. 15, 1987 | [JP] | Japan | 62-176534 |
| Aug. 10, 1987 | [JP] | Japan | 62-199395 |
| Aug. 10, 1987 | [JP] | Japan | 62-199396 |
| Aug. 11, 1987 | [JP] | Japan | 62-200292 |
| Aug. 18, 1987 | [JP] | Japan | 62-205539 |
| Aug. 18, 1987 | [JP] | Japan | 62-205540 |
| Aug. 18, 1987 | [JP] | Japan | 62-205541 |

[51] Int. Cl.⁵ .............................. A61B 1/00; A61B 5/05
[52] U.S. Cl. .................................. 128/6; 128/653 R; 128/4
[58] Field of Search .................. 128/6, 653, 4; 358/98

[56] References Cited

U.S. PATENT DOCUMENTS

| 4,349,029 | 9/1982 | Mott | 604/96 |
|---|---|---|---|
| 4,433,692 | 2/1984 | Baba | 128/6 |
| 4,474,174 | 10/1984 | Petruzzi | 128/6 |
| 4,489,727 | 12/1984 | Matsuo et al. | 128/6 |
| 4,572,198 | 2/1986 | Codrington | 128/658 |
| 4,616,631 | 10/1986 | Takahashi | 128/6 |
| 4,643,186 | 2/1987 | Rosen et al. | 128/804 |
| 4,672,972 | 6/1987 | Berke | 128/653 |
| 4,681,093 | 7/1987 | Ono et al. | 128/6 |
| 4,737,142 | 4/1988 | Heckele | 128/6 |

FOREIGN PATENT DOCUMENTS 59-88140  5/1984  Japan.
62-500048 1/1987  Japan.

Primary Examiner—Edward M. Coven
Assistant Examiner—Jessica Harrison
Attorney, Agent, or Firm—Armstrong, Nikaido, Marmelstein, Kubovcik & Murray

[57] ABSTRACT

This endoscope apparatus adapted to meter NMR (nuclear magnetic resonance) is provided with an endoscope having a channel and an NMR metering probe insertable through the channel. The endoscope has an elongate insertable part having an observing window and illuminating window in the tip part, an observing system for observing an object to be imaged by receiving a light from the object entering through the observing window, an illuminating light output system emitting an illuminating light through the illuminating window and a hollow channel formed within the insertable part and opening in the tip part. Preferably, at least the tip side of the insertable part if formed of a non-ferromagnetic characteristic material. The NMR metering probe has a signal transmitting member insertable through the channel of the endoscope, connected at one end to the NMR metering apparatus and able to transmit high frequency signals and a loop-like antenna part connected to the other end of the signal transmitting member and projected out of the opening of the channel.

26 Claims, 37 Drawing Sheets

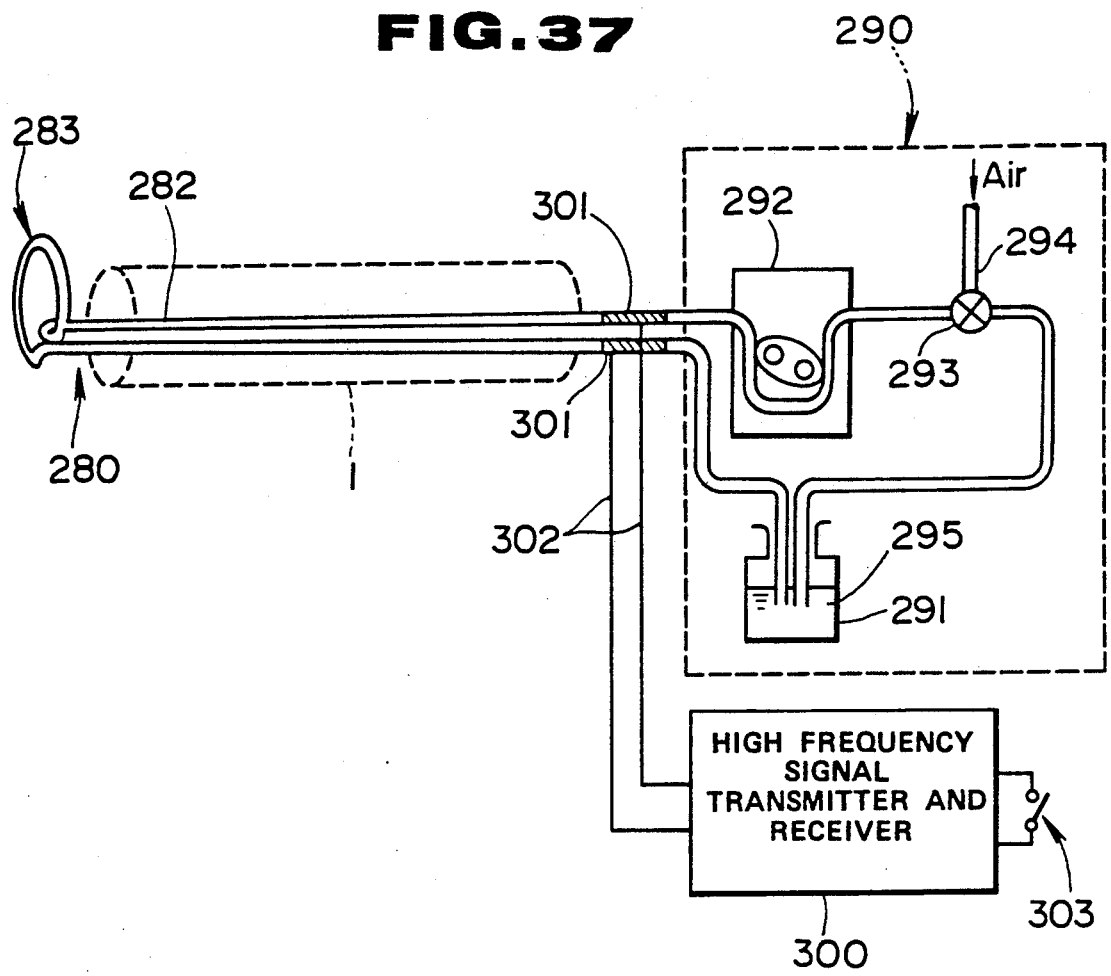
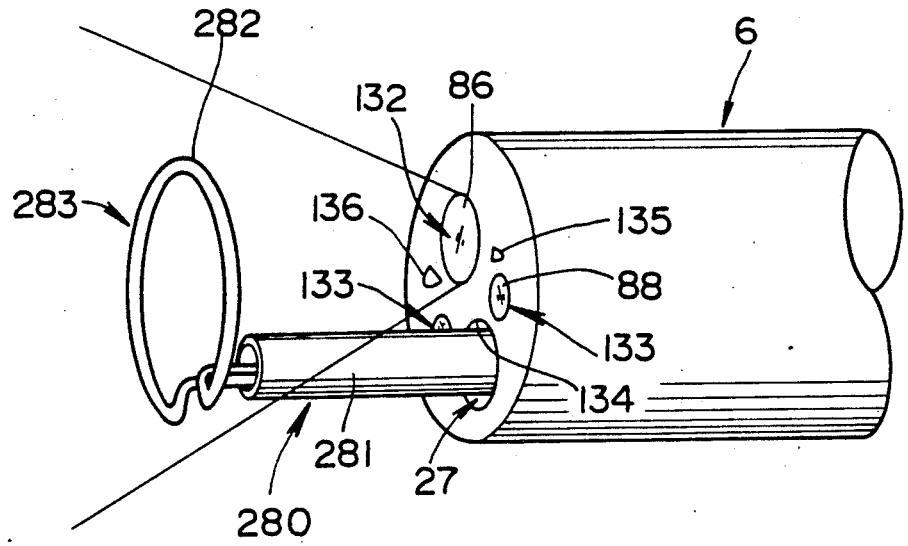

NMR METERING APPARATUS

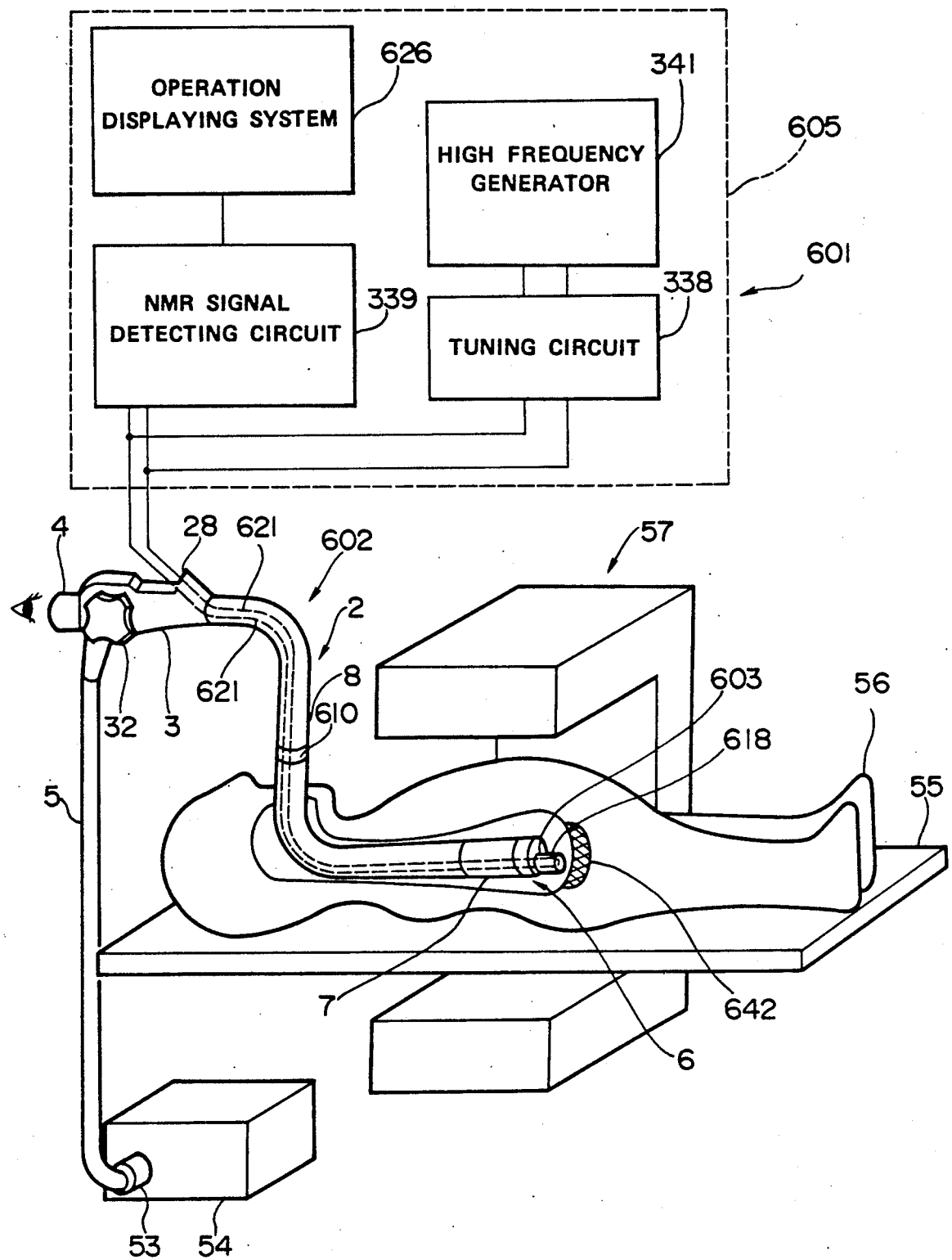

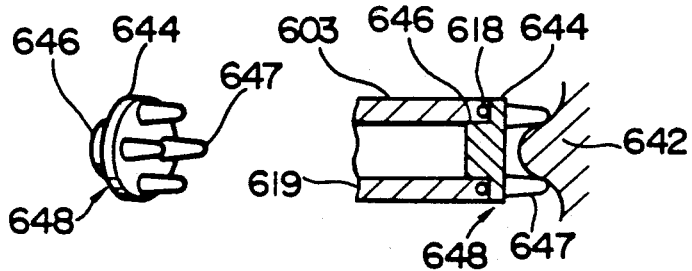
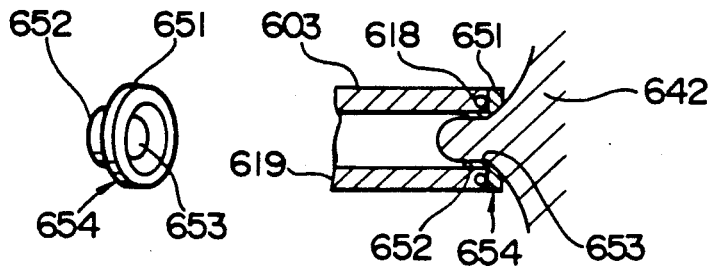
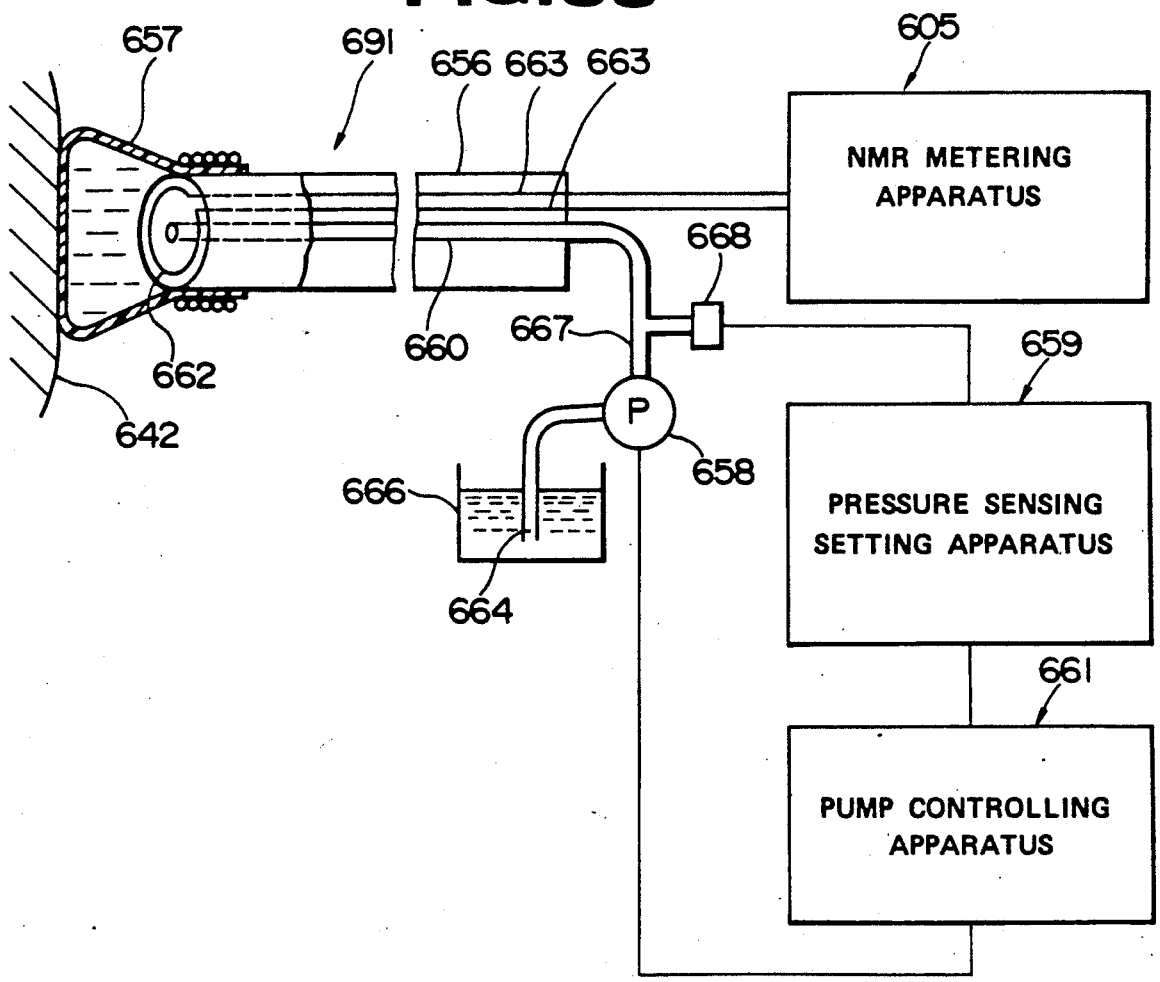

ENDOSCOPE APPARATUS

BACKGROUND OF THE INVENTION

1. Field of the Invention

This invention relates to an endoscope apparatus adapted to meter NMR.

2. Related Art Statement

Conventionally, in detecting and diagnosing a cuticle cancer or the like generated on the inner surface of a digestive organ of a human body or particularly in the upper layer part of a stomach wall, there has been a general method wherein the generating position is detected with an endoscope or X-ray photographing and the living body tissue of such position is collected and is diagnosed to be bad or not. However, in such conventional method, there have been problems that the sample collecting position is in a range so comparatively wide that the diagnosis can not be immediately made, that the toil of collecting the living body tissue is very large and that the human body is damaged.

On the other hand, against it, recently, there has come to be developed a non-attacking human body diagnosing method utilizing a nuclear magnetic resonance (abbreviated as NMR hereinafter) phenomenon. For example, in an NMR imaging apparatus utilizing the above mentioned NMR phenomenon, a human body is placed in a magnetic field, a high frequency (magnetic field) of a predetermined frequency is given to the human body, a nucleus having a spin within the human body is excited and an NMR signal of a predetermined frequency from this excited nucleus is sensed and is processed with a computer to obtain a sectioned image. The sectioned image obtained by this NMR imaging apparatus is very useful for diagnosing a cancer or the like. That is to say, generally, the NMR signals obtained from a cancer cell and normal cell are known to be different in the relieving time. The diagnosis of whether it is a cancer or not is made possible by measuring this relieving time.

However, in the above mentioned NMR imaging apparatus, in order to obtain a sectioned image, enormous NMR signals must be processed, a high speed large capacity computer is required and the entire apparatus becomes large and expensive.

Conventionally, at the time of the endoscope observation, in case a visually abnormal part is discovered whether this abnormal part is, for example, bad or not will be desired to be judged to some extent. However, for such above mentioned NMR imaging apparatus is expensive and large and that further it is difficult to make the part recognized to be visually abnormal and the sectioned image correspond to each other.

In order to cope with it, as shown, for example, in the gazette of a Japanese patent application laid open No. 88140/1984, there is suggested an NMR endoscope wherein, in the tip part of an endoscope insertable part, a high frequency magnetic field is formed and a high frequency coil (antenna) detecting NMR signals is provided. According to this NMR endoscope, when the above mentioned antenna is pressed against an abnormal position and the NMR signal of the abnormal position is detected, the physiological variation of this abnormal position, for example, whether it is a cancer or not can be detected and diagnosed.

Now, in the conventional MNR endoscope, the antenna is contained within the endoscope tip part body. However, as the above mentioned antenna is comparatively large and the above mentioned tip part is required to be fine in the diameter, it has been difficult to incorporate the antenna within the tip part without making the tip part large. Therefore, the above mentioned antenna has not been able to be easily led into a body.

A catheter or endoscope provided in the tip part with a coil is disclosed in the gazette of a Japanese patent application laid open No. 500048/1987 (international laid open No. W086/01093). However, in case only the catheter provided with the coil is led into a body, it will be difficult to confirm the NMR metering position. In case the coil is incorporated in the tip part of the endoscope, the tip part will become large as described above.

Generally, a ferromagnetic field is required to meter NMR. Therefore, in the endoscope to be used to meter NMR, at least the insertable part is arranged in a ferromagnetic field.

In the conventional endoscope, most of the curvable tube forming the curvable part, wires for curving the curvable part, flex (spiral tube) and blade (net tube) have used an inartensitic stainless steel to be a ferromagnetic material. When the insertable part is formed of such ferromagnetic material, in case it is used within a ferromagnetic field, it will be influenced by the magnetic field, the operation of smoothly inserting the insertable part into the body will be obstructed and it will be difficult to lead it into the object position. Within the magnetic field for NMR, the insertable part reacts so strongly on this magnetic field as to have been difficult to use within a body cavity.

In an endoscope containing an antenna in the tip part, in case NMR is metered with the antenna pressed against a living body tissue, the region in which NMR is being metered has not been able to be confirmed. Also, the visual field has not been able to be secured with the above mentioned antenna pressed against the living body tissue.

In case a diseased part within a body cavity is to be NMR-metered through an endoscope, unless the antenna is pressed against an object position, for example, for several tens of seconds to several minutes, no accurate metering will be able to be made. However, in an endoscope containing an antenna in the tip part, it has been difficult to fix the above mentioned antenna in an object position.

Now, there is a case that an antenna is inserted into a body cavity through an endoscope to meter NMR from within the body and such NMR apparatus for observing an NMR image from without the body as an NMR imaging apparatus is used simultaneously to observe NMR from without the body. However, as the antenna to be inserted into the body cavity is conventionally made of a metal, when the NMR image from without the body is to be observed with this antenna as inserted within the body cavity, the magnetic field of the NMR apparatus for observing from without the body will be disturbed and no good picture image will be obtained. Therefore, in case the NMR image from without the body is to be observed, it will be necessary to pull out the endoscope and the operation will be complicated.

In the above mentioned antenna, it is desirable to make the detecting direction coincide with the direction of the high frequency magnetic field made by this antenna itself. However, in the conventional NMR endoscope, as the antenna is fixed to the tip part, it has been difficult to make the detecting direction coincide with the high frequency magnetic field.

OBJECT AND SUMMARY OF THE INVENTION

An object of the present invention is to provide an endoscope apparatus wherein an NMR metering antenna can be easily led into such cavity as a body cavity.

Another object of the present invention is to provide an endoscope which can be smoothly inserted into such cavity as a body cavity and is adapted to meter NMR.

Further another object of the present invention is to provide an endoscope apparatus whereby the region in which NMR is being metered can be easily confirmed.

Further another object of the present invention is to provide an endoscope apparatus whereby an NMR metering antenna can be easily fixed in an object position.

Further another object of the present invention is to provide an endoscope apparatus having no influence on an NMR apparatus for observing from without a body.

Further another object of the present invention is to provide an endoscope apparatus whereby the detecting direction can be easily made to coincide with the direction of the high frequency magnetic field generated by the NMR metering antenna.

The endoscope apparatus of the present invention is provided with an endoscope having a channel and an NMR metering probe insertable into the above mentioned channel. The above mentioned endoscope has an elongate insertable part having an observing window and illuminating window in the tip part, an observing means for observing an object by receiving a light from the object entering through the above mentioned observing window, an illuminating light output means emitting an illuminating light through the above mentioned illuminating window and a hollow channel formed through the above mentioned insertable part and opening in the above mentioned tip part. The above mentioned insertable part is formed at least on the tip side preferably of a non-ferromagnetic characteristic material. The above mentioned NMR metering probe has a signal transmitting member insertable through the channel of the above mentioned endoscope, connected at one end to an NMR metering apparatus and able to transmit high frequency signals and a loop-like antenna part connected to the other end of the above mentioned signal transmitting member and projected out of the opening of the above mentioned channel.

The other features and advantages of the present invention will become apparent enough with the following explanation.

BRIEF DESCRIPTION OF THE DRAWINGS

FIG. 1 is a perspective view showing an endoscope.

FIG. 2 is a sectioned view showing the tip side of an insertable part of the endoscope.

FIG. 3 is an explanatory view of an endoscope apparatus as being used.

FIG. 4 is a circuit diagram showing an NMR metering means.

FIG. 5 is a perspective view showing an endoscope.

FIG. 6 is a sectioned view showing the tip side of an insertable part of the endoscope.

FIG. 7(A) is an elevation of the tip part of an insertable part of an endoscope.

FIG. 7(B) is a longitudinally sectioned view of the tip part of the insertable part of the endoscope.

FIG. 8 is a side view of the tip part as an antenna is projected.

FIG. 10 is a perspective view of the tip part of an insertable part of an endoscope as an antenna is projected.

FIG. 11 is a perspective view of the tip part of the insertable part of the endoscope as the antenna is retracted.

FIG. 13 is a perspective view of the tip part of an insertable part of an endoscope as an antenna is projected.

FIG. 14 is a perspective view of the tip part of the insertable part of the endoscope as the antenna is retracted.

FIG. 15 is an elevation of FIG. 14.

FIG. 16 is an explanatory view showing a longitudinally sectioned view of the tip part of an insertable part of an endoscope.

FIG. 17 is a perspective view of the tip part of the insertable part of the endoscope.

FIG. 19 is a sectioned view showing the tip part of an NMR metering antenna apparatus as a balloon is contracted.

FIG. 20 is a sectioned view showing the tip part of the NMR metering antenna apparatus as the balloon is inflated.

FIG. 21 is an explanatory view showing an endoscope apparatus.

FIG. 22 is an explanatory view showing an NMR metering antenna as being used.

FIG. 23 is a perspective view showing the tip part of an NMR metering antenna apparatus as a balloon is contracted.

FIG. 24 is a perspective view showing the tip part of the NMR metering antenna apparatus as the balloon is inflated.

FIG. 25 is a perspective view showing the tip part of an NMR metering antenna apparatus as a balloon is contracted.

FIG. 26 is a perspective view showing the tip part of the NMR metering antenna apparatus as the balloon is inflated.

FIG. 27 is a perspective view showing the tip part of an NMR metering antenna apparatus.

FIG. 28 is a longitudinally sectioned view of FIG. 27.

FIG. 29 is an explanatory view showing an endoscope apparatus.

FIG. 30 is a side view showing the NMR metering antenna apparatus as being used.

FIG. 32 is an explanatory view showing a longitudinally sectioned view of the tip part of an insertable part of an endoscope.

FIG. 33 is a plan view of FIG. 7.

FIG. 34 is an explanatory view showing an endoscope apparatus as being used.

FIGS. 37 to 41 relate to the 16th embodiment of the present invention.

FIG. 37 is an explanatory view showing the formation of an NMR metering antenna apparatus.

FIG. 38 is an explanatory view showing an endoscope.

FIG. 39 is a perspective view showing the tip part of an insertable part of the endoscope.

FIG. 40 is an explanatory view showing the NMR metering antenna apparatus when used as an antenna.

FIG. 41 is an explanatory view showing the NMR metering antenna apparatus when not used a an antenna.

FIG. 43 is a longitudinally sectioned view of the tip part of an insertable part of an endoscope in the case of metering in the direction at right angles with the lengthwise direction of the insertable part.

FIG. 44 is a longitudinally sectioned view of the tip part of the insertable part of the endoscope in the case of metering in the lengthwise direction of the insertable part.

FIG. 45 is a circuit diagram showing an NMR metering means.

FIG. 46 is a perspective view showing an entire endoscope apparatus.

FIG. 47 is a longitudinally sectioned view showing the tip part of an insertable part of the endoscope.

FIG. 50 is an explanatory view showing the formation of a retained tube and NMR metering apparatus.

FIG. 51 is a perspective view showing an antenna.

FIGS. 53 to 55 relate to the 24th embodiment of the present invention.

FIG. 53 is a perspective view showing the tip part of an insertable part of an endoscope apparatus.

FIG. 54 is a sectioned view showing the tip part of an antenna apparatus.

FIG. 55 is an explanatory view of the endoscope apparatus as being used.

FIG. 56(A) is perspective view of a lid in a modification of the 24th embodiment of the present invention.

FIG. 56(B) is a sectioned view of the lid of FIG. 56(A) as being used.

FIG. 57(A) is a perspective view of a lid in another embodiment of the 24th embodiment.

FIG. 57(B) is a sectioned view showing the lid of FIG. 57(A) as being used.

FIG. 58 is an explanatory view showing the formation of an NMR metering antenna apparatus in the 25th embodiment of the present invention.

DETAILED DESCRIPTION OF THE PREFERRED EMBODIMENTS

Figure 1:
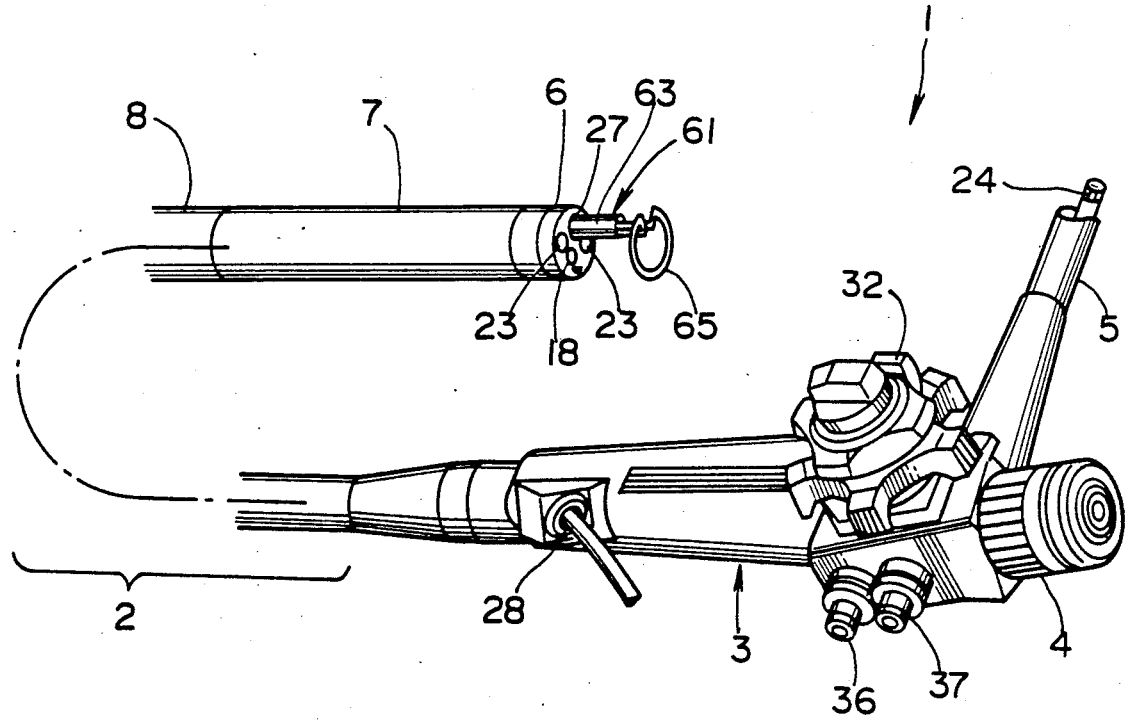
FIGS. 1 to 4 relate to the first embodiment of the present invention.
Figure 2:
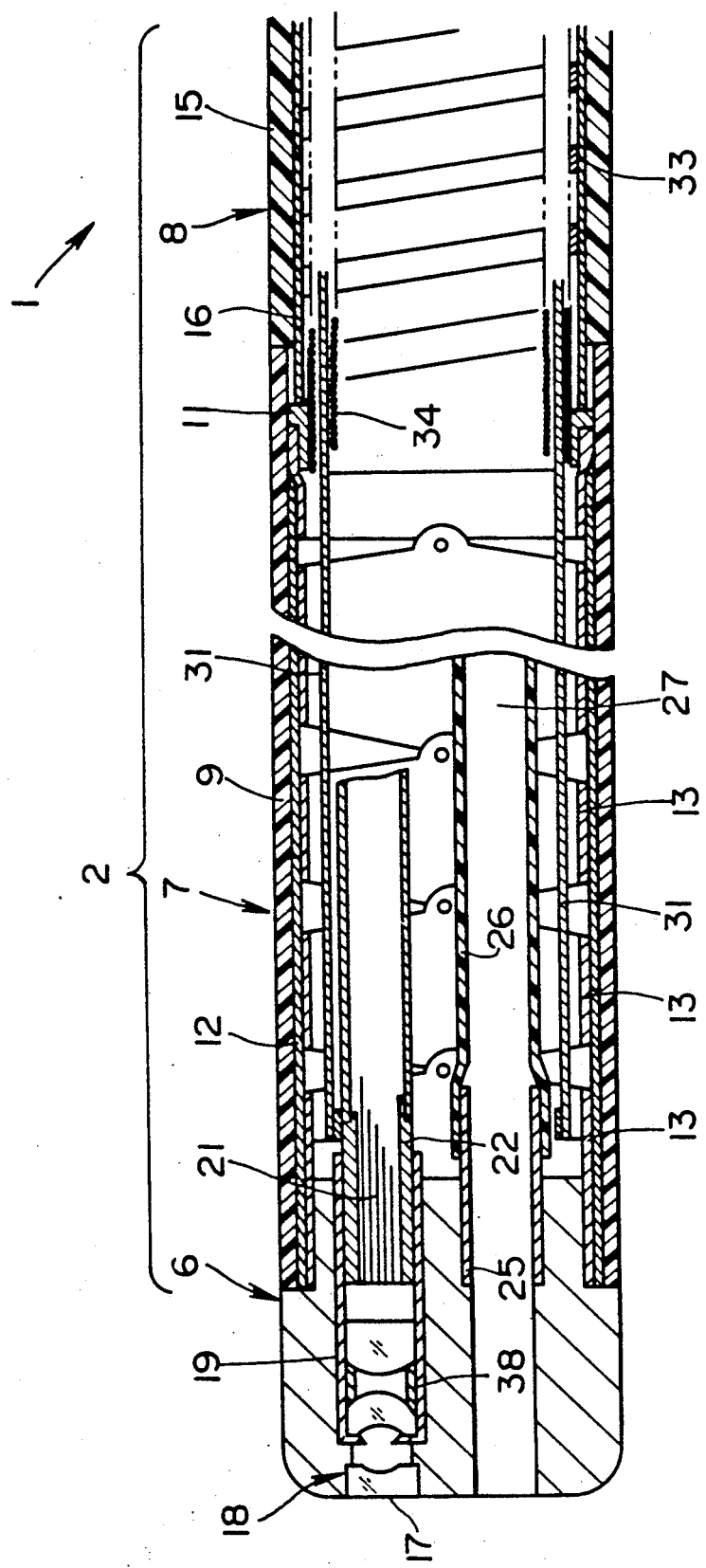

FIGS. 1 and 2 show the first embodiment of the present invention.

As shown in FIG. 1, a flexible endoscope 1 of the first embodiment is formed of an elongate flexible insertable part 2 insertable into a body cavity or the like, a thick operating part 3 provided on the rear end side of this insertable part 2 an eyepiece part 4 provided at the rear end of this operating part 3 and containing an eyepiece lens and an illuminating light transmitting light guide cable 5 provided to project on the side part of the above mentioned operating part.

The above mentioned insertable part 2 comprises a tip part 6 formed of a rigid member at the front end, a curvable part 7 formed on the rear side adjacent to this tip part 6 and a flexible part 8 on the rear side adjacent to this curvable part 7.

The above mentioned tip part 6 is formed of such feeble magnetic (or paramagnetic) material as, for example, an austenitic stainless steel. The outer periphery near the rear end of this tip part 6 is made steppedly smaller in the diameter to secure an outer coating 9 formed of such flexible material as a synthetic resin at the front end. This outer coating 9 covers the curvable part 7 and is fitted and secured at the rear end to the outer periphery of a front mouthpiece 11. A net tube 12 is internally fitted inside this outer coating 9. Substantially ring-like curvable tubes (curvable frames) 13 are connected inside this net tube (called also a blade) 12 so that the adjacent curvable tubes 13 may be rotatable with each other in the direction vertical to the paper surface and in the vertical direction within the paper surface. (In FIG. 2, for the brevity, only the case of the side of the direction vertical to the paper surface is shown.)

The above mentioned front mouthpiece 11, net tube 12 and respective curvable tubes 13 are formed of such feeble magnetic material as, for example, an austenitic stainless steel.

The flexible part 8 adjacent to the outer coating 9 covering the above mentioned curvable part 7 is coated with an outer coating 15 somewhat thicker than this outer coating and formed, for example, of a synthetic resin (needless to say a non-magnetic material). A net tube (blade) 16 formed of such feeble magnetic material as an austenitic stainless steel is internally fitted inside this outer coating 15.

A plurality of through holes parallel with the axial direction of the insertable part 2 are formed in the above mentioned tip part 6. One of the through holes is an observing window 17 in which an objective lens system 18 is fitted as shown in FIG. 2. A concave lens to be a front lens of this objective lens system 18 is secured directly to the through hole and the remaining parts of this objective lens system 18 are secured to the through hole through a lens frame 19. An image guide 21 formed of a fiber bundle is secured at the front end through a mouth piece 22 to the rear end side of this lens frame 19.

The above mentioned lens frame 19 and mouthpiece 22 are formed of such material as, for example, an austenitic stainless steel. An optical image formed on the front end surface of this image guide 21 by the objective lens system 18 is transmitted through this image guide 21 inserted through the insertable part 2 to the operating part 3 or eyepiece part 4 side on which the other end is arranged. The endoscope operator can observe with a naked eye the optical image transmitted through an eyepiece lens not illustrated by bringing the eye close to the rear end surface of the eyepiece part 4.

Figure 3:
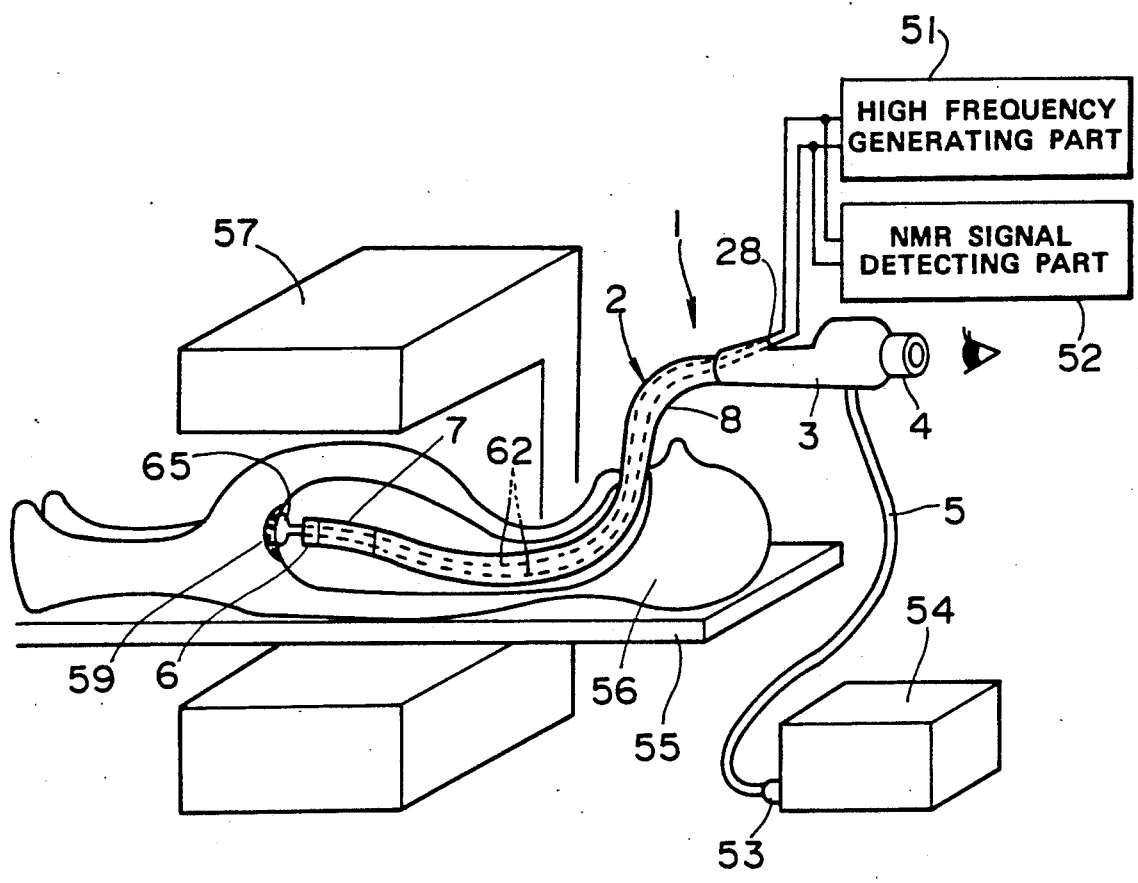

As shown in FIG. 2, two through holes are formed on both sides of and adjacently to the observing window 17 of the above mentioned tip part 6 and are illuminating windows closed with light distributing lenses 23. A light guide 24 is secured at the tip to the inner parts of the respective lenses 23 so that, when the light guide 24 inserted through the insertable part 2 and light guide cable 5 is connected at the base side end to a light source apparatus 54 through a connector 53 as shown in FIG. 3, the illuminating light of an illuminating lamp within this light source apparatus 54 will be able to be transmitted, will be emitted from the tip surface, will be expanded further by the light distributing lenses 23 and will be able to illuminate the object whose image is to be formed by the objective lens system 18.

In the above mentioned tip part 6, as shown in FIG. 2, a pipe 25 is secured inside the rear end side of a through hole formed adjacently to the through hole to be the observing window 17, a flexible tube 26 is further fitted at the front end to the outer periphery of the pipe 25 projecting from the rear end of the through hole and a treating tool channel (or forceps channel) 27 which can pass the treating tool through the tube 26 is formed. This channel 27 communicates on the base side with a channel leading inlet 28 formed on the side part of the operating part 3 as shown in FIG. 1. The above mentioned pipe 25 is formed, for example, of an austenitic stainless steel and the tube 26 is formed of a synthetic resin.

In the foremost curvable tube 13 among the curvable tubes 13 forming the curvable part 7 adjacent to the above mentioned tip part 6, the parts in the positions opposed through the center of the above mentioned tube, that is opposed at an angle of 180 degrees are partly incised and are bent inward and curving wires 31 are secured as by soldering to the bent parts. (By the way, in FIG. 2, a pair of wires 31 are inserted in the vertical direction within the paper surface in FIG. 2 but will be inserted also in the direction vertical to the paper surface.)

The respective wires 31 are formed for example, of an austenitic stainless steel.

The above mentioned pair of wires 31 are inserted through the insertable part 2 and are fitted to a rotary drum not illustrated within the operating part 3 so that, when the angle knob 32 fitted to the rotary shaft of this drum is rotated, one of the pair of wires 31 will be pulled, the other will be relaxed and the curvable tubes 13 rotatably connected in a longitudinal row will be able to be bent in the horizontal direction or vertical direction.

The curvable tube 13 of the last step among the above mentioned curvable tubes 13 is externally fitted to the smaller diameter part made steppedly smaller in the diameter of the substantially ring-like front mouthpiece 11 and is secured as by a bonding agent or soldering.

This front mouthpiece 11 is steppedly expanded in the diameter on the rear end side and the net tube 16 and the spiral tube (flex) 33 fitted inside the net tube 16 are fitted and secured in the front mouthpiece 11 on the rear end side. This spiral tube 33 is formed, for example, of an austenitic stainless steel.

The respective wires 31 inserted through inside the above mentioned curvable tubes 13 are inserted through the spiral tube 33 connected with the curvable tube 13 in the last step through the front mouthpiece 11.

The wires 31 passed through the c curvable tubes 13 are further inserted through the spiral tube 33 but are inserted on the rear side of the curvable tube 13 in the last step through the guide coils 34. By the way, the respective guide coils 34 are formed, for example, of an austenitic stainless steel.

By the way, an air and water feeding button 36 and sucking button 37 are provided on the side opposite the side out of which the light guide cable 5 is extend in the operating part 3 so that the air and water feeding and sucking operations may be made while the air and water feeding tube and sucking tube inserted through the insertable part 2 and light guide cable 5 are fitted at the rear ends to the light source apparatus and air and water may be fed to the outer surface side of the objective lens system through a nozzle provided on the tip forming part 6 to remove dust deposited on the outer surface and suck and discharge unnecessary things. By the way, a diaphragm is formed in the front part of the lens frame 19. The respective lenses fixed to the lens frame 19 are held at a predetermined spacing by a spacer 38 of a non-magnetic material.

By the way, the respective parts of the operating part 3 are formed also of a non-magnetic material.

In the case of metering NMR, as shown in FIG. 3, the above mentioned endoscope 1 is used as combined with an NMR apparatus 57 arranged to enclose the examines mounted on a bed 55. This NMR apparatus 57 is provided with such means of generating a static magnetic field as a permanent magnet, paraconductive magnet or superconductive magnet.

Now, in this embodiment, as shown in FIGS. 1 and 3, an NMR probe 61 for metering NMR is inserted through the above mentioned treating tool channel 27. In this NMR probe 61, as shown in FIG. 3, an NMR metering antenna (coil) 65 is connected to the tip of such signal cable 62 as a coaxial cable inserted through the above mentioned channel 27. The above mentioned antenna 65 is formed of a conductor, for example, of a circular cross-section so as to be like a one-wind loop of an outside diameter substantially equal to or somewhat smaller than the outside diameter of the above mentioned tip part. The above mentioned antenna 65 is lent at both ends to the inner peripheral side, that is, to the channel 27 side on the outer peripheral side of the above mentioned channel 27 and then rearward from the front position of the channel 27 and is connected at both ends to signal cables 62 inserted through the above mentioned channel 27. By the way, the antenna is coated on the outer surface with an insulating material. The above mentioned signal cables 62 are coated with a coating tube 63 and are led on the base sides out of the above mentioned leading inlet 28 and are connected to a high frequency generating part 51 and NMR signal detecting part 52. When the above mentioned signal cables 62 are moved in the axial direction, as shown in FIG. 1, the above mentioned antenna 65 will be able to be projected out of the tip part 6 and will be able to be retracted to be in close contact with the tip surface of the tip part 6.

As shown in FIG. 1, when projected, the above mentioned antenna 65 will enter the visual field of the above mentioned objective lens system 18.

Figure 4:
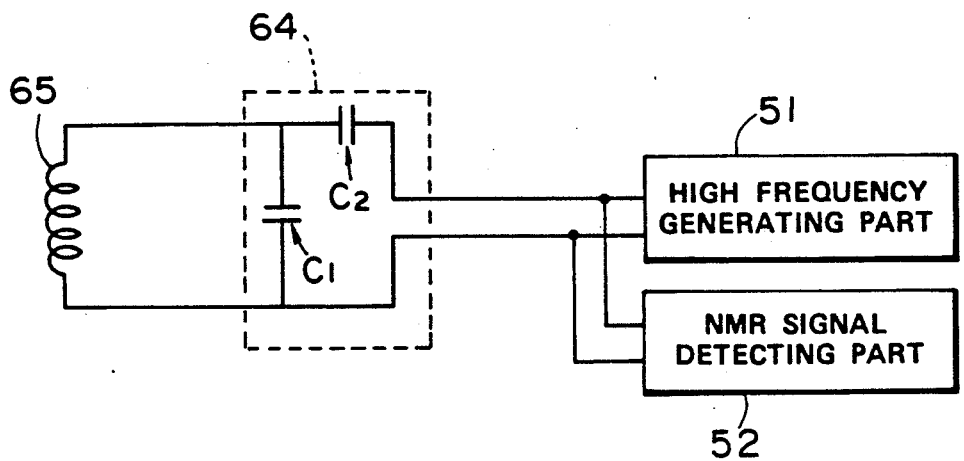

The NMR metering means including the above mentioned coil 65 is formed as shown, for example, in FIG. 4.

That is to say, a high frequency corresponding to the object nucleus kind to be metered will be output from the above mentioned high frequency generating part 51 and will be delivered to the above mentioned antenna 65 through a condenser part 64 and a high frequency magnetic field (signal) will be delivered to the living body from this antenna 65. The above mentioned condenser part 64 is provided with a condenser C1 in parallel with the above mentioned antenna 65 and a condenser C2 in series with the above mentioned antenna 65. A matching circuit matching the impedances on the side of the above mentioned antenna 65 and on the side of the high frequency generating part 51 and NMR signal detecting part 52 is formed of the condensers C1 and C2.

In this embodiment, the above mentioned antenna 65 transmits and receives signals. The NMR signal from the living body will be received by the above mentioned antenna 65 and will be input into the above mentioned NMR signal detecting part 52. Such information (NMR parameter) as relieving time (T1, T2) will be obtained in this NMR signal detecting part 52.

The operation at the time of metering NMR shall be explained in the following.

As shown in FIG. 3, the examinee 56 is mounted on the bed 55 and a static magnetic field is given to examinee 56 by the NMR apparatus 57. The NMR probe 61 is inserted through the channel 27 of the endoscope 1, the insertable part 2 of the endoscope 1 is inserted through the mouth cavity or the like of the examinee 56 while the antenna 65 at the tip of this NMR probe 61 is retracted into close contact with the tip surface of the tip part 6, an illuminating light is fed to the light guide 24 of the endoscope 1 and the upper layer part of the stomach wall or the like is observed with the observing optical system consisting of the objective lens system 18, image guide 21 and eyepiece part 4. For example, in case an abnormal position is discovered in the upper layer part of the stomach wall, as shown in FIG. 1 the signal cable 62 of the above mentioned NMR probe 61 is moved forward, the above mentioned antenna 65 is projected and is pushed against the abnormal position 59 as shown in FIG. 3. In this state, a high frequency is delivered to the above mentioned antenna 65 from the high frequency generating part 51 and a high frequency magnetic field (signal) is transmitted to the abnormal position from this antenna 65. By the way, it is desirable that the direction of this high frequency magnetic frequency intersects at right angles with the direction of the static magnetic field. The NMR signal from the abnormal position 59 is received by the above mentioned antenna 65 and is metered by the NMR signal detecting part 52 so that the physiological variation of the abnormal position 59, for example, whether it is a cancer or not may be detected.

In the thus formed first embodiment, the curvable tubes 13, wires 31, net tubes 12 and 16 and spiral tube 33 are formed of an austenitic stainless steel to be a paramagnetic or feeble magnetic material instead of a inartensitic stainless steel to be a usually extensively used ferromagnetic material, the entire endoscope is formed of another material than a ferromagnetic material and therefore, even if the endoscope is used within such ferromagnetic field as of the NMR apparatus, it will be so little influenced as not to be strongly attracted by a ferromagnetic field. Therefore, in case it is used as inserted in a body, even if a ferromagnetic field is applied, it will not be attracted by the magnetic field, will not have the operation obstructed and will be able to be used the same as in the normal state.

In the above mentioned first embodiment, the curvable tubes 13, wires 31 and net tubes 12, 16 and 33 are formed of an austenitic stainless steel but may be formed of such non-magnetic or diamagnetic material which is not a ferromagnetic material as a copper alloy or aluminum alloy. The tip part may be formed of such metal or rigid high molecular weight material.

In this embodiment, the NMR metering antenna 65 is not incorporated in the tip part 6 of the endoscope but is made removable. At the time of metering NMR, the above mentioned antenna 65 is projected so as to enter the visual field of the observing optical system of the endoscope 1. Therefore, the region in which the NMR is being metered by the above mentioned antenna can be easily confirmed.

As the NMR metering antenna 65 is not incorporated in the tip part 6 but is made removable, the tip part 6 of the insertable part 2 can be made as small and thin as in an endoscope not for metering NMR. Therefore, the NMR metering antenna 65 can be easily led into a body cavity.

Also, the NMR metering antenna 65 of an outside diameter as large as of the tip part 6 of the insertable part 2 of the endoscope 1 can be led into the body cavity.

By the way, not only the NMR probe 61 but also such treating tool as a forceps can be inserted through the above mentioned channel 27.

Figure 5:
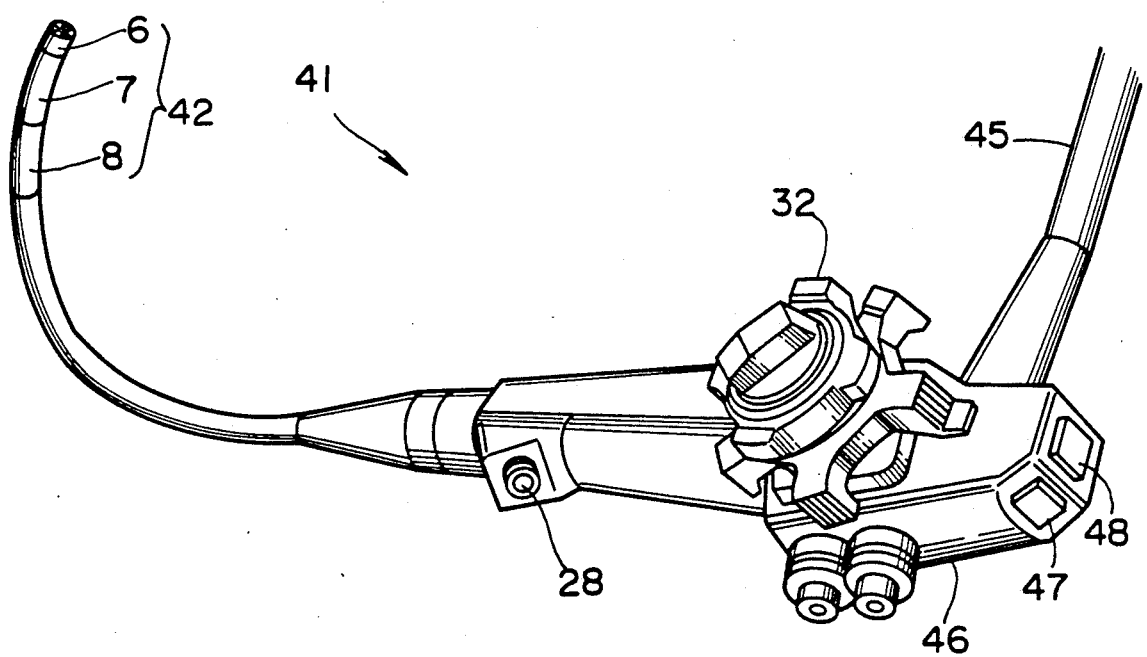
FIGS. 5 and 6 relate to the second embodiment of the resent invention.
Figure 6:
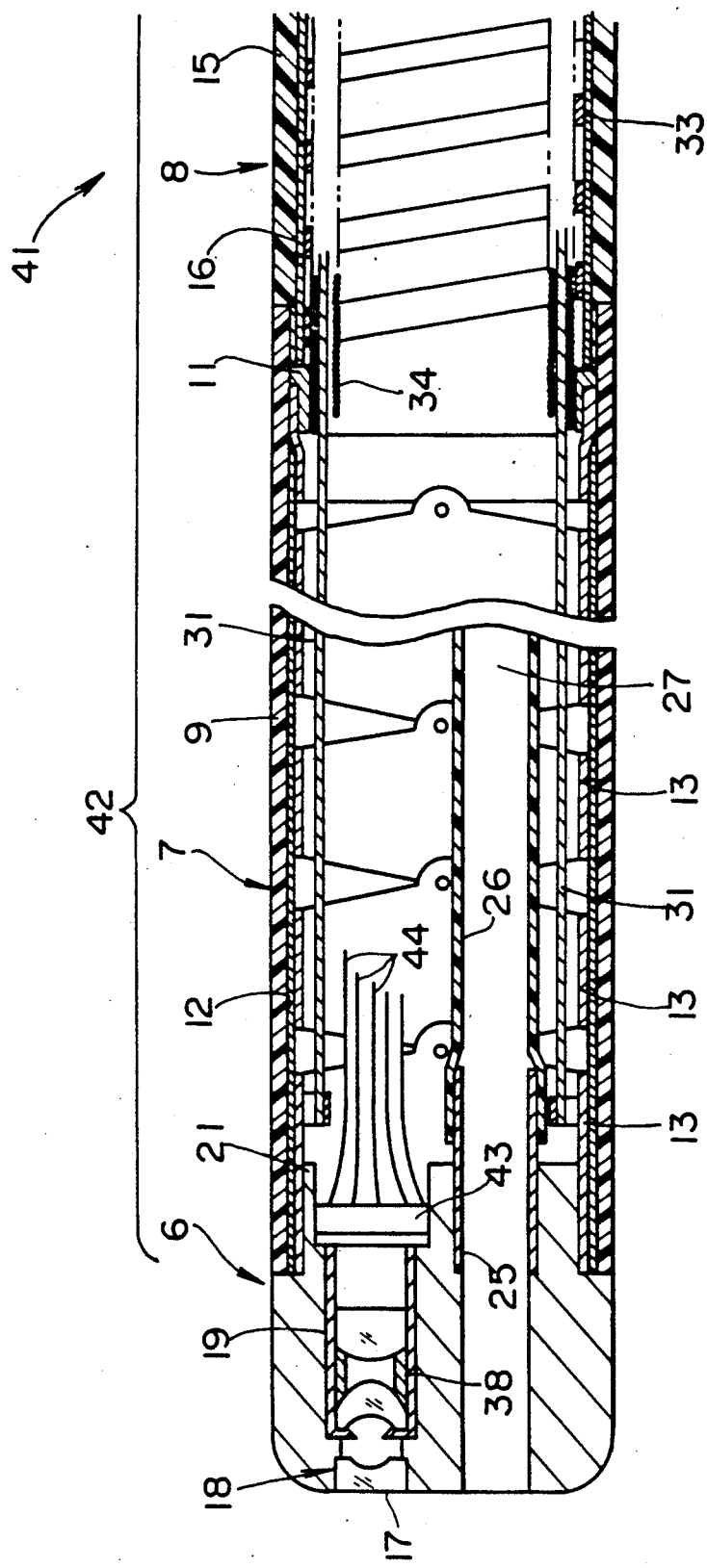

FIGS. 5 and 6 show the second embodiment of this invention.

This second embodiment shows an electronic endoscope 41 of a contour shown in FIG. 5. The structure of the tip side of the insertable part 42 is shown in FIG. 6.

In this electronic endoscope 41, a CCD (charge coupled device) 43 as a solid state imaging device instead of the image guide 21 is arranged in the focal plane of the objective lens system 18 in the optical endoscope shown in FIG. 2. Signal cables 44 for transmitting CCD driving signals and CCD output signals are connected to this CCD 43. The signal cables 44 inserted through the insertable part 42 are further inserted through the universal cord 45 and a connector (not illustrated) at the end of this universal cord 45 is connected to a control apparatus so that a video image imaged by the CCD 43 may be displayed in a monitor not illustrated.

By the way, the operating part 46 of this electronic endoscope 41 is provided with a freezing button for the operation of making the picture image displayed in the monitor a stationary picture and a releasing button 48 for the operation of photographing a stationary picture.

The others are substantially the same as in the above mentioned first embodiment. The same reference numerals are attached to the same corresponding members.

In this embodiment too, the respective parts of the electronic endoscope 41 are formed of such non-magnetic material as a feeble magnetic or paramagnetic material.

Therefore, the same as in the first embodiment, even if the endoscope is used within such ferromagnetic field as in the NMR apparatus, it will not be influenced by the ferromagnetic field.

Also, the same as in the first embodiment, the NMR probe 61 can be inserted through this treating tool channel 27.

The operations and effects of this embodiment are the same as in the first embodiment.

By the way, the first and second embodiments can be applied not only to the case of a medical endoscope but also to the case of an industrial endoscope. For example, a substance showing a super-conductivity even at a temperature considerably higher than the absolute temperature has been recently discovered and a ferromagnetic field can be obtained so comparatively easily that an apparatus utilizing such ferromagnetic field will be practiced more extensively. In such case, it will be necessary to investigate the interior of the apparatus in the operating state. The present invention can be extensively used even in such operating state (that is, within a ferromagnetic field).

Figure 7:
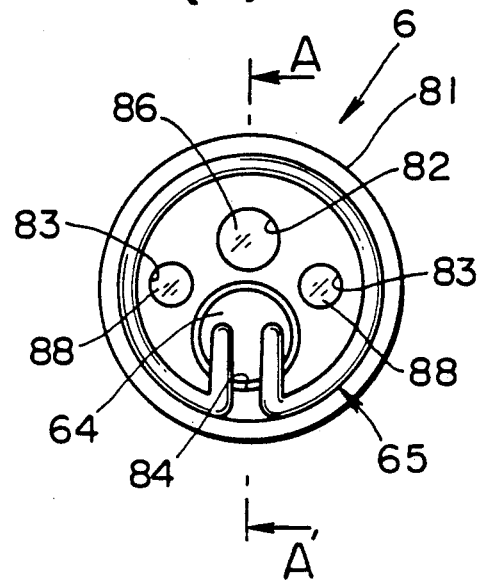
FIGS. 7 and 8 relate to the third embodiment of the present invention.
Figure 7:
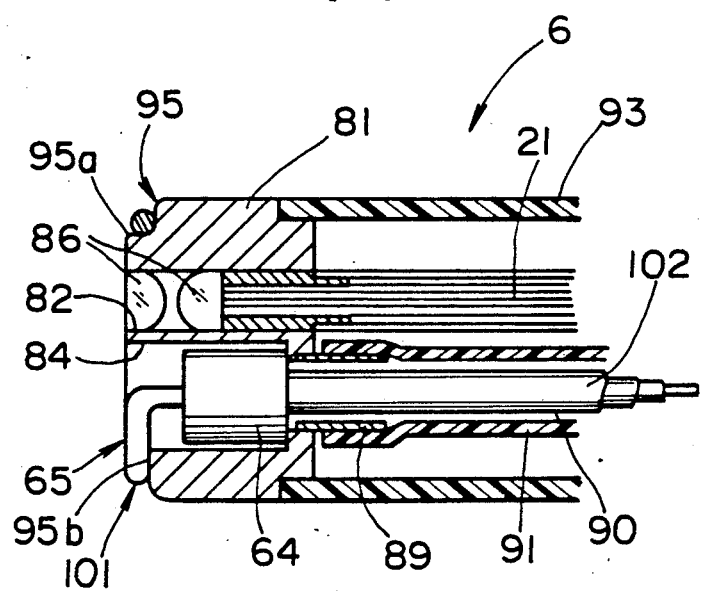
Figure 8:
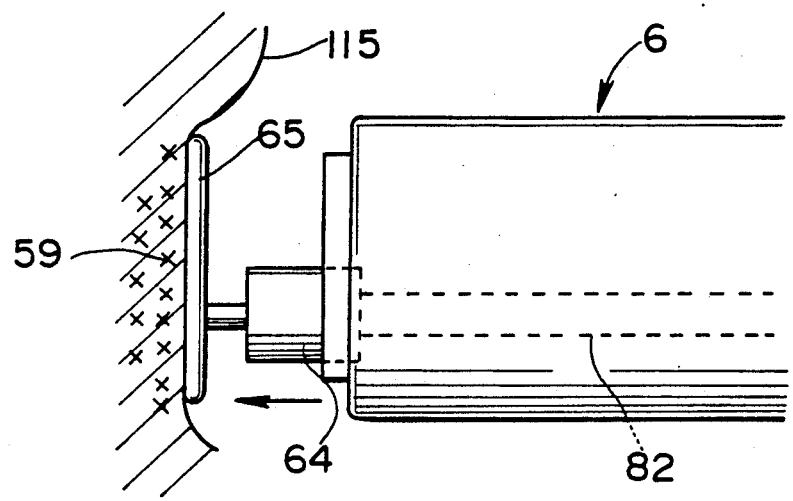

FIGS. 7 and 8 show the third embodiment of the present invention.

The entire formation of the endoscope system of this embodiment is substantially the same as in FIG. 3.

The tip part 6 of the insertable part 2 of the endoscope of this embodiment is formed as shown in FIGS. 7 (A) and 7 (B).

That is to say, the tip part 6 is provided with a substantially columnar tip part body 81 made of such rigid material as a metal. An observing through hole 82, for example, two illuminating through holes 83 and a channel through hole 84 passing parallelly in the axial direction through the insertable part 2 are formed through the above mentioned tip part body 81. The above mentioned observing through hole 82 is fitted on the tip side with an objective lens system 86. The tip surface of the image guide 21 inserted through the above mentioned insertable part 2 is arranged in the image forming position of this objective lens system 86. The object image formed by the above mentioned objective lens system is led to the eyepiece part 4 by the above mentioned image guide so as to be able to be observed from this eyepiece part 4. The above mentioned illuminating through hole 85 is fitted on the tip side with a light distributing lens 88. A light guide not illustrated is arranged on the rear end side of this light distributing lens 88. The above mentioned channel through hole 84 is formed to be smaller in the diameter on the rear end side. A channel pipe 89 is fitted on the rear end side of this small diameter part. A channel tube 91 forming a treating tool channel 90 is connected to this channel pipe 89. This channel tube 91 is inserted through the above mentioned insertable part 2 and is connected to a leading inlet provided in the operating part 3.

A flexible tube 93 forming a jacket tube of the insertable part 2 is connected to the rear end part of the above mentioned tip part body 81. The above mentioned image guide 21, light guide and channel tube 91 are contained within this tube 93.

Now, in this embodiment, as shown in FIG. 7 (B), an antenna containing part 95 consisting of a peripheral groove (or step) 95 a formed on the outermost peripheral side of the tip surface and a wide groove 95 a formed between the part positioned on the outer peripheral side of the channel through hole 84 of this peripheral groove 95 a and the above mentioned channel through hole 84 is formed on the above mentioned tip part body 81.

Also, in this embodiment, the NMR probe 101 for metering NMR is to be inserted through the above mentioned channel 90. On this NMR prove 101, a condenser part 64 is connected to the tip of a signal cable, for example, a coaxial cable 102 inserted through the above mentioned channel 90 and an NMR metering antenna 65 is connected to the tip side of this condenser part 64. The above mentioned antenna 65 is formed like a one-wind loop of an outside diameter substantially equal to or somewhat smaller than the outside diameter of the above mentioned tip part 6 and can be contained in the antenna containing part 95 formed in the above mentioned tip part body 81. By the way, the above mentioned antenna containing part 95 is formed to be of a depth larger than the thickness of the above mentioned antenna 65 so that, when the antenna 65 is contained, it will not project out of the tip surface and side surface of the tip part 6. The above mentioned antenna 65 is bent at both ends, as shown in FIG. 7 (A), to the inner peripheral side, that is, to the channel through hole 84 side along the groove 95b of the antenna containing part on the outer peripheral side of the above mentioned channel through hole 184, is then bent at both ends, as shown in FIG. 7 (B), from the front position to the rear end side of the channel through hole 84 and is connected at both ends to a condenser part 64 contained within the above mentioned channel through hole 84. This condenser part 64 is formed to be substantially columnar in the contour and is regulated in the movement to the rear end side by the step formed by the small diameter part of the above mentioned channel through hole 84. When this condenser part 64 is in the rearmost position, the above mentioned antenna 65 will be contained in the above mentioned antenna containing part 95. The above mentioned coaxial cable 102 is led on the base side out of the above mentioned leading inlet 28 and is connected to the high frequency generating part 51 and NMR signal detecting part 52 as shown in FIG. 3. By moving the above mentioned coaxial cable 102 in the axial direction, as shown in FIG. 8, the above mentioned antenna 65 can be projected out of and retracted into the tip part 61. By the way, in FIG. 8, the reference numeral 115 represents a living body.

The NMR metering means including the above mentioned antenna 65 is formed as shown, for example, in FIG. the same as in the first embodiment.

The other formations are the same as in the first embodiment.

Thus, in this embodiment, the NMR metering antenna 65 is not incorporated in the tip part 6 of the endoscope but is made removable and the antenna containing part 95 for containing the NMR metering antenna 65 formed to be like a one-wind loop is provided in the tip part 6 of the above mentioned endoscope. This antenna containing part 95 is formed by a peripheral groove 95a along the contour of the tip part 6 at the tip of the tip part 6 and can contain the above mentioned antenna 65 without substantially changing the contour of the tip part 6 and without projecting the above mentioned antenna 65 out of the tip surface and side surface of the tip part 6. The antenna 65 of the NMR probe 101 inserted through the channel 90 is contained in the above mentioned antenna containing part 95 and can be led into a body.

Therefore, the NMR metering antenna is not incorporated in the tip part 6 but is removably easily contained in the tip part 6 and can be led into the body. The tip part 6 can be made as small and thin as in an endoscope not for metering NMR.

By the way, in this embodiment, the antenna containing part may be formed by Providing a peripheral groove somewhat inside the outer periphery not on the outermost peripheral side of the tip surface of the tip part body 81.

By the way, not only the NMR prove 101 but also such treating tool as a forceps can be inserted through the above mentioned channel 90.

Figure 9:
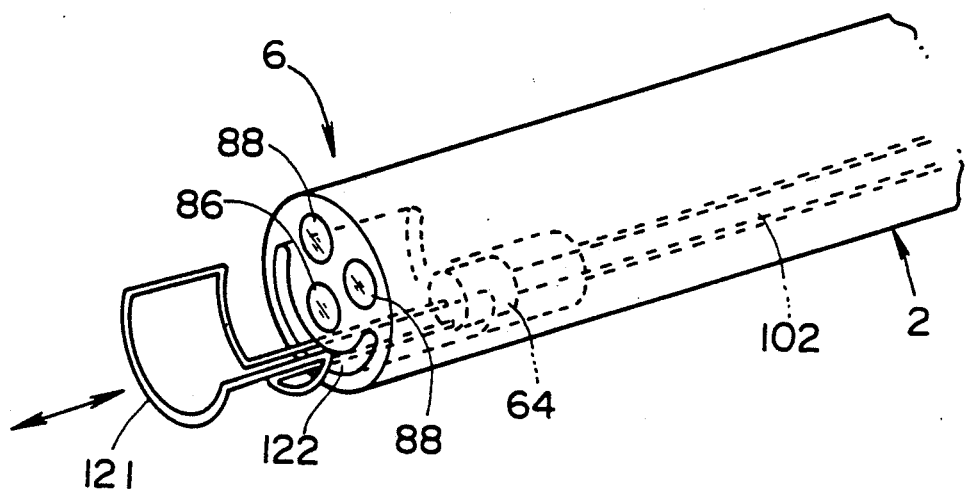
FIG. 9 is a perspective view showing the tip part of an endoscope of the fourth embodiment of the present invention.

FIG. 9 shows the fourth embodiment of the present invention.

In this embodiment, an NMR metering antenna 121 is wound in a semicylindrical saddle form in which the outside diameter is somewhat smaller than the outside diameter of the endoscope tip part 6 and the axial direction is parallel with the axial direction of the tip part 6.

On the other hand, a semicylindrical antenna containing part 122 opening on the tip surface of the tip part 6, having the outside diameter somewhat smaller than the outside diameter of the tip part 6 and having the axial direction parallel with the axial direction of the tip part 6 is provided on the outer peripheral side of the above mentioned tip part 6. This antenna containing part 122 communicates with a channel provided within the insertable part 2. The same as in the third embodiment, the above mentioned antenna 121 is contained within the above mentioned antenna containing part 122, is led into a body and can be projected forward from the above mentioned antenna containing part 122 by moving the coaxial cable 102 in the axial direction as in FIG. 9.

The other formations are the same as in the third embodiment.

In this embodiment, the direction of the high frequency magnetic field transmitted from the above mentioned antenna 121, that is, the detecting direction intersects at right angles with the axial direction of the insertable part 2.

In this embodiment, as the above mentioned coil containing part 122 is formed to be semicylindrical along the contour of the tip part 6, the same as in the third embodiment, the tip part 6 can be made as small and thin as in an endoscope not for metering NMR.

By the way, the antenna containing part may be provided on the side part of the tip part 6 so that the NMR metering antenna may project sidewise of the tip part 6 out of this containing part.

In the third and fourth embodiment, for the optical observing means, as in the second embodiment, an imaging means consisting of a solid state imaging device may be provided in the tip part or, as in the endoscope 1 of the first embodiment, a television camera may be provided in the eyepiece part of such endoscope whereby a naked observation is possible as a fiber scope.

Figure 10:
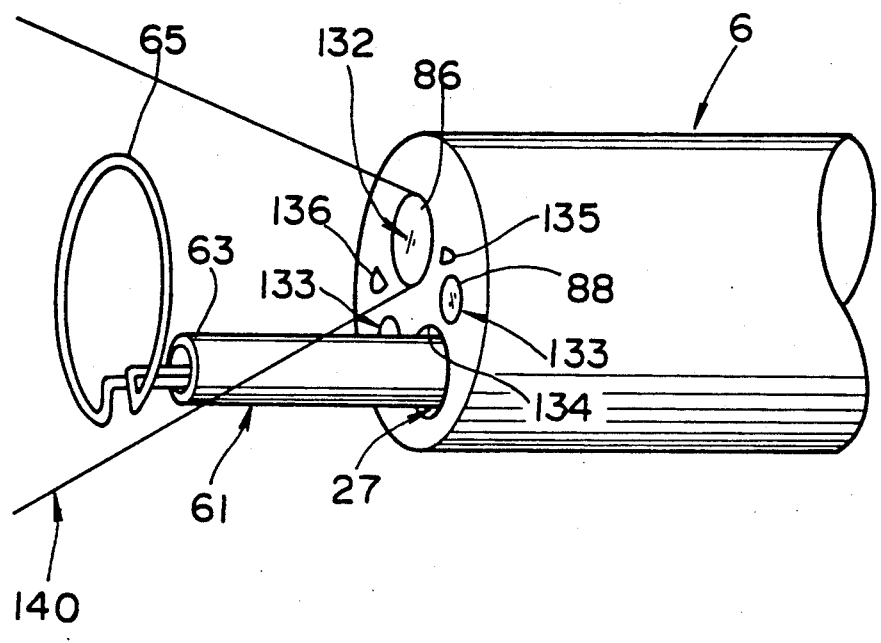
FIGS. 10 and 11 relate to the fifth embodiment of the present invention.
Figure 11:
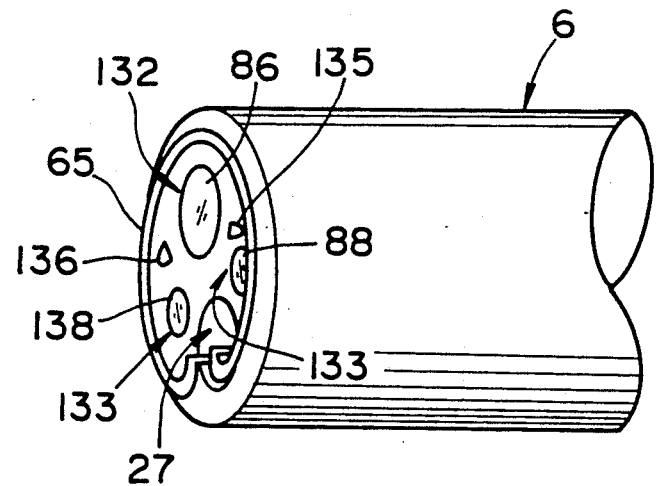

FIG. 10 and 11 show the fifth embodiment of the present invention.

In an endoscope in this embodiment, an observing window 132, for example, two illuminating windows 133, a channel through hole 134 and an air feeding nozzle 135 and water feeding nozzle 136 opening toward the above mentioned observing window 132 are provided on the tip surface of the tip part 6. The above mentioned observing window 132 is fitted with an objective lens system 86 as an observing optical system. The tip surface of an image guide not illustrated inserted through the insertable part 2 is arranged in the image forming position of this objective lens system 86. By the way, the optical axis of the above mentioned objective lens system 86 is substantially parallel with the axial direction of the insertable part 2 and is of a straight viewing type.

The above mentioned illuminating window 133 is fitted with a light distributing lens 88 and a light guide not illustrated is arranged on the rear end side of this light distributing lens 88. A channel tube not illustrated forming a channel 27 is connected to the rear end of the above mentioned channel through hole 134. This channel tube is inserted through the above mentioned insertable part 2 and is connected to a leading inlet 28. An air feeding channel tube and water feeding channel tube not illustrated are connected respectively to the above mentioned air feeding nozzle 135 and water feeding nozzle 136, are inserted through the above mentioned insertable part 2 and light guide cable 5 and are connected to the above mentioned connector 53.

Now, in this embodiment, as shown in FIGS. 10 and 11, the same as in the first embodiment, an NMR probe 61 is to be inserted through the above mentioned channel 27.

In this embodiment, the antenna 65 is formed to be like a one-wind loop of an outside diameter substantially equal to or somewhat smaller than the outside diameter of the above mentioned tip part 6 of a conductor, for example, of a circular cross-section and its center axis substantially coincides with the center axis of the above mentioned insertable part 2 and is substantially parallel with the optical axis of the above mentioned objective lens system 86.

As shown in FIG. 10, when projected, the above mentioned antenna 65 will enter the visual field of the above mentioned Objective lens system 86.

As shown in FIG. 11, when retracted, the above mentioned antenna 65 will be arranged on the outer peripheral side of such respective components provided on the tip surface of the tip part 6 as the observing window 132, illuminating windows 133, air feeding nozzle 135 and water feeding nozzle 136 so as not to overlap on them. In such case, the above mentioned antenna 65 will be arranged smoothly along the outer surface of the tip part 6 so as not to greatly project out of the tip surface. Therefore, the antenna 65 may be formed to be flat with the conductor of a cross-section wide in the diametral direction.

The other formations are the same as in the first embodiment.

Thus, in this embodiment, the NMR metering antenna 65 is not incorporated in the tip part 6 but is made removable. At the time of metering NMR, when the above mentioned antenna 65 is projected, the antenna 65 will enter the visual field 140 of the observing optical system of the endoscope, the center axis of this antenna 65 will become substantially parallel with the optical axis of the observing optical system and the detecting direction of the antenna 65 and the optical axis direction of the observing optical system will substantially coincide with each other. Therefore, the region in which NMR is being metered by the above mentioned antenna 65 can be easily confirmed.

Also, as the NMR metering antenna 65 is not incorporated in the tip part 6 but is made removable, the tip part 6 can be made as small and thin as in an endoscope not for metering NMR.

By the way, not only the NMR probe 61 but also such treating tool as a forceps can be inserted through the above mentioned channel 27.

The other operations and effects are the same as in the first embodiment.

By the way, in this embodiment, an antenna 65 containing part may be provided in the tip part 6 as in the third embodiment.

Figure 12:
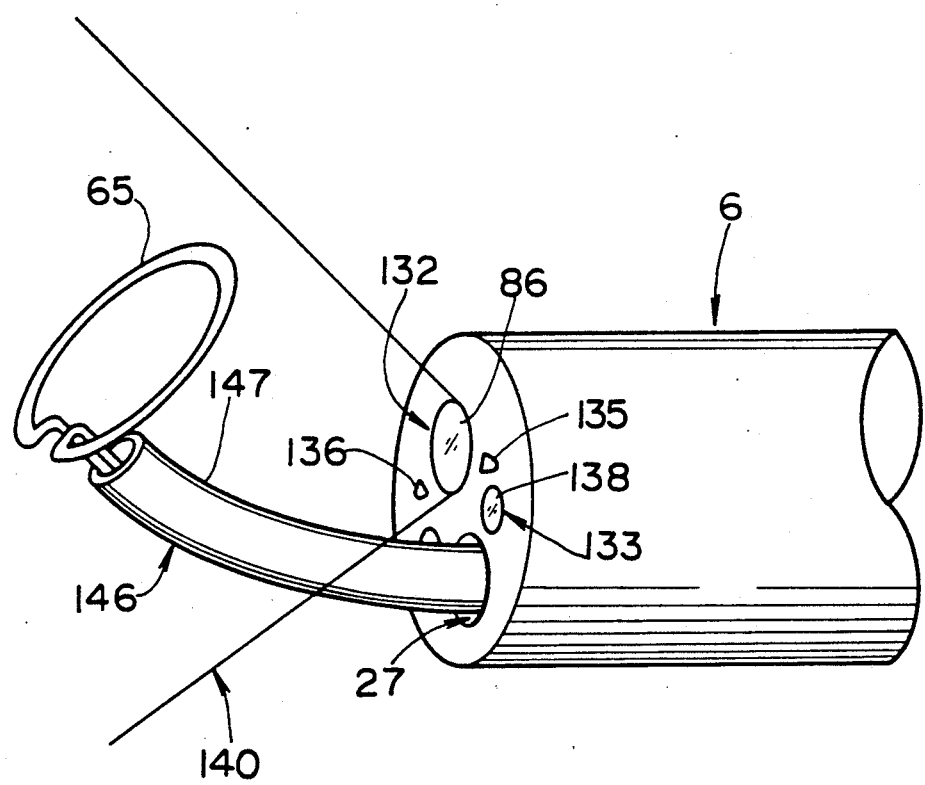
FIG. 12 is a perspective view showing the tip part of an insertable part of an endoscope of the sixth embodiment of the present invention.

FIG. 12 shows the sixth embodiment.

In this embodiment, the coating tube 147 of the NMR probe 146 is resilient at least on the tip side and has such curving habit as to curve to the optical axis side of the objective lens system 86.

In this embodiment, when the antenna 65 is projected, it will positively enter the visual field 140 of the observing optical system and therefore the metering region will be more easily confirmed.

The center axis of the antenna 65 is not parallel or vertical to the optical axis of the observing optical system, is displaceable and can be positively closely contacted with the metering position.

The other formations, operations and effects are the same as in the fifth embodiment.

Figure 13:
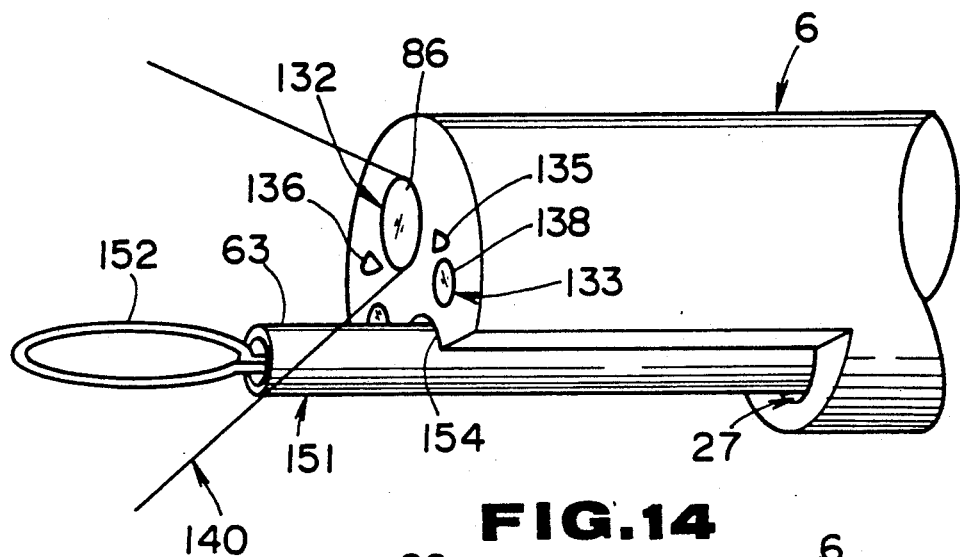
FIGS. 13 to 15 relate to the seventh embodiment of the present invention.
Figure 14:
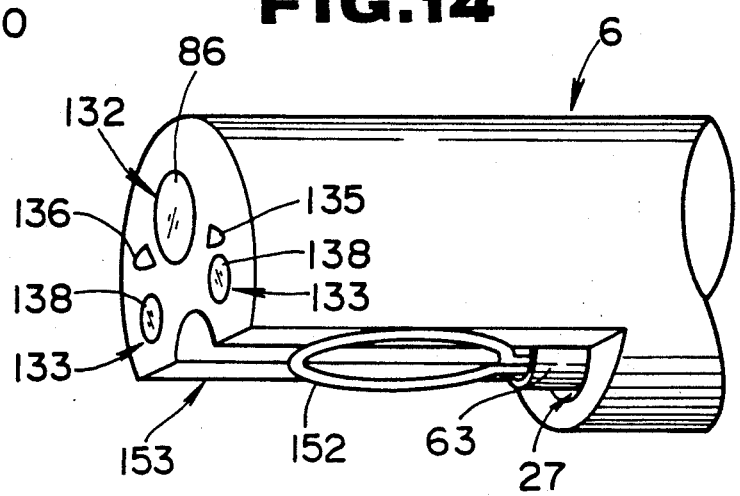
Figure 15:
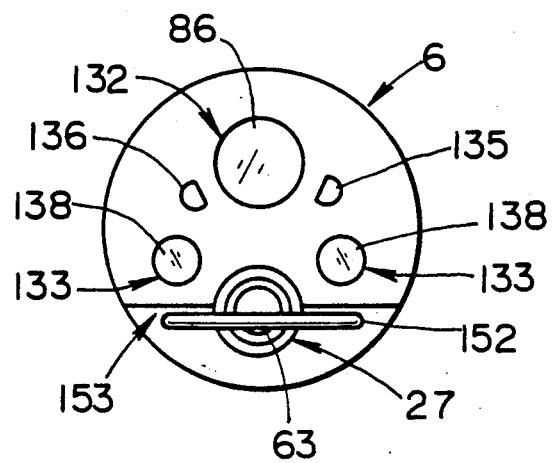

FIGS. 13 to 15 show the seventh embodiment of the present invention.

In this embodiment, an antenna 152 of an NMR probe 151 is formed to be like a one-wind loop whose center axis intersects substantially at right angles with the axial direction of the insertable part 2.

The tip part 6 is provided with an incision 153 incising the outer peripheral side substantially from the axis center of the channel in the rear of the tip surface. As shown in FIG. 14, when the above mentioned antenna 152 is retracted, it will be contained in the above mentioned incision 153 so as not to project out of the tip surface of the tip part 6. As shown in FIG. 15, the above mentioned antenna 152 is formed to be of a size contained within the circle of the cross-section of the tip part 6 when the antenna 153 is contained within the above mentioned incision 153.

A guide groove 154 of a semicircular cross-section continuing to the channel 27 is formed in the above mentioned incision 153. When the coating tube 63 of the above mentioned NMR probe 151 is moved forward along the above mentioned guide groove 154, the above mentioned antenna 152 will be projected forward and will enter the visual field 140 of the objective lens system 86 as shown in FIG. 13.

According to this embodiment, the center axis of the antenna 152 and the optical axis of the observing optical system are substantially vertical to each other, the visual field is Little obstructed by the above mentioned antenna and the metering region can be confirmed.

The other operations and effects are the same as in the first embodiment.

Figure 16:
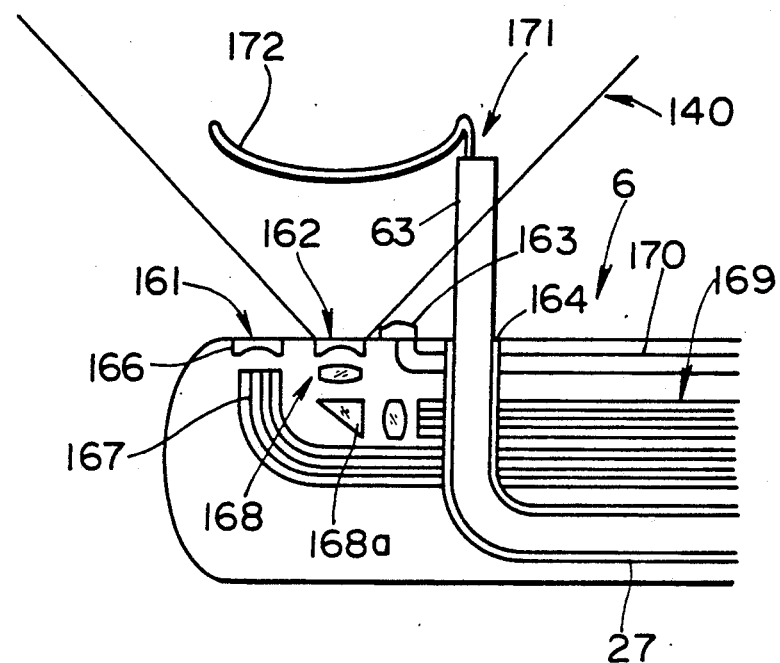
FIGS. 16 and 17 relate to the eighth embodiment of the present invention.
Figure 17:
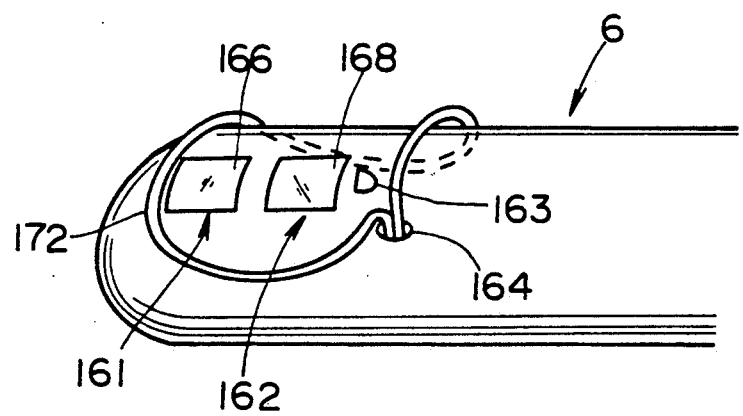

FIGS. 16 and 17 show the eighth embodiment of the present invention.

This embodiment shows a side viewing type endoscope.

As shown in these drawings, an illuminating window 161, an observing window 162 and an air and water feeding nozzle 163 opening toward this observing window 162 are provided from the tip side in the axial direction of the insertable part 2 on one side of the tip part 6. An opening 164 of the channel 27 is provided a little sidewise on the rear end side of the above mentioned air and water feeding nozzle 163.

The above mentioned illuminating window 161 is fitted with a light distributing lens 166. A light guide 167 is provided on the rear end side of this light distributing lens 166, is inserted through the insertable part 2 and Light guide cable 5, is bent on the tip side to the above mentioned illuminating window 161 side and is opposed on the tip surface to the above mentioned light distributing lens 166.

The above mentioned observing window 162 is fitted with an objective lens system 168 whose visual field direction is set sidewise of the insertable part 2. Such optical member 168 a bending the optical axis as a dach prism is interposed in this objective lens system 168 to bend the optical axis of the objective lens system 168 substantially at right angles to the base side. The tip surface of the image guide 169 is arranged in the image forming position of this objective lens system 168.

An air and water feeding pipe 170 is connected to the above mentioned air and water feeding nozzle 163, is inserted through the insertable part 2 and light guide cable 5 and is connected to the connector 53.

The above mentioned channel 27 is bent on the tip side substantially at right angles to the side of the tip part and communicates with the above mentioned opening 164. By the way, the path leading to this opening 164 from the bent part of this channel 27 is formed to be substantially linear.

On the other hand, the NMR probe 171 in this embodiment is coated with a coating tube 63. An antenna 172 exposed out of the opening 164 of the above mentioned channel 27 is connected to the tip of a signal cable inserted through the above mentioned channel 27, is wound to be like a one-wind loop whose center axis is substantially parallel with the optical axis of the observing optical system and is curved so as to be in close contact with the side of the above mentioned tip part 6 in case it is retracted as shown in FIG. 17. When the above mentioned signal cable is moved, as shown in FIG. 16, the antenna 172 will be projected sidewise out of the above mentioned tip part 6 and will enter the visual field 140 of the observing optical system. As shown in FIG. 17, the above mentioned antenna 172 is arranged on the periphery of such respective components provided on the side part of the tip part 6 as the illuminating window 161, observing window 162 and air and water feeding nozzle 163 so as not to be overlapped on these components when the antenna 172 is retracted.

The other formations are the same as in the fifth embodiment.

In this embodiment, the detecting direction of the above mentioned antenna 172 is substantially parallel with the optical axis on the entrance side of the objective lens system 168 and is in the direction intersecting substantially at right angles with the axial direction of the insertable part.

In case the endoscope insertable part 2 is to be inserted into a body, as shown in FIG. 17, the above mentioned antenna 172 will be retracted to be in close contact with the side part of the tip part 6. On the other hand, at the time of metering NMR, as shown in FIG. 16 the antenna 172 will be projected to enter the visual field 140 of the observing optical system so that the metering region may be confirmed.

By the way, in this embodiment, too, a containing part for containing the above mentioned antenna 172 may be provided on the side part of the tip part 6.

The other operations and effects are the same as in the fifth embodiment.

Figure 18:
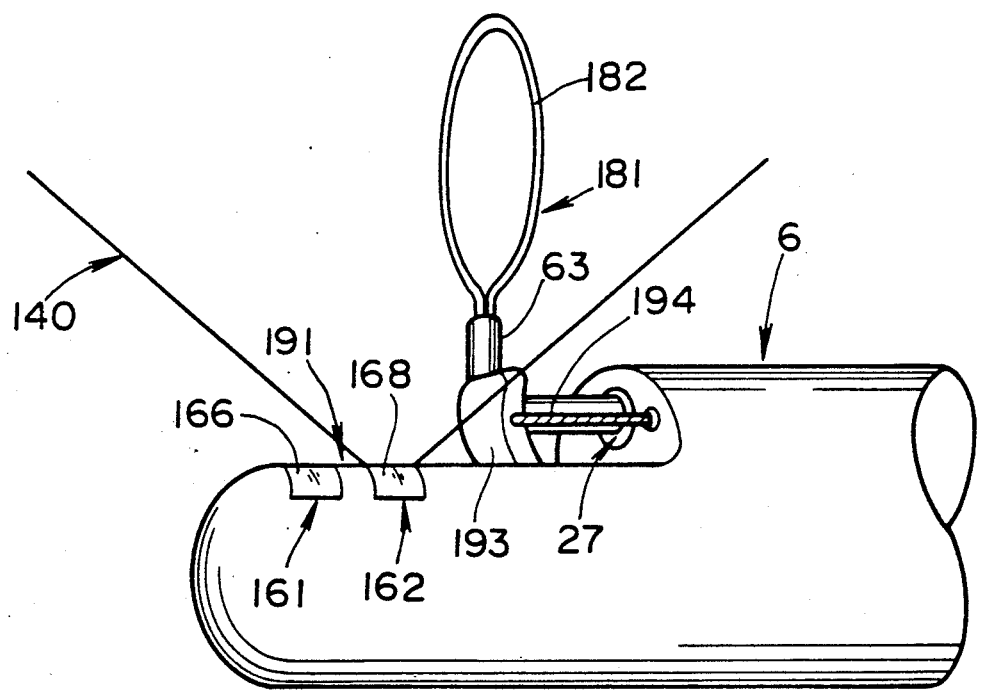
FIG. 18 is a perspective view of the tip part of an insertable part of an endoscope of the ninth embodiment of the present invention.

FIG. 18 shows the ninth embodiment of the present invention.

In this embodiment, a flat part 191 made by incising the side part in the axial direction of the insertable part 2 is formed in the tip part 6. An illuminating window 161 and observing window 162 form the tip side are provided in the axial direction of the insertable part 2 on this flat part 191. A channel 27 is provided on the outer peripheral side on the above mentioned flat part 191 side and is opened at the tip toward this flat part 191 side at the step in the boundary with the above mentioned flat part 191.

A treating tool leader 193 curvable on the tip side is arranged in the rear of the above mentioned observing window 162. A leading wire 194 for curving this treating tool leader 193 is connected to the side part on the tip side of this treating tool leader 193, is inserted through the insertable part 2 and is connected to an operating knob not illustrated provided on the operating part 3. When the above mentioned leading wire 194 is pulled and operated, the above mentioned treating tool leader 193 will be curved on the tip side, will be curved on the tip side, will be inserted through the above mentioned channel 27 and will be able to raise the tip side of an NMR probe 181 projected out of the opening of this channel 27.

In this embodiment, when the antenna 182 of the NMR probe 181 is projected forward and the treating tool leader 193 is curved on the tip side to raise the NMR probe 181 on the tip side, as shown in FIG. 18, the above mentioned antenna 182 will project sidewise of the tip part 6 and will enter the visual field 140 of the observing optical system. In this state, the center axis of the above mentioned antenna 182 will be substantially vertical to the optical axis of the objective lens system 168.

When the curve of the above mentioned treating tool leader 193 is released and the above mentioned antenna 182 is retracted, this antenna 182 will approach the flat part 191 of the tip part 6 and will be arranged on the periphery of such respective components provided on this flat part 191 as the illuminating window 161 and observing window 162 so as not to be overlapped on these components. The above mentioned antenna 182 is formed to be of such size as will be contained within the circle of the cross-section of the tip part 6 when the antenna 182 approaches the above mentioned flat part 191.

According to this embodiment, at the time of metering NMR, the center axis of the antenna 182 and the optical axis of the observing optical system will be substantially vertical to each other, the visual field will be little obstructed by the above mentioned antenna 182 and the metering region will be able to be confirmed.

By the way, as shown in the above mentioned fifth and eighth embodiments, in case the center axis of the NMR metering antenna and the optical axis of the observing optical system are substantially parallel with each other, the metering region will be confirmed most easily but, as shown in the sixth, seventh and ninth embodiments, even in another case than that, at the time of metering NMR, if the above mentioned antenna is arranged so as to be within the visual field of the observing optical system, the metering region will be able to be confirmed.

By the way, in the fifth to ninth embodiments, the NMR metering antenna may be always within the visual field of the observing optical system.

As an optical observing means, as in the second embodiment, the tip part may be provided with an imaging means consisting of a solid state imaging device or the eyepiece part of such endoscope whereby a naked eye observation is possible as a fiber scope may be provided with a television camera.

FIG. 19 to 22 show the tenth embodiment of the present invention.

Figure 21:
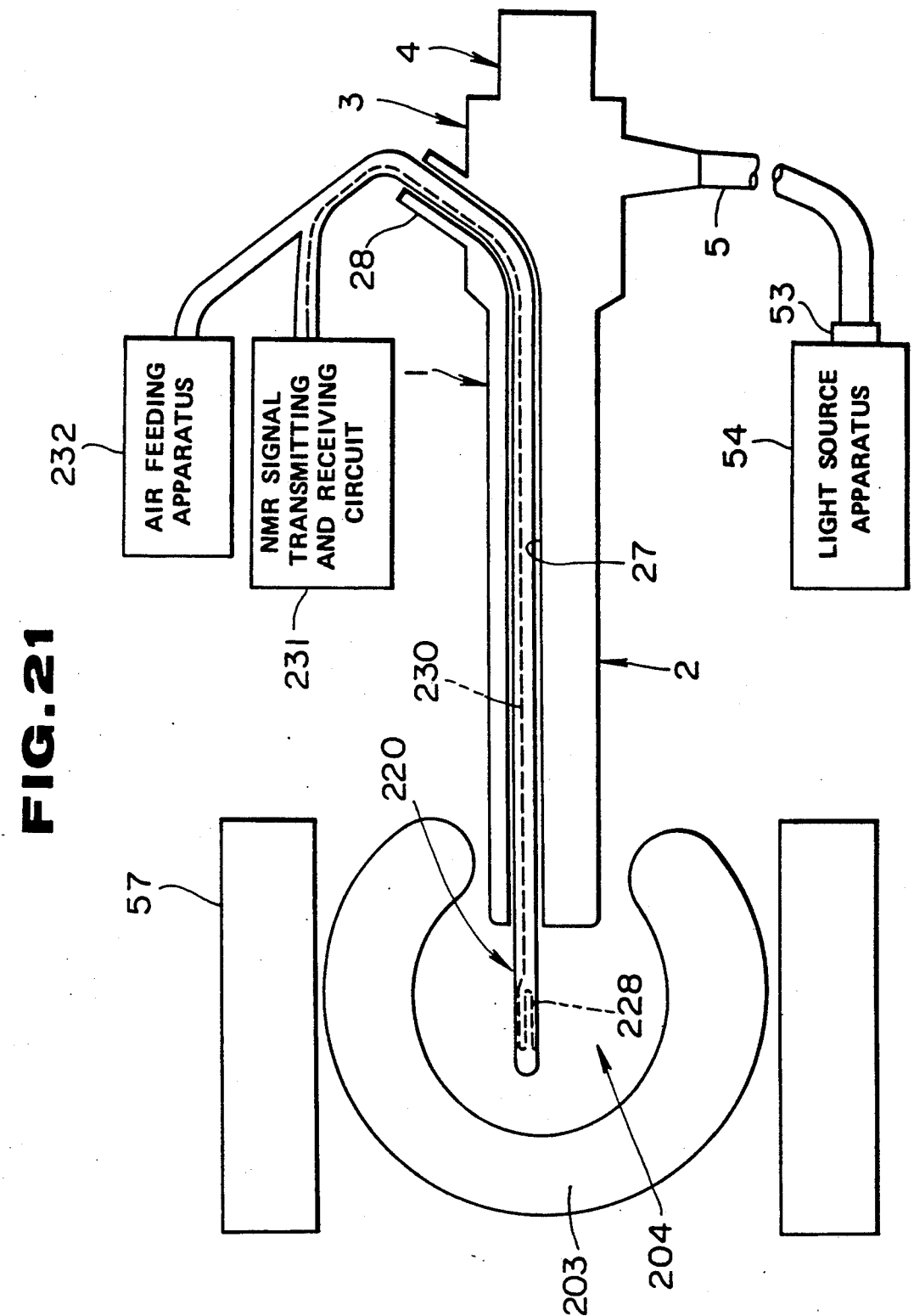

As shown in FIG. 21, an NMR metering antenna apparatus 220 of this embodiment is inserted through the treating tool channel 27 of the same endoscope 1 as of the first embodiment and is inserted into the body cavity 204 of an examinee 203.

Figure 19:
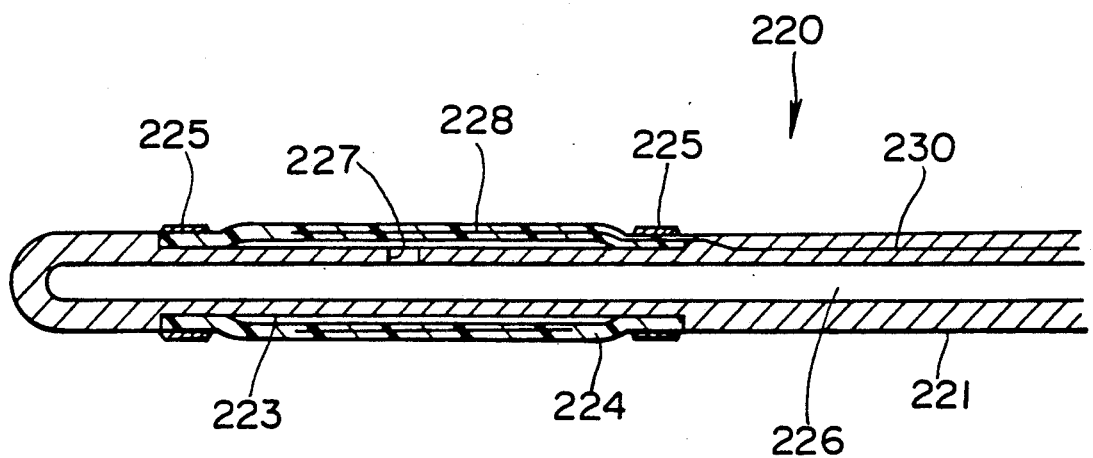
FIGS. 19 to 22 relate to the 10th embodiment of the present invention.
Figure 20:
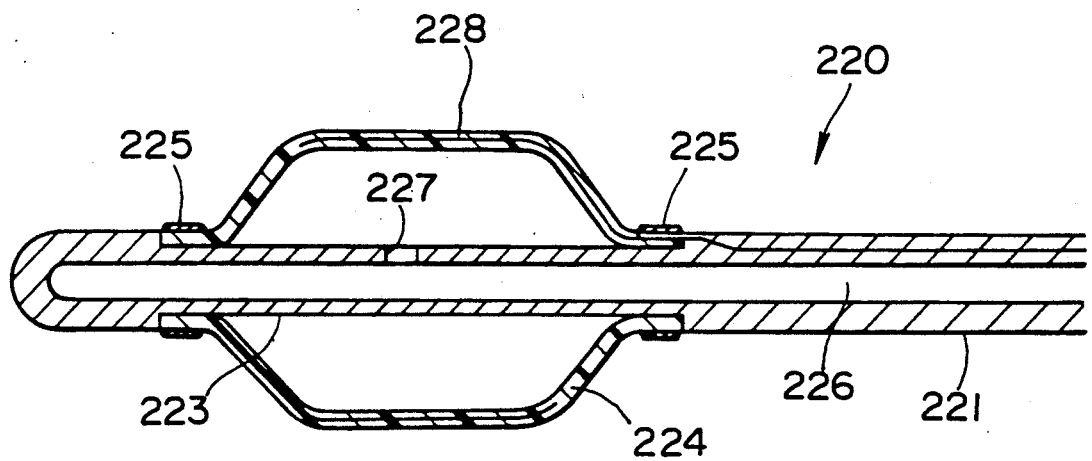

As shown in FIG. 19, the NMR metering antenna apparatus 220 of this embodiment is provided with a hollow shaft part 221 inserted through the above mentioned treating tool channel 27. The hollow part of this shaft part 221 is an air feeding patch and this shaft part 221 is closed at the tip. A wide groove part 223 is peripherally formed on the outer peripheral part on the tip side of the above mentioned shaft part 221. AN extensible balloon 224 is fitted to this groove part 223 by fixing members 225. An air passing hole 227 making the air feeding path 226 of the above mentioned shaft part 221 communicate with the interior of the above mentioned balloon is provided in a position inside the above mentioned balloon 224 on the above mentioned shaft part 221. An NMR metering high frequency antenna 228 is embedded within a film forming the above mentioned balloon 224, is arranged on the entire periphery of the above mentioned balloon 224 while bending alternately in the directions reverse to the axial direction as shown, for example, in FIG. 212 and is connected at both ends to a cable 230 embedded, for example, in the above mentioned shaft part 221. As shown in FIG. 21, the above mentioned cable 230 is connected on the base side to an NMR transmitting and receiving circuit 231 and the air feeding path 226 of the above mentioned shaft part 221 is connected to an air feeding apparatus 232. When, for example, air is fed into the air feeding path 226 of the above mentioned shaft part 221 from this air feeding apparatus 232, this air will be fed into the above mentioned balloon 224 through the above mentioned air passing hole 227 and this balloon will be inflated as shown in FIG. 20.

By the way, such high frequency generating part 51 and NMR signal detecting part 52 as are shown in FIG. 4 are provided within the above mentioned NMR transmitting and receiving circuit 231. The formation of the NMR metering means including the above mentioned antenna 228 is the same as in FIG. 4.

The other formations are the same as in the first embodiment.

The operation of this embodiment formed as in the above shall be explained in the following.

Figure 22:
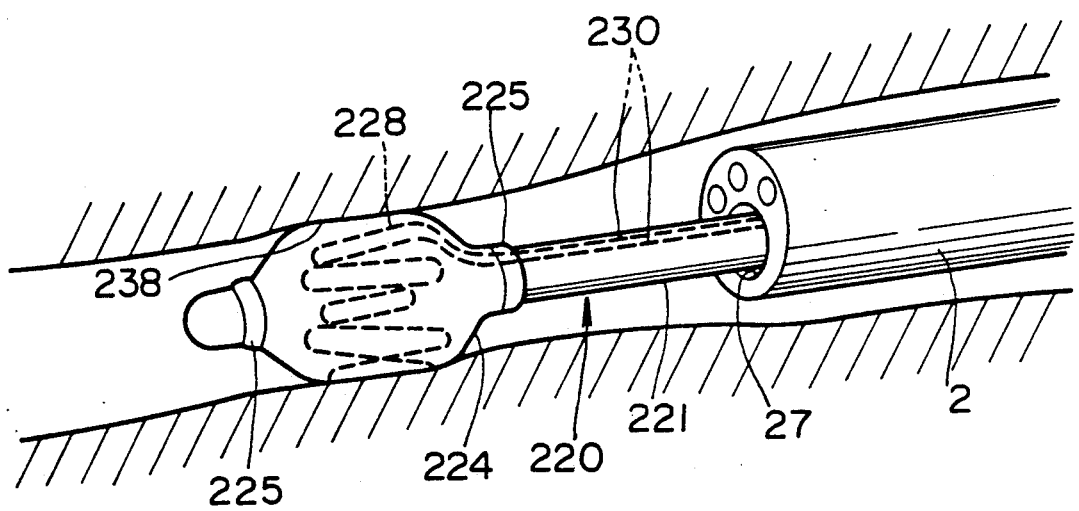

As shown in FIG. 21, a static magnetic field is given to the examine by the NMR apparatus 57. The NMR metering antenna apparatus 220 with the balloon 224 contracted is inserted into the treating tool channel 27 of the endoscope 1, the insertable part 2 of the endoscope 1 is inserted into the body cavity 204 through the month cavity or the like of the examinee 203, an illuminating light is fed to the light guide of the endoscope 1 from the light source apparatus 54 and an object image by this illuminating light is observed from the eyepiece part 4. In the case of metering NMR within a pipe cavity or the Like, as shown in FIG. 22, the above mentioned antenna apparatus 220 is projected on the tip side out of the treating tool channel 27, air is fed into the air feeding path 226 of the shaft part 221 from the air feeding apparatus 232 to inflate the balloon 224 and this balloon 224 is fixed in a metering object position 238. As the antenna 228 is embedded in this balloon 224, this antenna 228 will be also fixed in the metering object position 238. In this state, a high frequency is transmitted from the high frequency generating part 51 to the above mentioned antenna 228 and a high frequency signal is transmitted from this antenna 228 to the metering object position 238. When the NMR signal from the metering object position 238 is received by the above mentioned antenna 228 and is metered by the NMR signal detecting part 52, the physiological variation of the metering object position, for example, whether it is a cancer or not will be able to be detected.

Thus, in this embodiment, the NMR metering antenna 228 is provided in the balloon 224. Therefore, when this balloon 224 is inflated and is fixed to the object position 238 within the body cavity, the antenna 228 provided in this balloon 224 will be able to be easily fixed to the object position 238 within a body cavity or particularly within a tube cavity.

Also, according to this embodiment, the balloon 224 can be method on the entire periphery by once while the balloon 24 is fixed.

The other operations and effects are the same as in the first embodiment.

Figure 23:
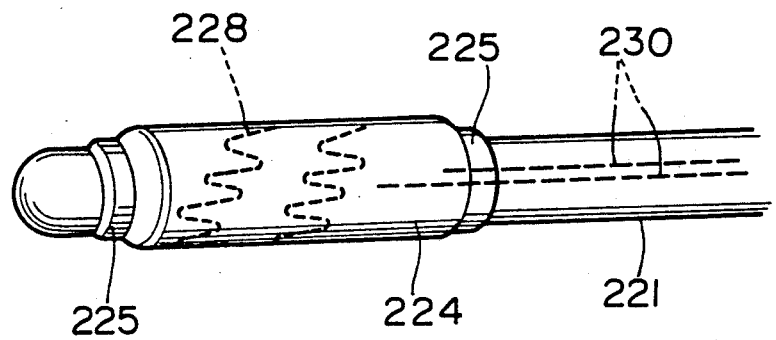
FIGS. 23 and 24 relate to the 11th embodiment of the present invention.
Figure 24:
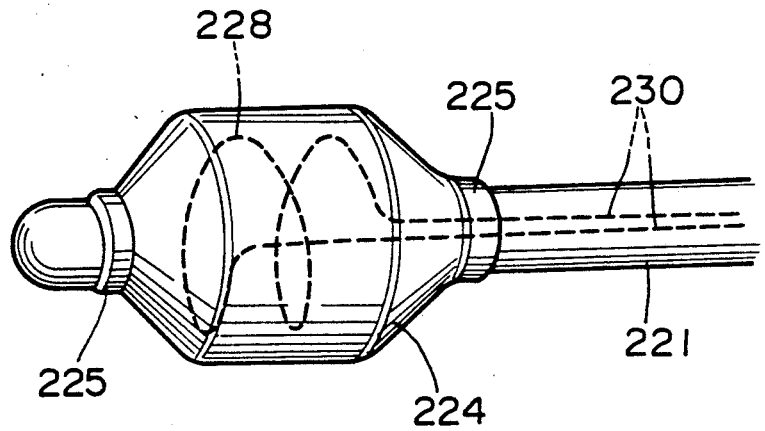

FIGS. 23 and 24 show the 11th embodiment of the present invention.

In this embodiment, as shown in FIG. 24, an antenna 228 is provided to be in the form, for example, of a twice wound spiral when the balloon 224 is inflated. As shown in FIG. 23, the above mentioned antenna 228 is flexible enough, for example, to be finely alternately bent and contracted when the balloon 224 is contracted.

By the way, in FIG. 23, only the front side part of the antenna 228 is shown.

The other formations, operations and effects are the same as in the tenth embodiment.

Figure 25:
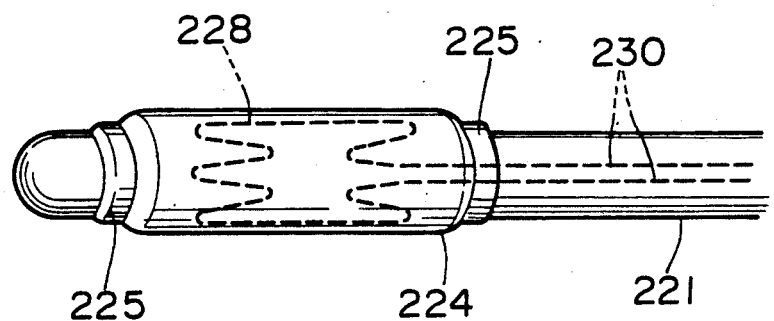
FIGS. 25 and 26 relate to the 12th embodiment of the present invention.
Figure 26:
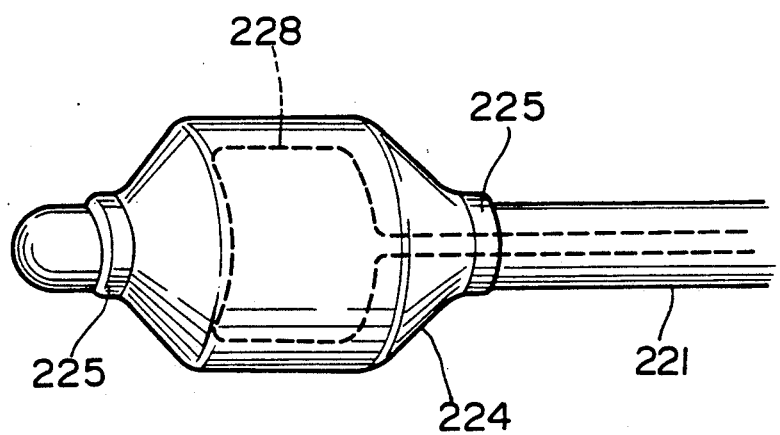

FIGS. 25 and 26 show the 12th embodiment of the present invention.

In this embodiment, as shown in FIG. 26, the antenna 228 is provided so as to be arranged in the form of a saddle on one side in the diametral direction when the balloon 224 is inflated. The same as in the 11th embodiment, as shown in FIG. 25, the above mentioned antenna 228 is flexible enough, for example, to be finely alternately bent and contracted when the balloon 224 is contracted.

This other formations, operations and effects are the same as in the 10th embodiment.

By the way, in the 10th to 12th embodiments, the antenna 228 may be fitted to the outer peripheral part or inner peripheral part of the balloon.

The shape of the antenna 228 is not limited to those shown in the above mentioned respective embodiments but may be wound to be in the form of a saddle on each side of the diametral direction or of a once wound loop.

By the way, the endoscope is not limited to a fiber scope but may be an electronic scope provided, as in the second embodiment, with a solid state imaging device as an imaging means and is not limited a flexible electronic scope but may be a rigid endoscope.

FIG. 27 to 30 show the 13th embodiment of the present invention.

Figure 29:
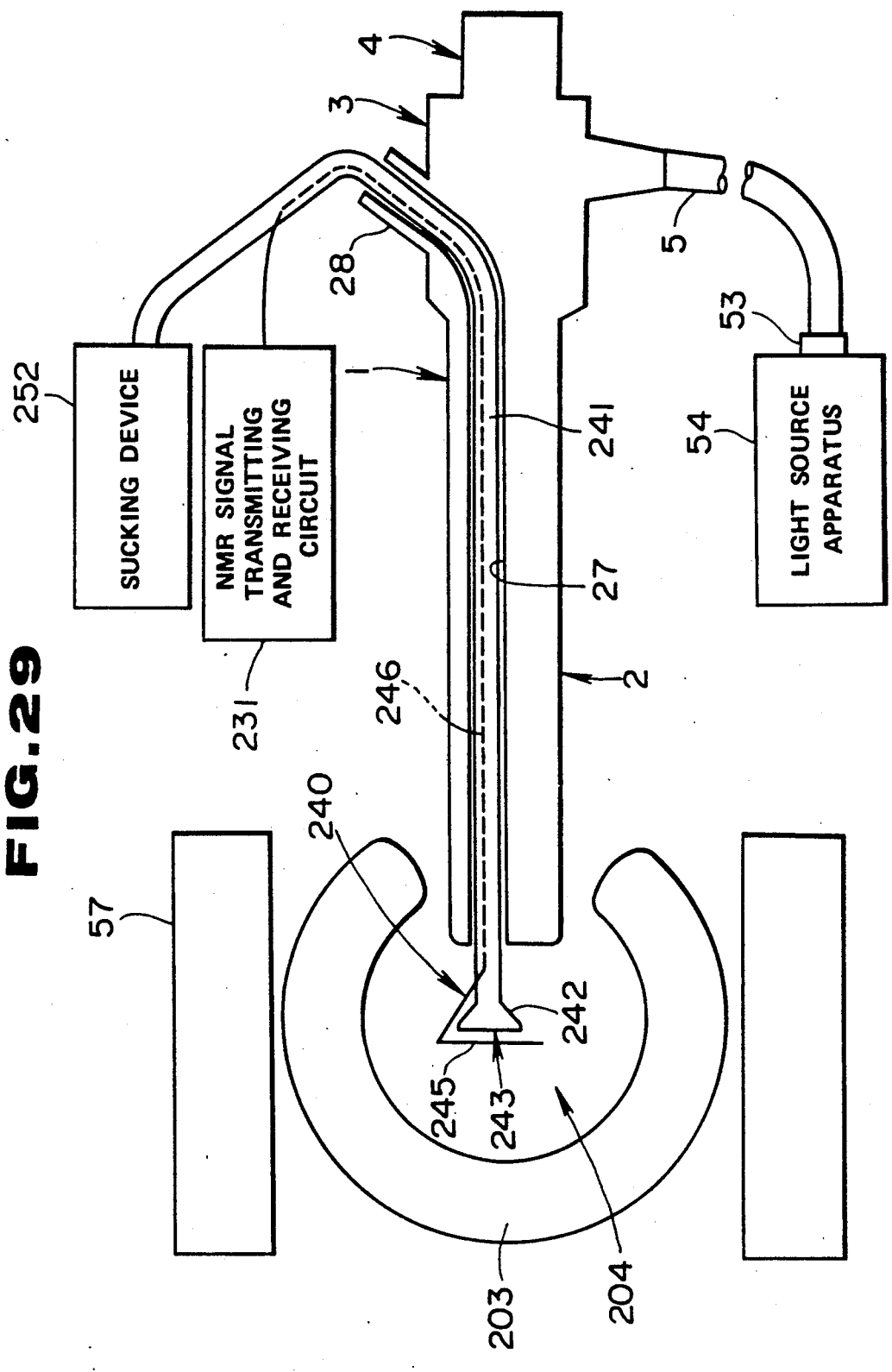

As shown in FIG. 29, the NMR metering antenna apparatus 240 of this embodiment is inserted through the treating tool channel 27 of the endoscope 1, for example, of the same straight viewing type as in the first embodiment and is inserted into the body cavity 204 of the examinee 203.

Figure 27:
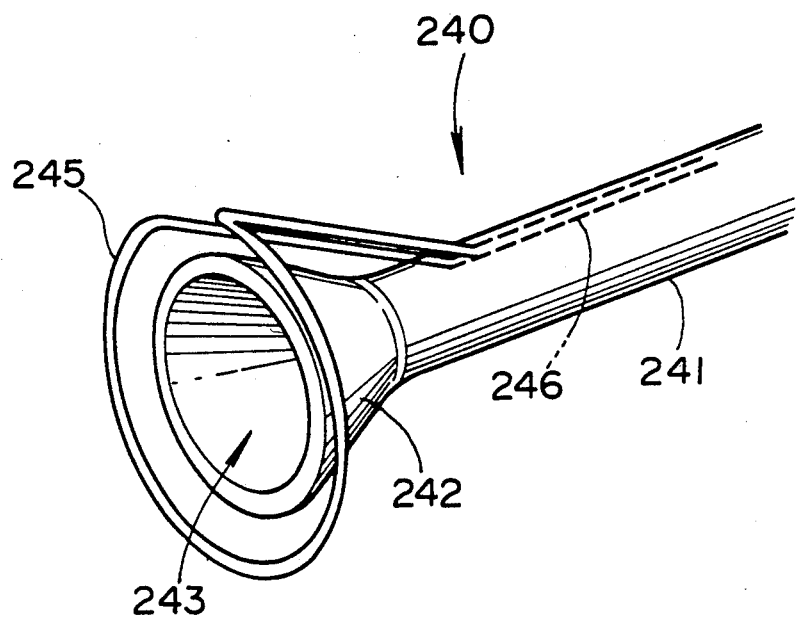
FIGS. 27 to 30 relate to the 13th embodiment of the present invention.
Figure 28:
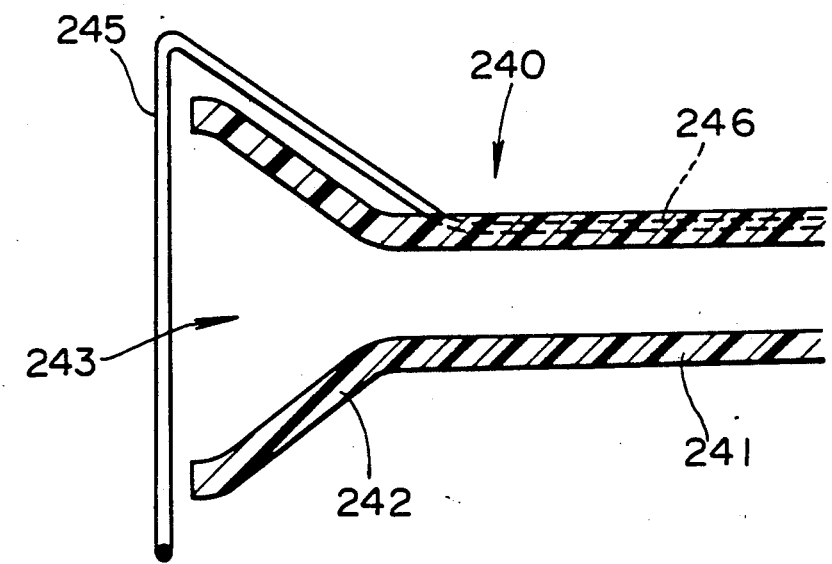
Figure 30:
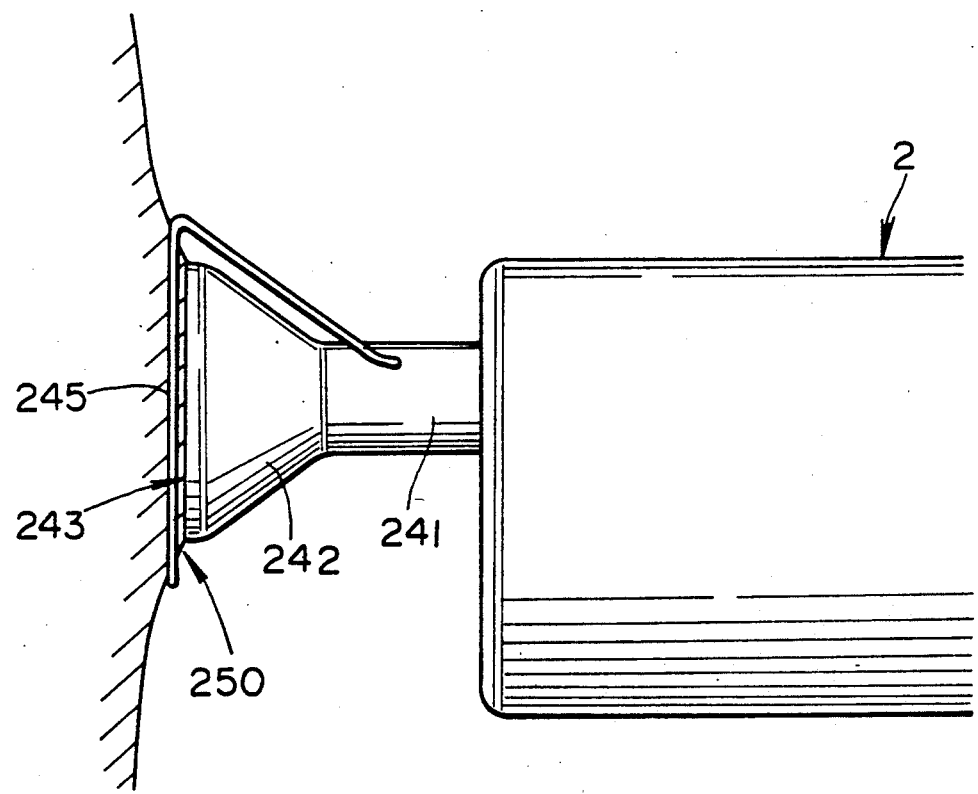

As shown in FIGS. 27 and 28, the NMR metering antenna apparatus 240 of this embodiment is provided with a sucking tube 241 which is, for example, flexible and is inserted into the above mentioned treating tool channel 27. The tip part of this sucking tube 241 is expanded in the diameter to be funnel-like and the opening at the tip of this funnel-like part 242 is a sucking port 243. A one-wind loop-like NMR metering antenna 245 having the axial direction, for example, of the above mentioned sucking tube 241 as a center is arranged rather in front of the above mentioned sucking port 243. By the way, the loop of this antenna 245 is formed to be somewhat larger than the above mentioned sucking port 243 and is arranged on the outer peripheral side of the above mentioned sucking port 243. The above mentioned antenna coil 245 is bent in at both ends rearward in the center axial direction and is connected in the rear of the above mentioned funnel-like part 242 to cables 246 embedded in the above mentioned sucking tube 241 as shown in FIG. 28. As shown in FIG. 29, the above mentioned cable 246 is connected on the base side to the NMR transmitting and receiving circuit 231 and the above mentioned sucking tube 241 is connected on the base side to the sucking device 252. As shown in FIG. 30, when the sucking port 243 of the above mentioned sucking tube 241 is opposed to a metering object position 250 within the body cavity 204 and the object position is sucked by the above mentioned sucking device 252, the above mentioned sucking port 243 will adhere to the above mentioned metering object position 250. As the above mentioned sucking port 243 adheres to the metering object position 250, the antenna coil 245 arranged rather in front of the above mentioned sucking port 243 will be closely contacted and fixed to the above mentioned metering object position.

By the way, such high frequency generating part 51 and NMR signal detecting part 52 as are shown in FIG. 4 are provided within the above mentioned NMR transmitting and receiving circuit 231 and the formation of the NMR metering means including the above mentioned antenna 228 is the same as is shown in FIG. 4.

The other formations are the same as in the first embodiment.

The operation of this embodiment formed as in the above shall be explained in the following.

As shown in FIG. 29, a static magnetic field is given to the examinee 203 by the NMR apparatus 57. The NMR metering antenna apparatus 240 is inserted into the treating tool channel 27 of the endoscope 1, the insertable part 2 of the endoscope 1 is inserted into the body cavity 204 through the mouth cavity or the like of the examinee 203, an illuminating light from the light source apparatus 54 is fed to the light guide of the endoscope 1 and the object image by this illuminating light is observed from the eyepiece part 4. In the case of metering NMR, as shown in FIG. 30, the above mentioned antenna apparatus 240 is projected on the tip side out of the treating tool channel 27 and the sucking port 243 of the sucking tube 241 is opposed to the metering object position within the body cavity 204. When the object position is sucked by the sucking device 252, the above mentioned sucking port 243 will adhere to the metering object position 250 and the antenna 245 arranged rather in front of the above mentioned sucking port 243 will be closely contacted and fixed to the above mentioned metering object position 250. In this state, a high frequency is transmitted to the above mentioned antenna 245 from the high frequency generating part and a high frequency signal is transmitted to the metering object position 250 from this antenna 245. When the NMR signal from the metering object position 250 is received by the above mentioned antenna 245 and is metered by the NMR signal detecting part 52, the physiological variation, for example, whether it is a cancer or not will be able to be detected.

Thus, in this embodiment, as the sucking port 243 of the sucking tube 241 as a sucking means is arranged in the rear of the NMR metering antenna 245, when the sucking port 243 is made to adhere to the metering object position 250, the above mentioned antenna 245 will be able to be easily fixed to the metering object position 250 within the body cavity 204.

By the way, in this embodiment, the loop of the antenna 245 may be formed to be somewhat smaller than the sucking port 243 and this antenna 245 may be arranged on the inner peripheral side of the above mentioned sucking port 243.

Figure 31:
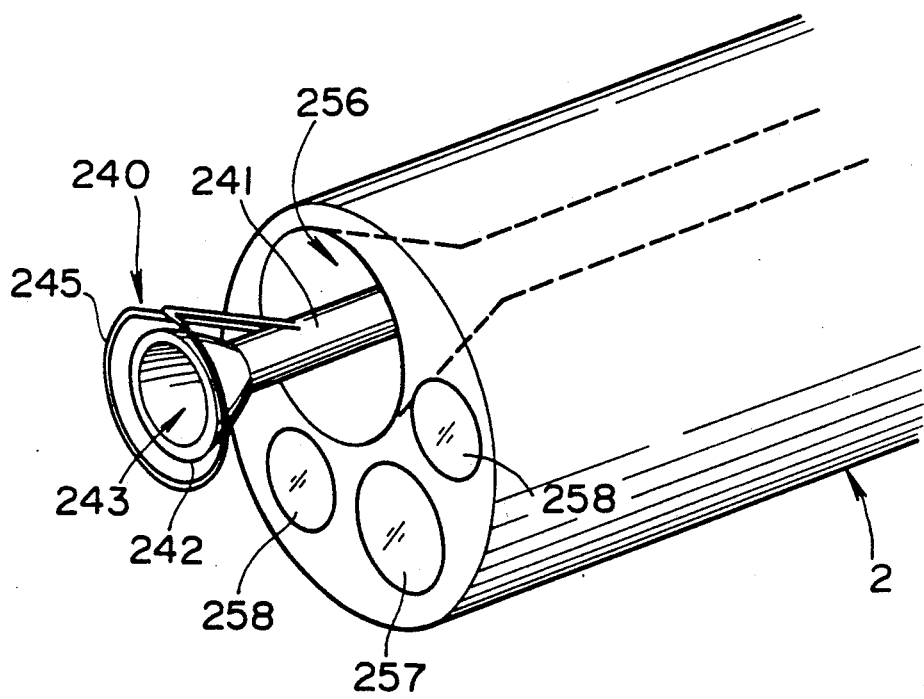
FIG. 31 is a perspective view showing an NMR metering antenna apparatus and the tip part of an insertable part of an endoscope in the 14th embodiment of the present invention.

FIG. 31 shows the 14th embodiment of the present invention.

In this embodiment, the tip part of the insertable part 2 of the endoscope 1 is provided with the funnel-like part 242 at the tip of the NMR metering antenna apparatus 240 of the 13th embodiment and a containing part 256 of the antenna 245. This containing part 256 is formed of a funnel-like recess somewhat larger than the above mentioned funnel-like part 242 and antenna 245. When the above mentioned funnel-like part 242 and antenna 245 are contained in the above mentioned containing part 256, the tip part of the antenna 245 will be arranged in the same plane as of the tip surface of the insertable part 2 of the endoscope 1 or inside the tip surface.

By the way, in the drawing, the reference numeral 257 represents an observing window and 258 represents an illuminating window.

The other formations are the same as of the 13th embodiment.

According to this embodiment, in case the insertable part of the endoscope 1 is to be inserted into the body cavity 204, when the tip part of the above mentioned antenna apparatus 240 is contained in the above mentioned containing part 256, the tip part of this antenna apparatus 240 will not project out of the tip surface of the insertable part 2 of the endoscope 1 and will be easy to insert.

The other operations and effects are the same as in the 13th embodiment

Figure 32:
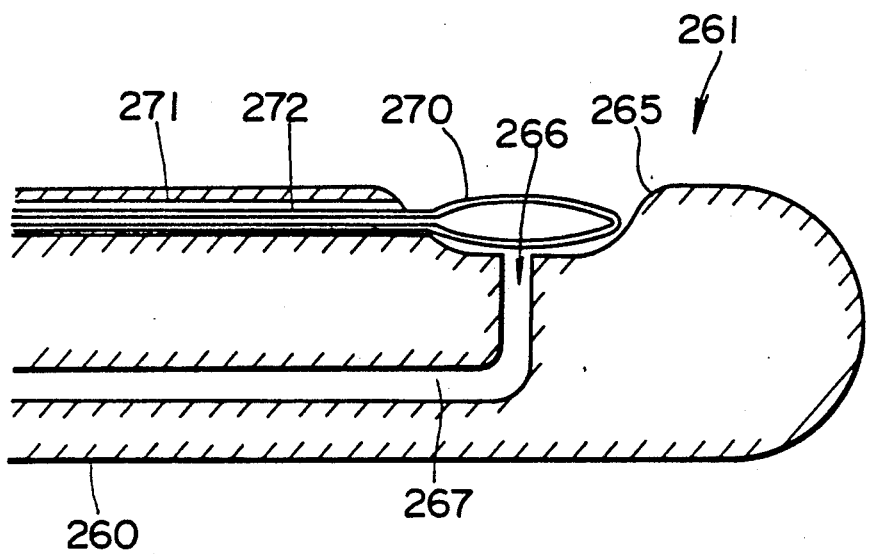
FIGS. 32 to 34 relate to the 15th embodiment.
Figure 33:
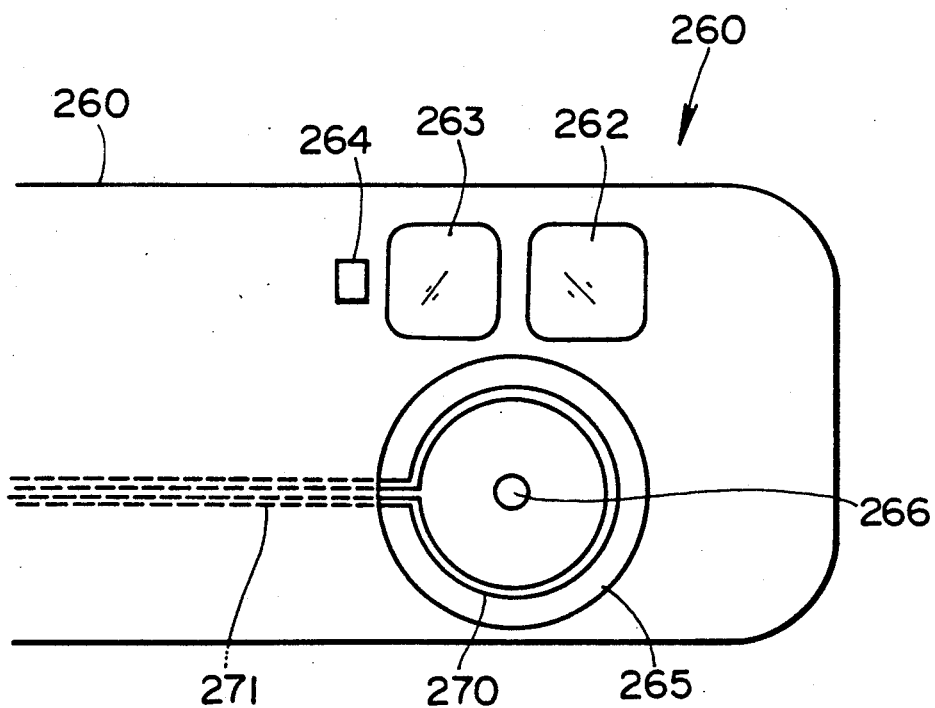
Figure 34:
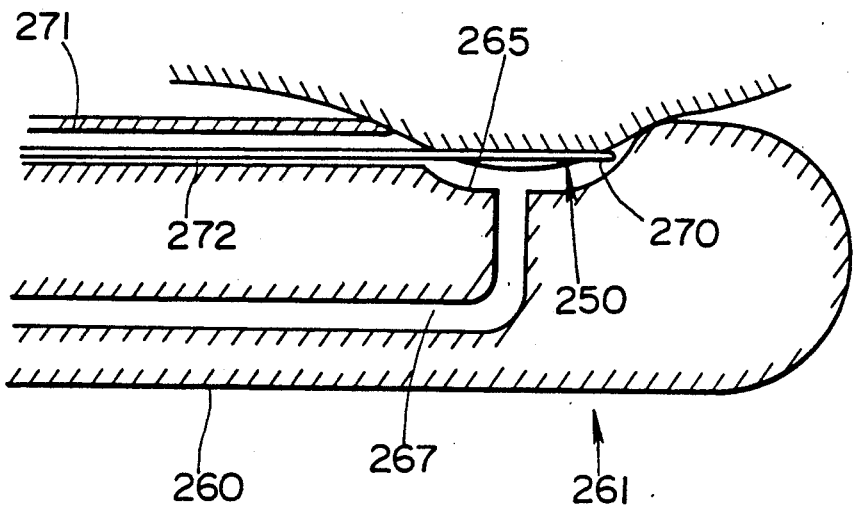

FIGS. 32 to 34 show the 15th embodiment of the present invention.

This embodiment is of an antenna apparatus to be used as combined with a side viewing type endoscope.

As shown in FIG. 33, the tip part 261 of the insertable part 260 of the side viewing type endoscope is provided with an illuminating window 262, observing window 263 and air and water feeding nozzle 264 opening toward this observing window 263 from the tip side on one side in the axial direction of the insertable part 260. A substantially circular groove part 265 is provided on the side of the above mentioned illuminating window 262 and observing window 263. As shown in FIG. 32, a sucking port 266 is provided substantially in the central part of the bottom of this groove part 265. A sucking channel 267 provided within the insertable part 260 communicates with this sucking port 266. This sucking channel 267 is connected on the base side to the sucking device 252. For example, a one-wind loop-like NMR metering antenna 270 concentric with this groove part 265 is arranged within the above mentioned groove part 265. This antenna 270 is connected at both ends to cables 272 inserted through a treating tool channel 271 provided within the above mentioned insertable part 260. The above mentioned cables 272 are connected on the base sides to the NMR signal transmitting and receiving circuit 231.

In this embodiment, as shown in FIG. 34, when the above mentioned groove part 265 provided on the side part of the tip part 261 is opposed to a metering object position 250 within the body cavity and the object position is sucked by the sucking device 252, the above mentioned groove part 265 will adhere to the metering object position 250 and the above mentioned antenna 270 will be closely contacted and fixed to the above mentioned metering object position 250.

The other formations, operations and effects are the same as in the 13th embodiment.

Figure 35:
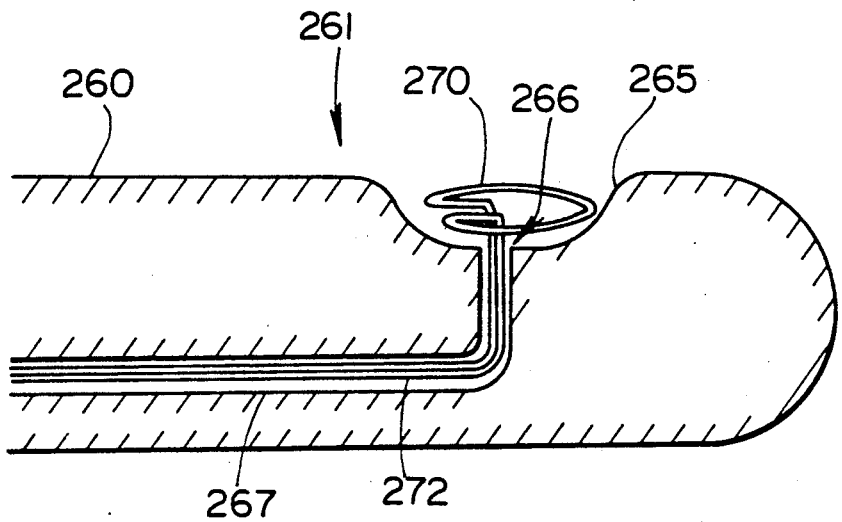
FIG. 35 is an explanatory view showing a longitudinal section of the tip part of an insertable part of an endoscope apparatus of a modification of the 15th embodiment of the present invention.
Figure 36:
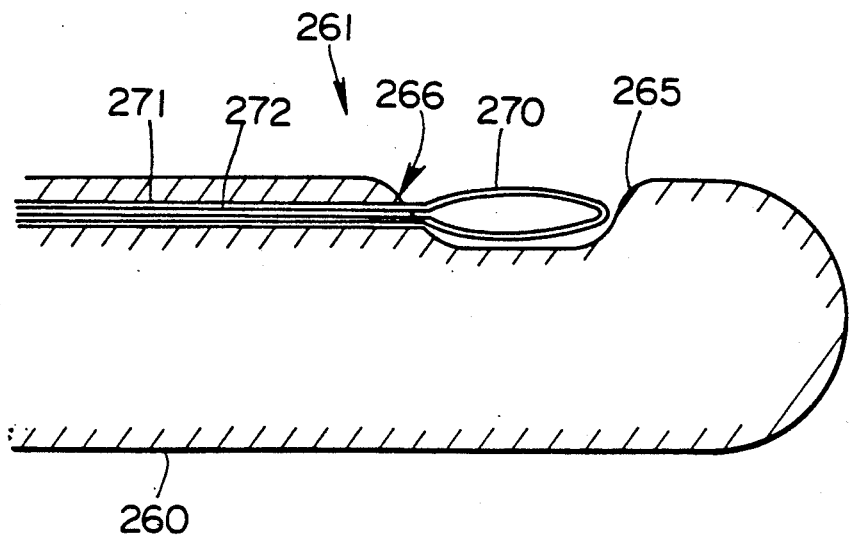
FIG. 36 is an explanatory view showing a longitudinal section of the tip part of an insertable part of an endoscope apparatus of another modification of the 15th embodiment of the present invention.

FIGS. 35 and 36 are longitudinally sectioned views of the tip parts of endoscope insertable parts relating to the modifications of the 15th embodiment of the present invention.

In the example shown in FIG. 35, an antenna 270 is bent at both ends to the central part side of the loop, is further bent to a sucking channel 267 side and is connected to cables 272 which are inserted through the sucking channel 267 so that the treating tool channel 271 may be unnecessary. The other formations are the same as in the 15th embodiment.

In the example shown in FIG. 36, the treating tool channel 271 is used also as a sucking channel and the opening to the groove part 265 of this treating tool channel 271 is made a sucking port 266 so that the sucking channel 267 may be unnecessary. The other formations are the same as in the 15th embodiment.

By the way, as in the fifth embodiment, a groove part continuing to the sucking port is provided in the tip part of a straight viewing type endoscope and an antenna may be arranged within this groove part. Also, such antenna apparatus 240 provided with sucking tube 241 and antenna 245 as in the 13th embodiment may be inserted through a treating tool channel of a side viewing type endoscope.

The shape of the antenna is not limited to be those shown in the 13th to 15th embodiments. For example, a saddle type antenna may be arranged on the side of the tip part of the insertable part of an endoscope.

By the way, the endoscope is not limited to be a fiber scope but may be an electronic scope provided with a solid state imaging device as an imaging means as in the second embodiment. It is not limited to be a flexible endoscope but may be a rigid endoscope.

Figure 38:
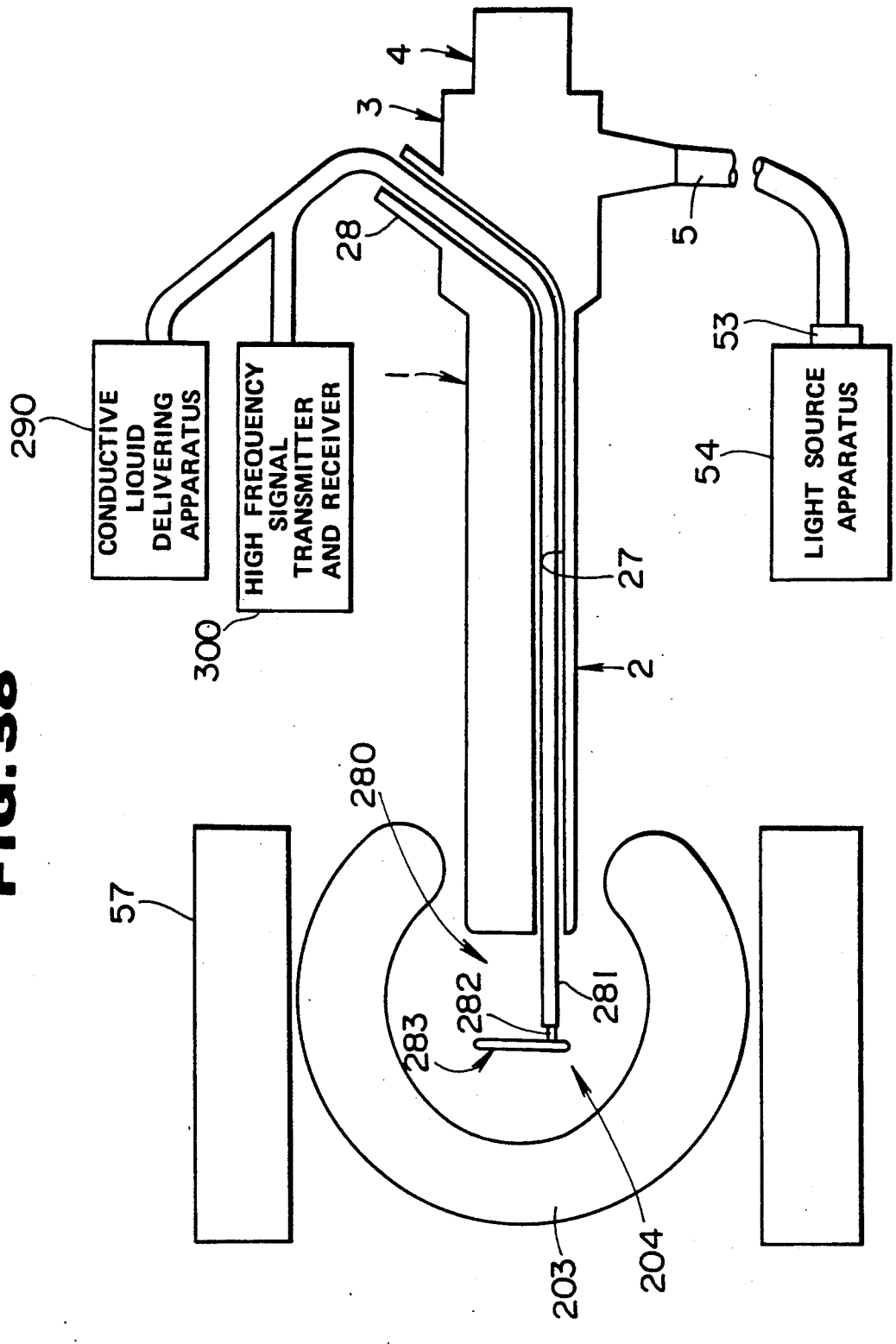

First 37 to 41 show the 16th embodiment of the present invention. As shown in FIG. 38, an NMR metering antenna apparatus 80 of this embodiment is inserted through a treating tool channel 27 of the same straight viewing type endoscope as, for example, of the fifth embodiment and is inserted into the body cavity 204 of the examinee 203.

By the way, in this embodiment, the insertable part 2 of the endoscope 1 is formed of such non-metal as plastics so that, even if the insertable part 2 is left inserted within the body cavity 204, the NMR apparatus for observation from outside the body will not be influenced.

As shown in FIG. 38 and 39, a NMR metering antenna apparatus 280 of this embodiment is provided with a protective tube 281 inserted through the above mentioned treating tool channel 27. An electrically insulative antenna tube 282 is inserted through this protective tube 281 and forms a circulating pipe line projecting out of the tip part 6 and protective tube 281 through the leading inlet 28 and treating tool channel 27 of the endoscope 1 from a conductive liquid delivering apparatus 290 provided outside the endoscope 1 and again returning to the above mentioned conductive liquid delivering apparatus 290 through the treating tool channel 27 and leading inlet 28 as shown in FIG. 37. A one-wind loop-like antenna part 283 is formed in the part projecting out of the tip part 6 and protective tube 281 of the above mentioned antenna tube 282. The center axis of the loop of this antenna part 283 is substantially parallel with the optical axis of the above mentioned objective lens system 86. By the way, the above mentioned antenna part 283 may be loop-like always or when the antenna tube 281 is filled with a liquid.

As shown in FIG. 37, the above mentioned conductive liquid delivering apparatus 290 is provided with a conductive liquid tank 291 interposed in the pipe line of the above mentioned antenna tube 282 and storing a conductive liquid 295 and a pump, for example, rotary pump for delivering a conductive liquid or air into the above mentioned antenna tube 288. The above mentioned conductive liquid tank 291 is provided on the inflow side of the above mentioned rotary pump 292. A switching cock 293 is interposed in the antenna tube 282 between this conductive liquid tank 291 and rotary pump 292 and an air inflow tube 294 is connected to the other inflow port of this switching cock 293 so that, by switching the above mentioned switching cock 293, the conductive liquid 295 or air stored in the above mentioned conductive liquid tank 291 may be switched to flow into the above mentioned rotary pump 292. By the way, the above mentioned conductive liquid 295 as a fluid having a conductivity is such liquid having a conductivity as, for example, such solution of an electrolyte as a saline solution.

As shown in FIG. 37, metallic tubes 301 are interposed in the part led out of the leading inlet 28 of the above mentioned antenna tube 282 between the endoscope 1 and the above mentioned conductive liquid delivering apparatus 290. Signal lines 302 are connected respectively to these metallic tube 301 and are connected to a high frequency signal transmitter and receiver 300 which transmits high frequencies (currents) for metering NMR to the above mentioned signal lines 302 and receives NMR signals from the above mentioned signal lines 302. The above mentioned high frequency signal transmitter and receiver 300 is provided with a switch 303 for switching on/off transmitting and receiving signals.

Figure 40:
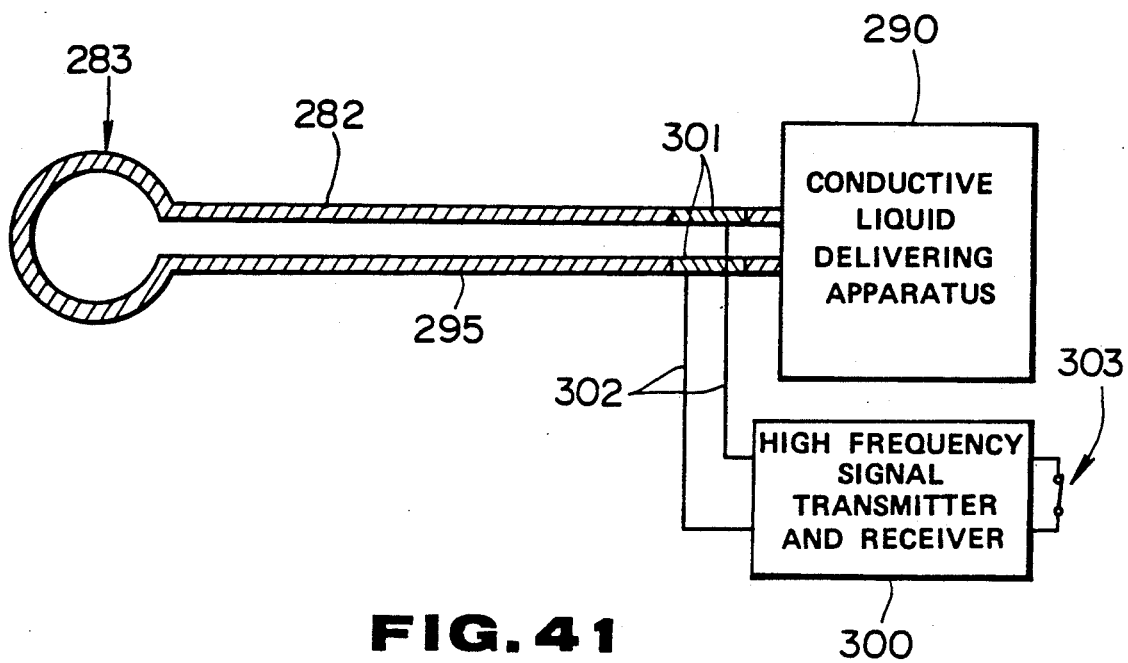

As shown in FIG. 40, in case the above mentioned antenna tube 282 is filled with the conductive liquid 295 by the above mentioned conductive liquid delivering apparatus 290, an NMR metering antenna will be formed of this conductive liquid 295. That is to say, the antenna tube 282 interior will have a conductivity and the antenna part 283 will function as an NMR metering antenna. This antenna part 283 is electrically connected to the high frequency signal transmitter and receiver 300 by the conductive liquid 295 within the antenna tube 282 and the signal lines.

Figure 41:
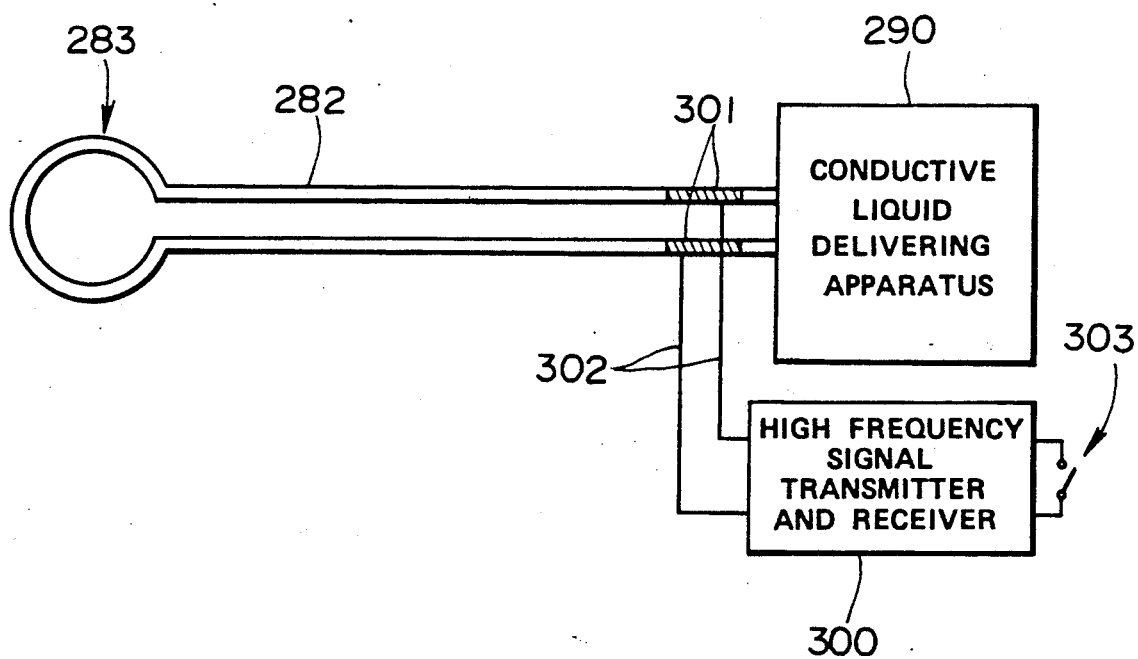

On the other hand, as shown in FIG. 41, when the switching cock 293 of the above mentioned conductive liquid delivering apparatus 290 is switched to the air side, the above mentioned antenna tube 282 is filled with air and the above mentioned conductive liquid 295 is drained, the conductivity of the antenna tube 282 will be lost and the antenna tube 282 will no longer function as an NMR metering antenna.

Now, in the case of metering NMR, the above mentioned antenna apparatus 280 is used as combined with an NMR apparatus 57 arranged to enclose the examinee as shown in FIG. 38. This NMR apparatus 57 is provided with such static magnetic field generating means as a permanent magnet, para-conductive magnet or super-conductive magnet. By the way, the above mentioned NMR apparatus 57 may be also an NMR imaging apparatus obtaining NMR images from outside.

By the way, such high frequency generating part 51 and NMR signal detecting part 52 as are shown in FIG. 4 are provided within the above mentioned high frequency signal transmitter and receiver 300. The formation of the NMR metering means including the above mentioned antenna 228 is the same as is shown in FIG. 4.

The other formations are the same as of the first embodiment.

The operation of this embodiment formed as in the above shall be explained in the following.

First of all, in the case of metering NMR from within a body by using the NMR metering antenna of this embodiment, as shown in FIG. 38, a static magnetic field is given to the examinee by the NMR apparatus 57. The NMR metering antenna apparatus 280 is inserted into the treating tool channel 27 of the endoscope 1 so that the antenna part 283 may be in lose contact with the tip surface of the tip part 6, the insertable part 2 of the endoscope 1 is inserted into the body cavity 204 through the mouth cavity or the like of the examinee 203, an illuminating light is fed from the light source apparatus 54 to the light guide of the endoscope 1 and the object image by this illuminating light is observed from the eyepiece part 4. Then, as shown in FIG. 40, the conductive liquid 295 is delivered into the antenna tube 282 by the conductive liquid delivering apparatus 290, the antenna tube is filled and the antenna part 283 is brought into contact with the metering object position. Then, the switch 303 of the high frequency signal transmitter and receiver 300 is switched on to deliver a high frequency from a high frequency generating part 51 to the antenna part 283 of the antenna tube 282 made to have a conductivity and function as an NMR metering antenna by the above mentioned conductive liquid 295 and a high frequency magnetic field is delivered to the metering object position from this antenna part 283. When the NMR signal from the metering object position is received by the above mentioned antenna part and is metered by the NMR signal detecting part 52, the physiological variation of the metering object position, for example, whether it is a cancer or not can be detected.

On the other hand, in the case of observing an NMR image from outside the body by using such NMR apparatus for obtaining an NMR image from outside the body as, for example, an NMR imaging apparatus, first of all, as shown in FIG. 41, the switch 303 of the above mentioned high frequency signal transmitter and receiver 300 is switched off to stop metering NMR from within the body. With the endoscope left inserted in the body cavity 204, the switching cock 293 of the above mentioned conductive liquid delivering apparatus 290 is switched to the air side, as shown in FIG. 41, the above mentioned antenna tube 282 is filled with air and the above mentioned conductive liquid 295 is drained. Then, the conductivity of the antenna tube 282 will be lost. Therefore, the magnetic field of the NMR apparatus for observation outside the body will not be disturbed by the above mentioned antenna apparatus 280 and a favorable NMR image from outside the body will be obtained.

Thus, in this embodiment, when the antenna tube 282 is filled with the conductive liquid 295, the NMR metering antenna will be formed and, when the conductive liquid 295 is drained out of the above mentioned antenna tube, the NMR apparatus for observation outside the body will not be influence.

Therefore, when the NMR metering antenna apparatus 280 of this embodiment is used, in case the NMR apparatus for observing from outside the body is used together, even if the endoscope 1 is not pulled out of the body cavity 204, a favorable NMR image from outside the body will be able to be obtained.

By the way, in this embodiment, an antenna 283 containing part may be provided in the tip part 6 of the endoscope 1.

Figure 42:
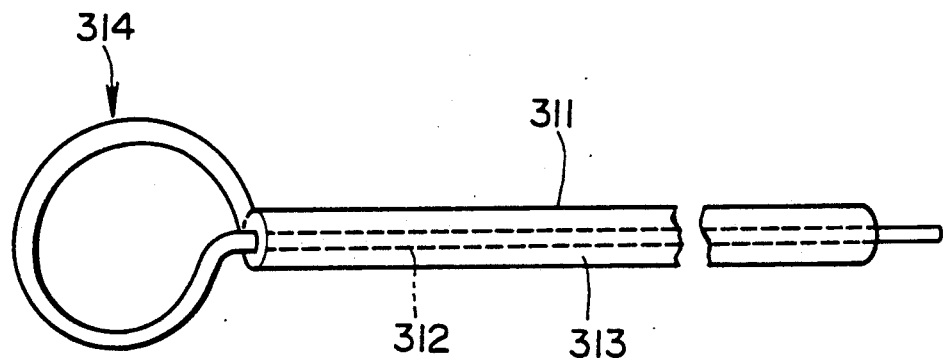
FIG. 42 is an explanatory view showing an antenna tube in the 17th embodiment of the present invention.

FIG. 42 shows the 17th embodiment of the present invention.

An antenna tube 311 of this embodiment is of a coaxial double structure having an inside pipe line 312 and outside pipe line 313 and a loop-like antenna part 314 made of an electrically insulative tube is formed in the tip part of this antenna tube 311 and communicates at one end with the above mentioned inside pipe line 312 and at the other end with the outside pipe line 313. The same as in the 16th embodiment, the above mentioned antenna tube 311 is connected on the base side to the conductive liquid delivering apparatus 290 and high frequency signal transmitter and receiver 300.

The other formations are the same as in the 16th embodiment.

According to this embodiment, as the part electrically connecting the antenna part 314 with the high frequency signal transmitter and receiver 300 is made coaxial, the loss will be little and the influence of the noise will be able to be made small.

The other operations and effects are the same as in the 16th embodiment.

By the way, in this embodiment, the central axial direction of the loop of the antenna part 314 is made to intersect substantially at right angles with the axial direction of the insertable part but, the same as in the 16th embodiment, it may be made to be substantially parallel with the axial direction of the insertable part.

By the way, in the 16th and 17th embodiments, the conductive fluid may be not only such liquid as a saline solution but also a conductive gel, ionized gas, such conductive powder as a metal powder or a mixture of these.

The shape of the antenna part may be not only one-wind loop-like but also saddle-like.

By the way, the endoscope may be not only a fiber scope but also an electronic scope or the like provided with a solid state imaging device as an imaging means and may be not only a flexible endoscope but also a rigid endoscope.

Figure 45:
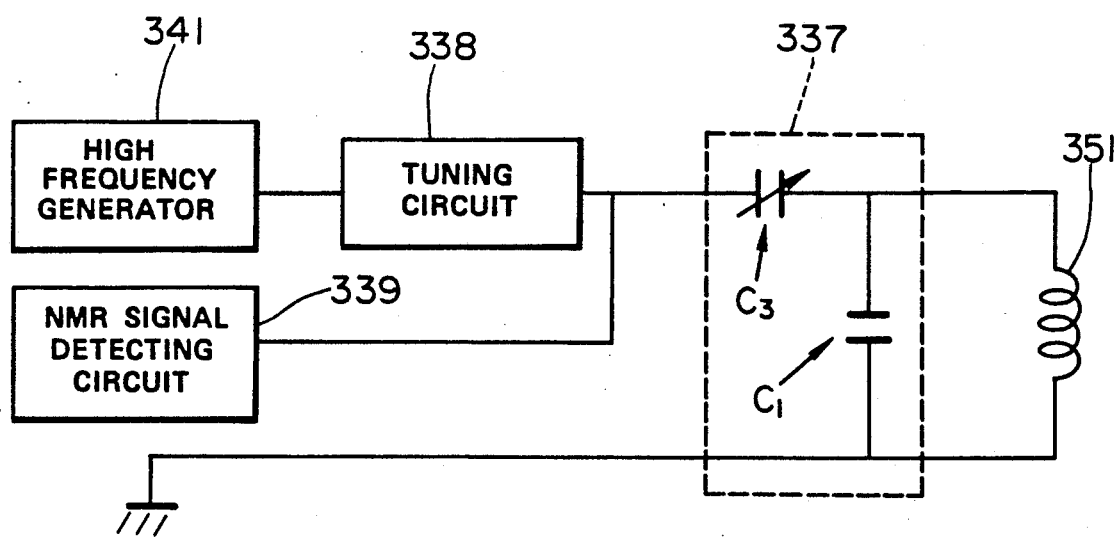
FIGS. 43 to 45 relate to the 18th embodiment of the present invention.
Figure 43:
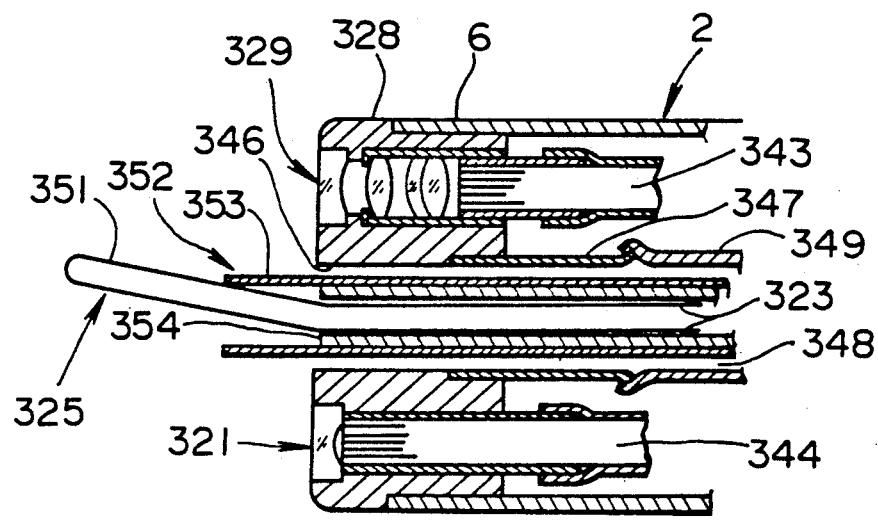
Figure 44:
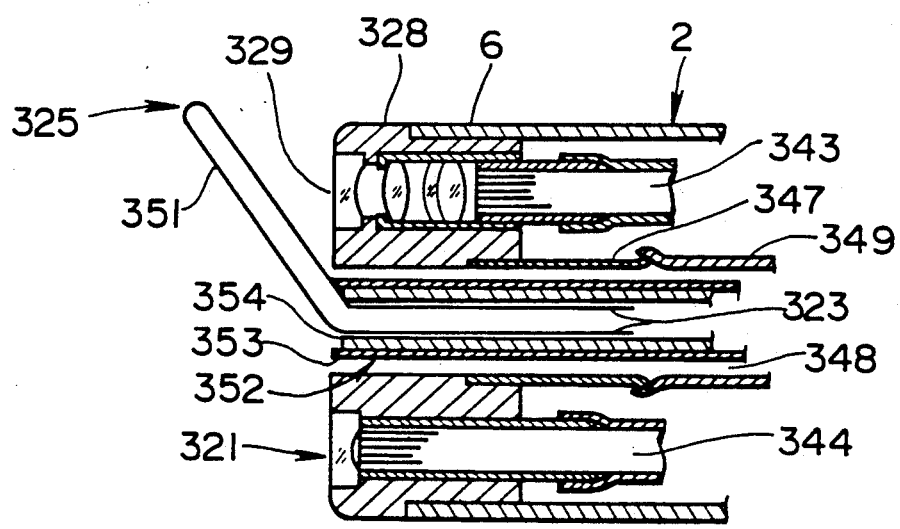

FIGS. 43 to 45 show the 18th embodiment of the present invention.

An NMR metering antenna 325 of this embodiment is inserted through a treating tool channel 348 provided within the insertable part 2 of an endoscope.

Such objective lens system 329 as can form observed images on the entrance end surface of an image guide 343 transmitting the observed images to an eyepiece part not illustrated and a light distributing lens system 321 whereby an illuminating light from a light source apparatus not illustrated can be fed to an observing position through a light guide 344 are provided on the front end surface of a tip part body 328 provided in the tip part 6 of the above mentioned insertable part 2.

Furthermore, a forceps channel through hole 346 parallel with the lengthwise direction of the insertable part 2 is provided in the central part of the tip part body 328. A treating tool channel tube 349 forming a treating tool channel 348 and communicating with a leading inlet not illustrated provided in an operating part not illustrated is connected to the rear part of this forceps channel through hole 346.

A detecting tube 352 as a shape converting means in which an NMR metering antenna 351 is inserted is inserted into the above mentioned treating tool channel 348 through the above mentioned leading inlet so that the front end may be positioned near the tip surface of the tip part body 328. In this detecting tube 352, a flexible inner tube 354 is slidably inserted through a flexible outer tube 353. The NMR metering antenna 351 formed to be U-like of an elastic member bent by a plastic deformation in the direction at right angles with the lengthwise direction of the insertable part 2 and having a sufficient elasticity is energized and contained in the inner tube 354 and is connected at both ends to signal lines 323 inserted through the inner tube 354.

The above mentioned NMR metering antenna 351 is energized by the tip edge part of the inner periphery of the outer tube 353 and the inner peripheral surface of the inner tube 354 so that, as in FIG. 43, when the outer tube 353 is slid to project on the tip side, the antenna 1 will be energized and the angle made with the lengthwise direction of the insertable part 2 will become gradually smaller but, on the contrary, when the outer tube 353 is retreated to the tip surface of the tip part body 328 to release the energizing force, the angle made with the lengthwise direction of the insertable part 2 will become larger to bend the antenna 351.

Therefore, when the outer tube 353 is projected or retreated, the direction of the high frequency magnetic field generated by the antenna will be able to be changed and the detecting direction can be selected.

The NMR metering means including the above mentioned antenna 351 is formed as shown, for example, in FIG. 45.

That is to say, a condenser part 337 provided, for example, in the tip part body 328 is connected to the above mentioned antenna 351. A high frequency generated from a high frequency generator 341 provided, for example, in a light source apparatus and tuned to a resonant frequency corresponding to the metered object nucleus kind in a tuning circuit 338 is transmitted to the above mentioned antenna 351 through the above mentioned condenser part 337 and a high frequency magnetic field is output to the living body from this antenna 351. A condenser $C_1$ in parallel with the above mentioned antenna 351 and a variable condenser $C_3$ in series with the above mentioned antenna 351 are contained in the above mentioned condenser part 337. A matching circuit matching the impedances on the above mentioned antenna 351 side and high frequency generator 341 side is formed of these condensers $C_1$ and $C_3$.

In this embodiment, the above mentioned antenna 351 transmits and receives signals. The NMR signal from the living body is received by the above mentioned antenna 351 and is input into the NMR signal detecting circuit 339 through the above mentioned condenser part 337. Such information (NMR parameter) as a releasing time ($T_1$ and $T_2$) is obtained in this NMR signal detecting circuit 339.

By the way, in this embodiment, the detecting tube 352 is inserted through the treating tool channel 348 but may be fixed within the insertable part 2.

According to this embodiment, the detecting direction of the NMR metering antenna 351 can be changed without requiring any special apparatus.

As explained above, according to this embodiment, by bending the NMR metering antenna, the direction of the high frequency magnetic field generated by the antenna and the detecting direction can be made to coincide with each other and a quick diagnosis can be made.

Figure 46:
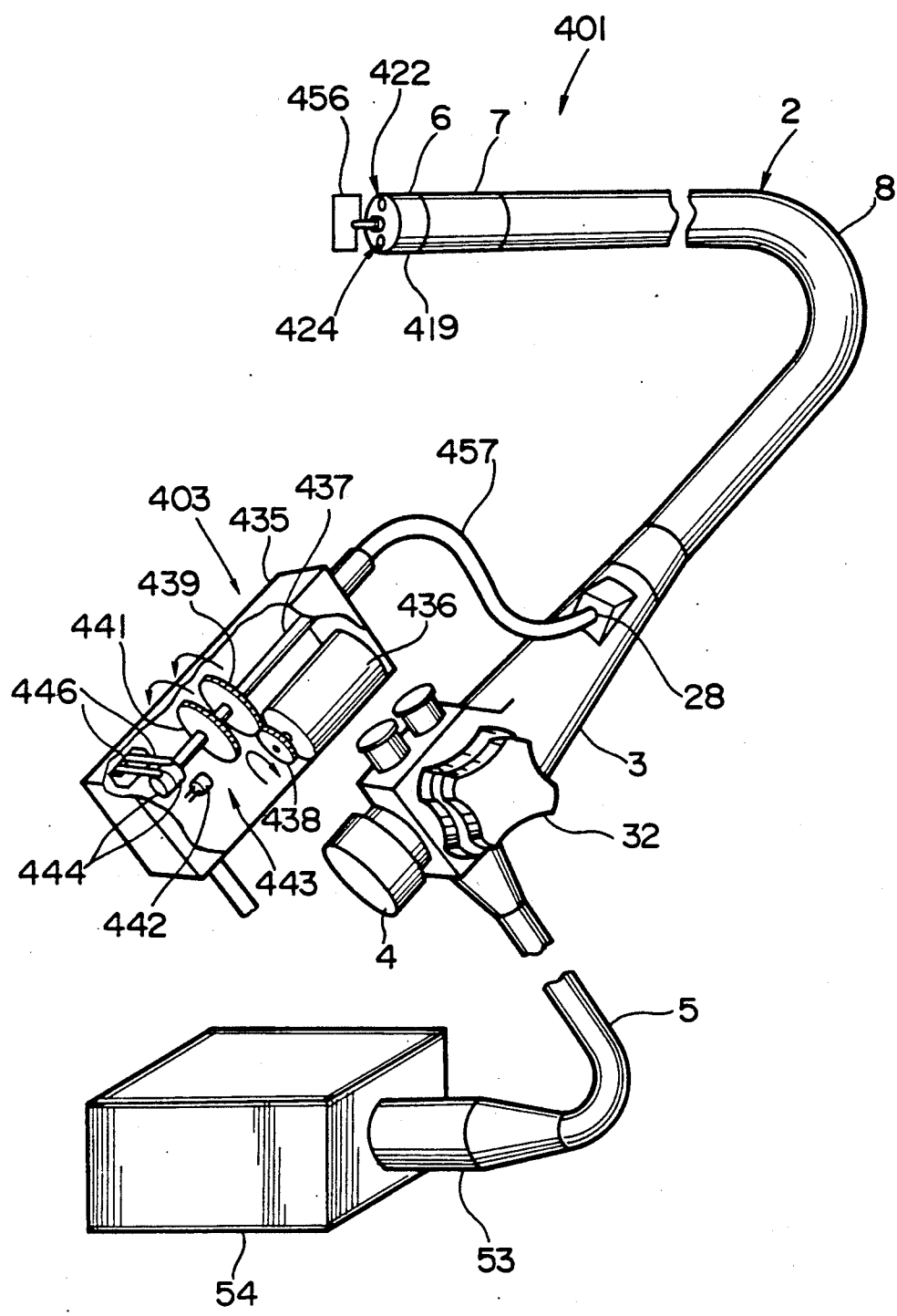
FIGS. 46 and 47 relate to the 19th embodiment of the present invention.
Figure 47:
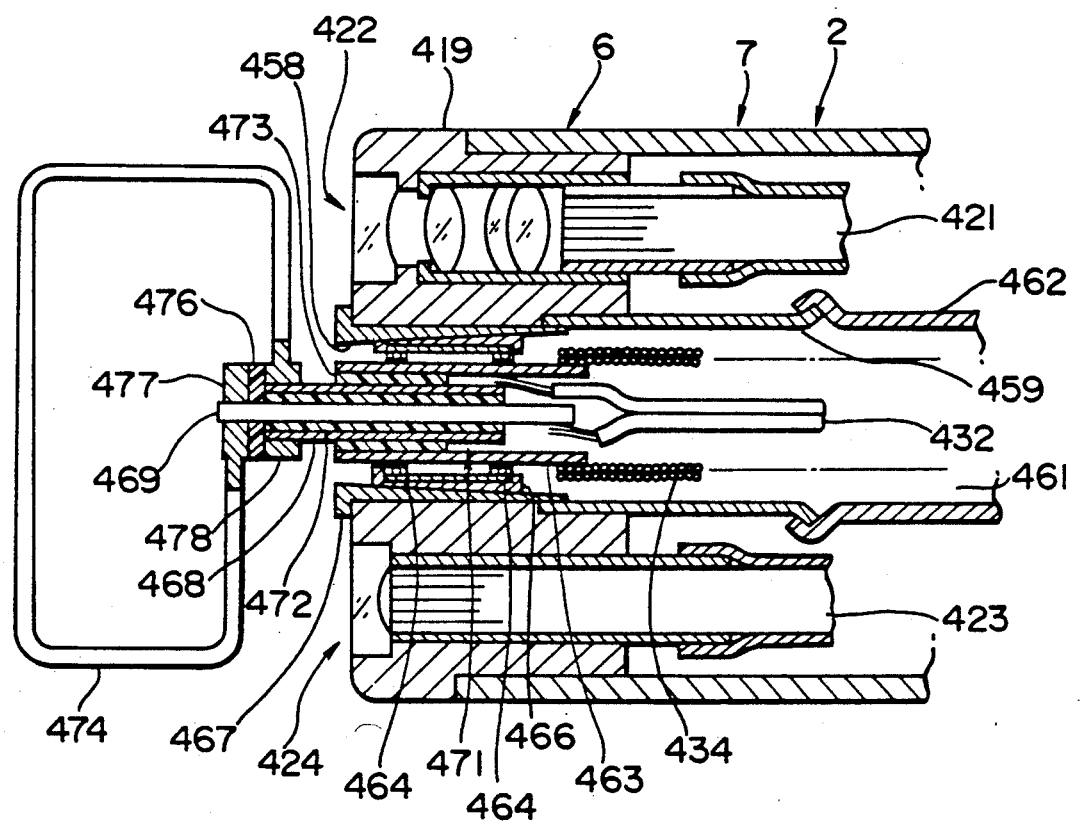

FIGS. 46 and 47 show the 19th embodiment of the present invention.

An endoscope 401 in this embodiment is of substantially the same formation as of the endoscope 1 of the first embodiment.

In this embodiment, as shown in FIG. 46, a flexible tube 457 in which a driving shaft 434 driving a later described NMR metering antenna 456 is inserted into the leading inlet 28 of the treating tool channel and an antenna driving part 403 provided with a motor 436 as a driving means is connected to the rear end of this flexible tube 457.

As shown in FIG. 47, the tip part 6 of the endoscope 401 is provided with a substantially columnar tip part body 419 made of such rigid material as a metal.

Such objective lens system 422 as can form an object image on the entrance end surface of an image guide 421 transmitting an observed image to the eyepiece part 4 and a light distributing lens system 424 which can feed an illuminating light from the above mentioned light source apparatus 54 to an observed position through a light guide 423 are provided on the front end surface of the above mentioned tip part body 419.

A treating tool channel through hole 458 parallel with the lengthwise direction of the insertable part 2 is further provided in the central part of the tip part body 419. A treating tool channel tube 462 forming a treating tool channel 461 and communicating with the above mentioned leading inlet 28 in connected to the rear part of this treating tool channel through hole 458 through a connecting pipe 459.

A driving shaft 434 through which signal lines 432 are inserted and which can transmit a torque is inserted through the above mentioned treating tool channel through hole 458. A cylindrical rotary member 463 is connected to the tip part of this driving shaft 434. Ball bearings 464 are externally fitted to the outer periphery of this rotary member 463. A fixing member 466 having a tapered part becoming smaller in the diameter toward the tip side is further provided on the outer periphery of the roller bearings 464.

On the other hand, a tubular fixing tube 467 having a flange surface contacting the tip surface of the tip part body 419 in the front part and projecting partly out of the tip surface is inserted in the treating tool channel through hole 458. A tapered part having the same taper angle as of the tapered part of the above mentioned fixing member 466 is provided on the inner peripheral surface of this fixing tube 467 so as to fix the rotary member 463 to the tip part body 419 through the fixing member 466 and fixing tube 467.

An electrically connecting member 471 formed of a core member 469 provided so as to project at both ends out of the end surfaces of a tubular member 468 through an insulative member 472 within the tubular member 468 is fixed by an insulative member 473 so that the front part side tubular member 468 and core member 469 may project out of the tip surface of the tip part body 419 within the above mentioned rotary member 463. The signal lines 432 are electrically connected respectively to the rear parts of the tubular member 468 and core member 469.

In the front part of the above mentioned tip part body 419, an NMR metering antenna 474 formed to be substantially square is connected at both ends respectively to the outer peripheries of two cylindrical engaging parts 477 and 478 provided as overlapped with an insulative member interposed between them. The core member 469 is inserted in the inside diameter part of one engaging part 477 and the tubular member 468 is inserted in the other engaging part 478.

When the above mentioned antenna 474 is removably engaged with the electrically connecting member 471 by an engaging means not illustrated, the tubular member 468, the engaging part 477 which is one end part of the antenna 474, the core member 469 and the engaging part 478 which is the other end part of the antenna 471 will conduct.

As shown in FIG. 46, a motor 436 as a driving means having a reduction gear is provided within a case 435 forming the above mentioned coil driving part 403. This motor 436 is connected to the above mentioned driving shaft 434 through gears 438 and 439 to drive a connecting shaft 437 provided parallelly with the rotary center of the motor 436.

The connecting shaft 437 is provided with an encoder 443 formed of a rotary disc 441 and photosensor 442.

The signal lines 432 connected to the NMR metering antenna 474 are connected to electric contacts 444 provided on the rear end part of the connecting shaft 437. These electric contacts 444 are insulated by interposing an insulative member between the core member and the tubular member forming its outer periphery and are made to contact brushes 446 fixed to the case 435. These brushes 446 are connected to the tuning circuit 338 and NMR signal detecting circuit 339 provided within the light source apparatus 54 through the operating part 4 and signal lines not illustrated. The above mentioned tuning circuit 338 is connected to the output end of the high frequency generator 341.

By the way, the formation of the NMR metering means is the same as is shown in FIG. 45.

The operation of this embodiment formed as in the above shall be explained.

The NMR metering antenna 474 is removed from the driving shaft, the driving shaft is inserted through the leading inlet 28, is inserted through the treating tool channel 461, the fixing tube 467 is inserted into the treating tool channel through hole 458 in the position in which the electrically connecting member 471 projects in the front part out of the tip part body 419 and the rotary member 463 is fixed to the tip part body 419. The NMR metering antenna 474 is engaged with the electrically connecting member 471 projected out of the tip part 6. Then, the insertable part 2 of the endoscope 401 provided with the NMR metering antenna 474 is inserted through the mouth cavity or the like of the examinee.

As explained above, according to this embodiment, there are effects that, as the NMR metering antenna is made rotatable, the direction of the high frequency magnetic field generated by the antenna and the detecting direction can be easily made to coincide with each other and a quick diagnosis can be made.

Also, according to this embodiment, as the driving shaft for driving the NMR metering antenna is removably provided, the driving shaft may be removed in case NMR is not metered. It can be used in the form corresponding to the use.

Figure 48:
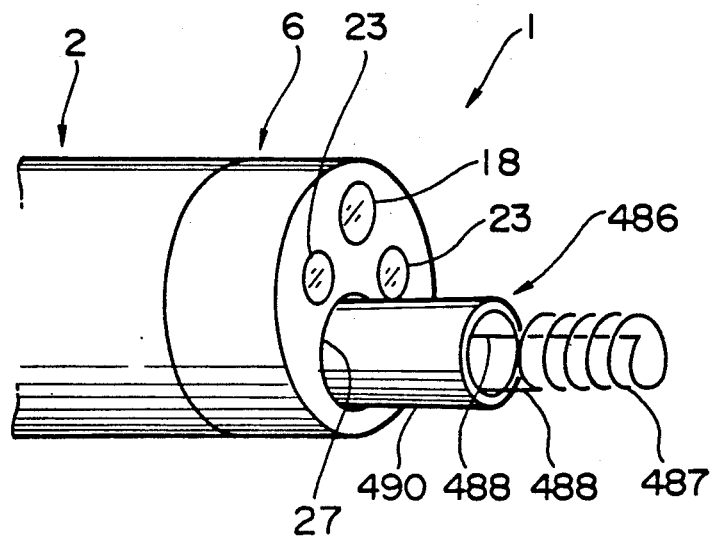
FIG. 48 is a perspective view showing the tip part of an insertable part of an endoscope apparatus in the 20th embodiment of the present invention.

FIG. 48 shows the 20th embodiment of the, present invention.

As shown in FIG. 48, an NMR metering antenna apparatus 486 of this embodiment is inserted through the treating tool channel 27 provided in the same endoscope 1 as, for example, of the first embodiment.

A flexible guide tube 490 forming the antenna apparatus 486 is inserted through a leading inlet 28 provided on the side part of the operating part 3 of the above mentioned endoscope 1 and is projected at the tip out of the front end surface of the tip part 6 through the insertable part 2.

An antenna 487 is provided in front of the tip part of the above mentioned guide tube 490 and is connected to signal lines 488 inserted through the guide tube 490. These signal lines 488 are extended from the operating part 3 and are connected to the tuning circuit 338 and NMR signal detecting circuit 339 through the condenser part 337. Further, the tuning circuit 338 is connected to the output end of the high frequency generator 341.

By the way, the formation of the NMR metering means is the same as is shown in FIG. 45.

In this embodiment, the above mentioned antenna 487 is formed to be of a plurality of spiral winds, has a resiliency and is coated with an insulative member.

In the case of metering NMR with the antenna apparatus 486 of this embodiment, the upper layer part of a stomach wall or the like is observed with the observing optical system. For example, in case an abnormal position as a detected position is discovered on the front surface in the inserting direction, the curving operation knob 32 provided in the operating part 3 is operated, the guide tube 490 inserted through the treating tool channel 27 is directed to the abnormal position and is projected out of the tip part 6 and the antenna 487 is pushed against the abnormal position. The antenna 487 is energized by being pushed and is supported and fixed in the abnormal position by the energizing force produced then. In this state, a high frequency is transmitted to the above mentioned antenna 487 through the high frequency generator 341, tuning circuit 338 and condenser part 337 and a high frequency magnetic field is output to the abnormal position from this antenna 487. By the way, it is desirable that the direction of this high frequency magnetic field intersects at right angles with the direction of the static magnetic field. When the NMR signal from the abnormal position is received by the above mentioned antenna 487 and is metered by the NMR signal detecting circuit 339, the physio-logical variation of the abnormal position, for example, whether it is a cancer or not will be able to be detected.

By the way, in this embodiment, the NMR metering antenna apparatus 486 is used as inserted through the treating tool channel 27 of the endoscope 1 but the NMR metering antenna apparatus 486 alone may be used.

Figure 49:
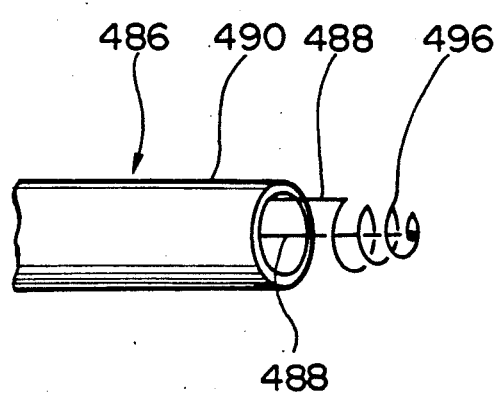
FIG. 49 is a perspective view showing the tip part of an NMR metering antenna apparatus in the 21st embodiment of the present invention.

FIG. 49 shows the 21st embodiment of the present invention.

Signal lines 488 connected to a tuning circuit and NMR signal detecting circuit not illustrated are inserted through a flexible tubular guide tube 490 forming an NMR metering antenna apparatus 486. An NMR metering antenna coil 496 wound in a plurality of winds so as to be larger in the outside diameter rearward from the tip side and formed to have a resiliency is connected at both ends to the tips of the signal lines 488 projected out of the tip of the guide tube 490.

According to this embodiment, the outside diameter of the spiral on the side in contact with an abnormal position is so small that the energizing forces produced by pushing the antenna will concentrate on the spiral of the above mentioned small outside diameter, therefore the pushing force per units area will increase and a more positive support will be able to be made.

By the way, the NMR metering antenna apparatus 486 of this embodiment may be used as inserted through the treating tool channel 27 of the endoscope 1 or may be used alone.

The other formations, operations and effects are the same as in the 20th embodiment.

As explained above, according to the 20th and 21st embodiments, there are effects that, as the NMR metering antenna to be inserted into a body cavity through an endoscope is made resilient, the antenna will be supported and fixed in a detected position within the body cavity and an accurate metering will be able to be easily made.

By the way, in the 20th and 21st embodiments, the antenna may not be inserted through the guide tube.

Figure 50:
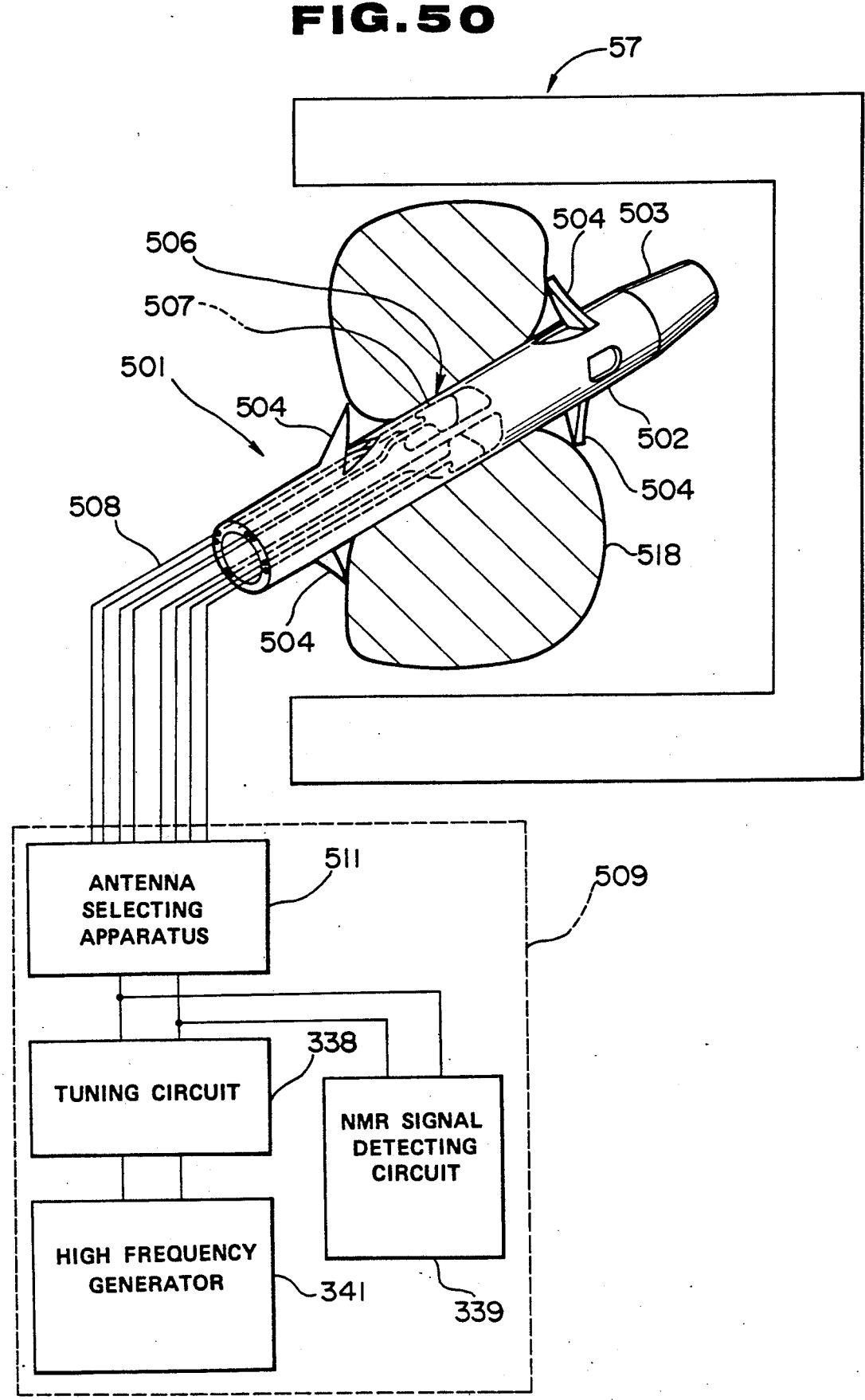
FIGS. 50 and 51 relate to the 22nd embodiment of the present invention.
Figure 51:
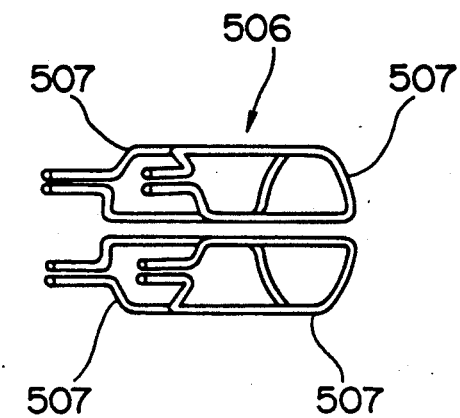

Further, the endoscope is not limited to a fiber scope but may be an electronic scope or the like wherein a solid state imaging device is provided as an imaging means as in the second embodiment. Also it is not limited to a flexible endoscope but may be a rigid endoscope. FIG. 50 and 51 show the 22nd embodiment of the present invention.

In this embodiment, an NMR metering antenna is provided in a medical retained tube.

As shown in FIG. 50, a retained tube 501 is formed of a hollow flexible tubular tube body 502, a tip part 503 formed to be tapered so as to be smaller in the diameter forward to make it easy to insert this tube body 502 on one end side, removal preventing flaps 504 in the parts adjacent to this tip part 503 and near the rear end part and an NMR metering antenna 506 provided within the tube body 502.

As shown in FIG. 51, the above mentioned NMR metering antenna 506 is formed, for example, of four saddle-like coils 507 so that the detection in four diametral directions may be possible. Each coil 507 is connected at both ends respectively to signal lines 508 inserted through the thick part within the tube body 502 and the signal lines 508 are extended out of the rear part of the tube body 502. The extended signal lines 508 are connected to an antenna selecting apparatus 511 provided within the NMR metering apparatus 509 so that the coils 507 may be selected in conformity with the detecting direction.

The above mentioned antenna selecting apparatus 511 is connected to tuning circuit 338 and NMR signal detecting circuit 339. Further, the tuning circuit 338 is connected to the output end of a high frequency generator 341.

The formation of the NMR metering means including the above mentioned coil 507 is the same as is shown in FIG. 45.

The above mentioned retained tube 501 is to be led into a body through a treating tool channel, for example, of the endoscope 1 of the first embodiment or an ordinary endoscope.

The operation of this embodiment formed as in the above shall be explained in the following.

As in FIG. 50, such body to be examined as a narrowed gall tube part made by such tumor as a cancer is placed within a static magnetic field produced by the NMR apparatus 57.

The retained tube 501 is held with such treating tool as a holding forceps not illustrated, is passed, for example, through a treating tool channel of the endoscope and is inserted and retained within the body 518 to be examined. Thus, the narrowed gall tube part can be pushed to expand and a bile can be drained. Further, in order to diagnose the examined body 518, a high frequency is transmitted to the coil 507 in a desired direction, for example, by a switching switch provided in the antenna selecting apparatus 511 through the high frequency generator 341, tuning circuit 338 and condenser part 337 and a high frequency magnetic field is output to the examined body 518 from this coil 507. By the way, it is desirable that the direction of this high frequency magnetic field intersects at right angles with the direction of the static magnetic field. The NMR signal from the examined body 518 is received by the above mentioned coil 507 and is metered by the NMR signal detecting circuit 339. When this operation is made by switching the coil 507 in turn by the antenna selecting apparatus 511, the physiological variation of the examined body 518 around the retained tube 501, for example, whether it is a cancer or not will be able to be detected.

Further, as the retained tube 501 is retained within the examined body 518, the variation with the lapse of time of the examined body can be known.

Also, as the NMR metering antenna 506 is provided within the retained tube 501, the outside diameter of the endoscope in which the retained tube 501 is inserted can be made smaller.

Figure 52:
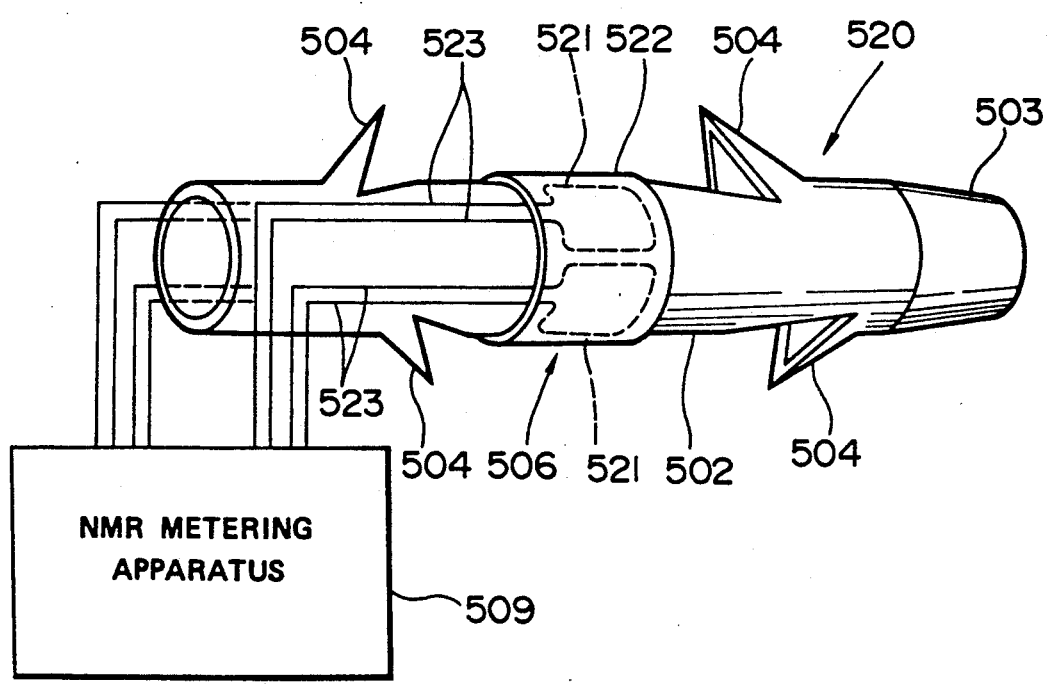
FIG. 52 is an explanatory view showing a retained tube in the 23rd embodiment of the present invention.

FIG. 52 shows the 23rd embodiment of the present invention. A flexible printed substrate 522 having, for example, four saddle-like coils 521 printed in the peripheral direction is pasted on the outer peripheral surface of the tube body 502 of the retained tube 520 to form the NMR metering antenna 506. The above mentioned coil 521 forms high frequency magnetic fields at both ends and is connected to the NMR metering apparatus 509 through signal lines 523.

According to this embodiment, the flexible printed substrate 522 on which the coils 521 are printed may be pasted on the conventional retained tube 520 in response to the use. Thus the manufacturing cost of the retained tube 520 can be made low.

The other formations, operations and effects are the same as in the 22nd embodiment.

As explained above, according to the 22nd and 23rd embodiments, as the medical tube for preventing the closure of the narrow part and the NMR metering antenna are made integral, the outside diameter of the endoscope can be made as small as possible and the pain given to the patient can be reduced.

Figure 53:
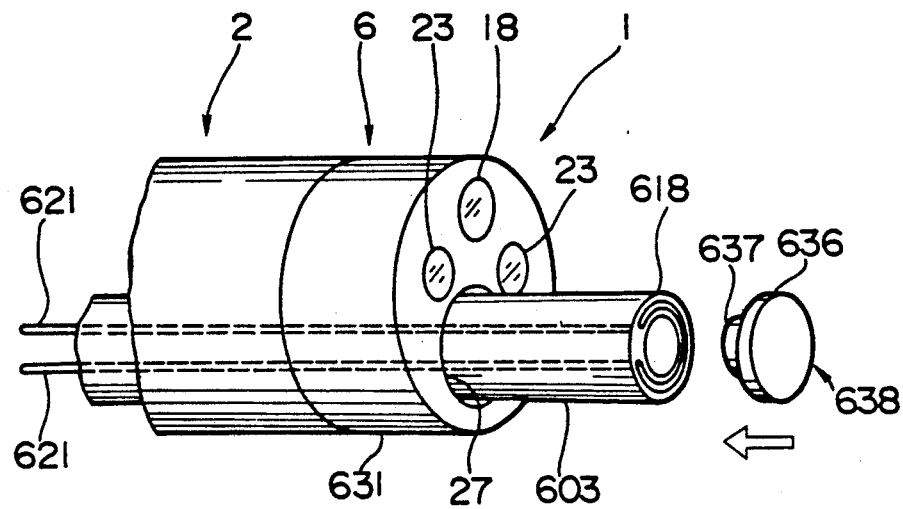
Figure 54:
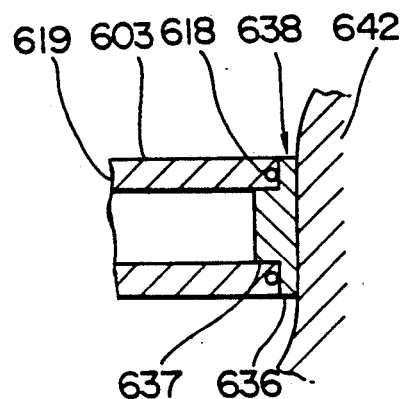

FIG. 53 to 55 show the 24th embodiment of the present invention.

As shown in FIG. 55, an NMR metering antenna apparatus 601 of this embodiment is formed of a flexible hollow elongate catheter 601 to be inserted through a treating tool channel 27 of an endoscope 602 and an NMR metering apparatus.

The above mentioned endoscope 602 is of substantially the same formation as of the endoscope 1 of the first embodiment but a ferromagnetic metal is used for the operating part 3. An index 610 is provided in the course of the flexible part 8 of the insertable part 2.

A flexible hollow elongate catheter 603 is inserted into the leading inlet 28 provided on the side part of the operating part 3 of the above mentioned endoscope 602 so as to project at the tip out of the front end surface of the tip part 6 through the insertable part 2.

A loop-like NMR metering antenna 618 is provided in the tip part of the above mentioned catheter 603 and is connected at both ends to signal lines 621 extended out of the catheter 603 and connected to the tuning circuit 338 and NMR signal detecting circuit 339 provided within the NMR metering apparatus 605. Further, the tuning circuit 338 is connected to the output end of the high frequency generator 341 and the NMR signal detecting circuit 339 is connected to an operation displaying system 626.

In the case of metering NMR, the above mentioned endoscope 602 is used as combined with the NMR apparatus 57 arranged to enclose the examinee 56 mounted on the bed 55. This NMR apparatus 57 is provided with such means generating a static magnetic field as a permanent magnet, para-conductive magnet or super-conductive magnet.

By the way, when the operating part 3 made of a ferromagnetic metal is within a fixed distance, it will be attracted by a static magnetic field produced by the NMR apparatus 57. So as to prevent it, the above mentioned index 610 indicates the limit of the approach of the operating part 3 to the NMR apparatus 57.

As shown in FIG. 53, the tip part 6 of the endoscope 602 is provided with a substantially columnar tip part body 631 made of such rigid material as a metal.

An objective lens system 18 which can form an observed image on the entrance end surface of an image guide of fibers not illustrated transmitting the observed image to the eyepiece part 4, a light distributing lens systems 23 which can feed the illuminating light from the above mentioned light source apparatus 54 to the observed position through a light guide of fibers not illustrated and an air and water feeding nozzle not illustrated are provided on the front end surface of the above mentioned tip part body 631.

Further, a treating tool channel 27 communicating with the above mentioned leading inlet 28 is provided within the tip part body 631 so as to insert the above mentioned catheter 603 through it. A loop-like NMR metering antenna 618 is annularly provided concentrically with the catheter 603 in the tip part of this catheter 603 and is connected at both ends to signal lines 621 embedded in the lengthwise direction within the thick part 619 of the catheter 603. A lid 638 as a supporting member formed of a flange part 636 of the same outside diameter as of the catheter 603 and small diameter part 637 having an outside diameter which can be fitted to the inside diameter of the catheter 603 is provided at the front end of the catheter 603.

As shown in FIG. 54, when the above mentioned lid 638 is fitted to the front end of the catheter 603 and is contacted with an abnormal position 642 as an examined object, the thickness in the lengthwise direction of the flange part 636, that is, the gap between the antenna 618 and abnormal position 642 will be able to be kept constant.

The formation of the NMR metering means including the above mentioned antenna 618 is the same as is shown in FIG. 45.

By the way, in this embodiment, a predetermined operation is made on the basis of an NMR parameter by an operation displaying system 626 connected to the above mentioned NMR signal detecting circuit and the results of this operation are displayed in a monitor or the like.

The operation of this embodiment formed as in the above shall be explained in the following.

As in FIG. 55, the examinee 56 is mounted on the bed 55 and a static magnetic field is given to the examine 56 by the NMR apparatus 57. In this state, the insertable part 2 of the endoscope 602 through which the catheter 603 provided with the NMR metering antenna 618 is inserted is inserted through the mouth cavity or the like of the examinee 56, an illuminating light is fed to the light guide of fibers not illustrated of the endoscope 602 and, for example, the upper layer of a stomach wall the like is observed by an observing optical system comprising the objective lens system 18 image guide of fibers not illustrated and eyepiece part 4. In case an abnormal position 642 is discovered, the curving operation knob 36 provided on the operating part 3 is operated so that the abnormal position 642 may come to the front surface of the tip part 6, the catheter 603 is projected and the tip surface of the lid 638 is pushed against the abnormal position 642. The gap between the antenna 618 and abnormal position can be kept constant with the lid 638 provided between the antenna 618 and abnormal position 642. Further, the catheter 603 is stably supported by contacting the tip surface of the lid 638 with the abnormal position 642. In this state, a high frequency is transmitted to the above mentioned antenna 618 through the high frequency generator 341, tuning circuit 338 and condenser part 337 and a high frequency magnetic field is output to the abnormal position 642 from this antenna 618. By the way, it is desirable that the direction of this high frequency magnetic field intersects at right angles with the direction of the static magnetic field. When the NMR signal from the abnormal position 642 is received by the above mentioned antenna 618 and is metered by the NMR signal detecting circuit 339 and the obtained data are displayed by the operation displaying system 626, the physiological variation of the abnormal position 642, for example, whether it is a cancer or not can be detected.

By the way, by varying the thickness of the flange part 636 of the lid 638 a gap conforming to the shape of any abnormal position can be st.

In this embodiment, the catheter 630 is used as inserted through the treating tool channel 27 but may be used alone.

FIGS. 56 (A) and (B) show a modification of the 24th embodiment.

A loop-like MNR metering antenna 618 is annularly provided concentrically with the catheter 603 in the tip part of the flexible hollow elongate catheter 603 and is connected at both ends to signal lines not illustrated embedded in the lengthwise direction within the thick part 619 of the catheter 603.

A lid 648 as a supporting member formed of a flange part 644 of the same outside diameter as of the catheter 603, a small diameter part 646 having an outside diameter which can be fitted to the inside diameter of the catheter 603 and a plurality of projections 647 annularly provided on the outer peripheral side of the tip surface of the flange part 644 is provided at the front end of the catheter 603.

When the above mentioned lid 648 is fitted to the front end of the catheter 603 and is contacted with the abnormal position 642, the thickness of the flange part 644, that is, the gap between the antenna 618 and abnormal position 642 can be kept constant.

FIGS. 57 (A) and (B) show another modification of the 24th embodiment.

A loop-like MNR metering antenna 618 is annularly provided concentrically with the catheter 603 in the tip part of the flexible hollow elongate catheter 603 and is connected at both ens to signal lines not illustrated embedded in the lengthwise direction within the thick part 619 of the catheter 603.

A lid 654 as a supporting member formed of a flange part 651 of the same outside diameter as of the catheter 603, a small diameter part 652 having an outside diameter which can be fitted to the inside diameter of the catheter 603 and a funel-like hollow part 653 expanding in the diameter toward the tip side is provided at the front end of the catheter 603. This lid 654 can suck the abnormal position 642 contacting the tip surface of the lid 654 through the catheter 603 with a sucking apparatus not illustrated.

When the above mentioned lid 654 is fitted to the front end of the catheter 603 and is contacted with the abnormal position 642, the thickness in the lengthwise direction of the flange part 651, that is, the gap between the antenna 618 and abnormal position 642 can be kept constant. Further, by sucking the abnormal position 642 with a sucking apparatus not illustrated, the catheter 603 can be stably supported.

FIG. 58 shows the 25th embodiment of the present invention.

An NMR metering antenna apparatus 691 of this embodiment is formed of a flexible elongate catheter 656, a balloon 657 as supporting member provided in the tip part of the catheter 656, an NMR metering apparatus 605, a water feeding and draining pump 658, a pressure sensing setting apparatus 659 and a water feeding and draining pump controlling apparatus 651.

The above mentioned catheter 656 is provided within with a tube 660 passing from the tip part to the rear end part. Further in the tip part of the catheter 656 an antenna 662 formed to be like a loop concentric with the catheter 656 is provided as connected at both ends to signal lines 663 inserted through the catheter 656.

The above mentioned balloon 657 is formed of an expansible material so as to cover the tip part of the catheter 656.

The above mentioned signal lines 663 are extended out of the rear end of the catheter 656 and are connected to the above mentioned NMR metering apparatus 605.

The sucking port 664 of the above mentioned water feeding and draining pump 658 can suck water within a water tank 666. The tank 666 is connected on the delivery side 667 to a tube 660 extended out of the rear end part of the catheter 656 so as to be able to feed a liquid into the balloon 657.

The above mentioned pressure sensing setting apparatus 659 is connected to a pressure sensor 668 provided on the above mentioned delivery side 667 so as to be able to sense the pressure within the balloon 657. The water feeding and draining pump controlling apparatus 661 can drive the water feeding and draining pump 658 with the pressure information obtained from the above mentioned pressure sensing setting apparatus 659.

The operation of this embodiment formed as in the above shall be explained in the following.

Water is fed by the water feeding and draining pump 658 into the balloon 657 provided in the tip part of the catheter 656. When the pressure within the balloon 657 becomes a fixed pressure Pa, the drive of the water feeding and draining pump 658 will be stopped. The balloon 657 is contacted with the abnormal position 642. While gradually pressing the balloon, the rising pressure is read by the pressure sensing setting apparatus 659. The balloon 657 of the pressure Pa in advance is pressed. The pressure Pb in the case that the gap between the antenna 662 and abnormal position 642 becomes a predetermine value is measured. When the pressure rises to this pressure Pb, the pressing will be stopped.

The pressure within the balloon 657 is metered by the pressure sensing setting apparatus 659 and the catheter 656 is supported so that the pressure Pb may be fixed.

In case the gap between the antenna 662 and abnormal position 642 becomes large, the pressure within the balloon 657 will reduce. Therefore, the balloon is pressed again so that the pressure may become Pb. An the contrary, in case the gap between the antenna 662 and abnormal position 642 becomes small, the pressure within the balloon 657 will rise. Therefore, the balloon is pulled off so that the pressure may become Pb. Thus, while the gap between the antenna 662 and abnormal position 642 is kept constant, the abnormal position 642 can be examined by the NMR metering apparatus 605.

According to this embodiment, by pressing the abnormal position 642 with the balloon 657, the catheter 656 can be supported and, by keeping the pressure within the balloon 657 constant, the gap between the antenna 662 and abnormal position 642 can be made constant.

Figure 59:
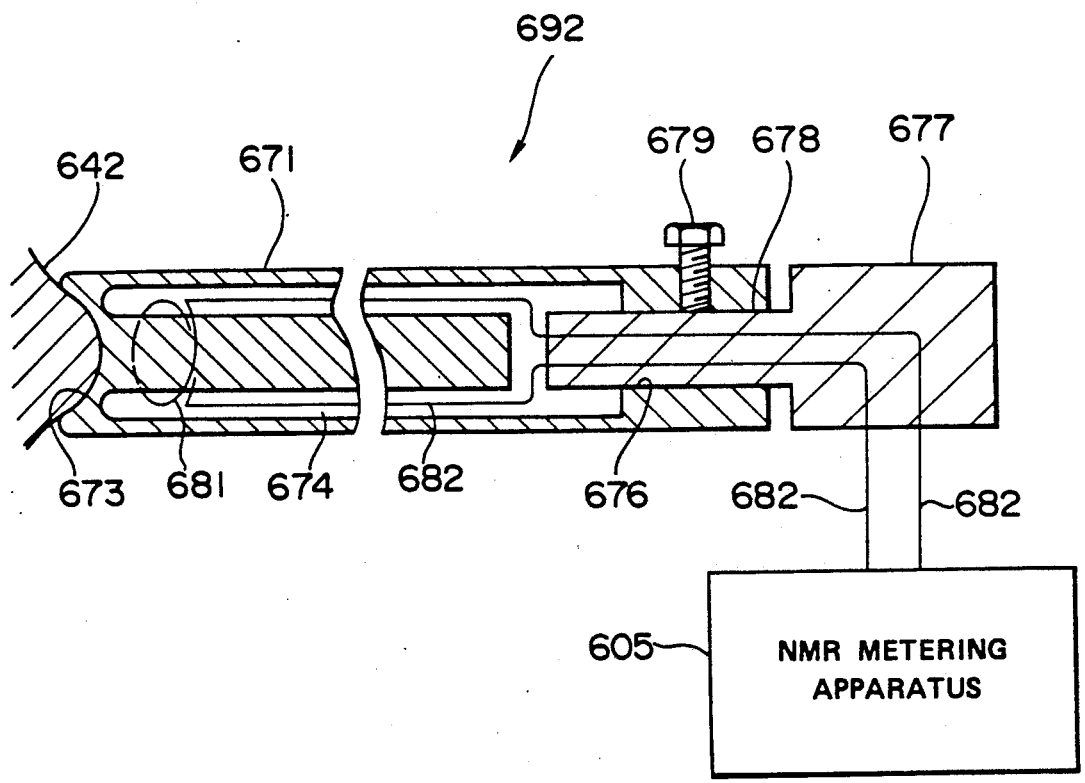
FIG. 59 is an explanatory view showing the formation of an NMR metering antenna apparatus in the 26th embodiment of the present invention.

FIG. 59 shows the 26th embodiment of the present invention.

An NMR metering antenna apparatus 692 of this embodiment is formed of a catheter 671 as a supporting member and an NMR metering apparatus 605.

The above mentioned catheter 671 is elongate columnar and has a concave 673 formed on the front end surface so as to contact an abnormal position 642. A peripheral space 674 concentric with the lengthwise direction center of the catheter 671 is provided toward the rear part from a little rear of the tip surface of the catheter 671.

A hollow part 676 communicating with the above mentioned peripheral space 674 is provided in the rear part of the above mentioned catheter 671 and a small diameter part 678 extended to the front part of an operating part 677 is slidably inserted in the above mentioned hollow part 676. A fixing screw 679 is screwed in the diameteral direction in the rear part of the above mentioned catheter 671 so as to press and fix the above mentioned small diameter part 678.

A loop-like antenna 681 is provided in the front part of the above mentioned peripheral space 674 and is connected at both ends to signal lines 682 inserted through the operating part 677, small diameter part 678 and peripheral space 674. These signal lines 682 are to support the antenna 681 with the operating part 677. By sliding the catheter 671 with respect to the operating part 677, the gap between the abnormal position 642 contacting the concave 673 and the antenna 681 can be fixed.

The above mentioned signal lines 682 are extended out of the operating part 677 and are connected to the NMR metering apparatus 605.

By the way, the catheter 671 may be formed of a flexible material or a rigid material.

According to this embodiment, the position of the antenna 681 can be moved while the abnormal position 642 and catheter 671 are in contact with each other.

The other formations, operations and effects are the same as in the 24th embodiment.

As explained above, according to the 24th to 26th embodiments, there are effects that an NMR metering antenna can be easily supported by forming a fixed gap from an examined body within a body cavity and an accurate metering can be made.

By the way, in the 24th to 26th embodiments, the antenna apparatus may be inserted through the treating tool channel of a side viewing type or oblique viewing type endoscope or the NMR metering antenna apparatus alone may be inserted into a body cavity.

Further, the endoscope is not limited to a fiber scope but may be on electronic scope or the like provided with a solid state imaging device as an imaging means and also is not limited to a flexible endoscope but may be a rigid endoscope.

In this invention, it is apparent that different working modes in a wide range can be formed on the basis of this invention without deviating from the spirit and scope of the invention. This invention is not restricted by its specific working modes except being limited by the appended claims.

What is claimed is:

1. An NMR metering endoscope apparatus comprising:

an endoscope having an elongate insertable part having a tip part insertable into a body and including an observing window and an illuminating window formed in the tip part, an observing means having a visual field for observing an object to be imaged by receiving light from the object entering through said observing window, an illuminating light output means for emitting an illuminating light through said illuminating window and a hollow channel formed within said insertable part including an opening in said tip part; and an NMR (nuclear magnetic resonance) metering probe having a signal transmitting member insertable into said body through said channel and opening, said probe being connected at one end to an NMR metering apparatus so as to transmit high frequency signals therefrom, and a loop-like antenna connected to the other end of said signal transmitting member to receive said high frequency signals, said loop-like antenna being projected out of the opening of said channel formed in said tip part to radiate said high frequency signals and generate a high frequency magnetic field such that a high frequency magnetic field is delivered to a body part by said antenna so as to cause NMR radiation from said body part, said NMR radiation being received by said antenna and delivered to said NMR metering apparatus to enable detection of a physiological variation in the body part, whereby location of the source of the radiation within said body can be visually identified by use of said observing means of said endoscope.

2. An NMR metering endoscope apparatus comprising:

an endoscope having an elongate insertable part having a tip part insertable into a body and including an observing window and an illuminating window formed in the tip part, an observing means having a visual field for observing an object to be imaged by receiving a light from the object entering through said observing window, an illuminating light output means for emitting an illuminating light through said illuminating window and a hollow channel formed within said insertable part and including an opening formed in said tip part, at least the tip part of said insertable part being formed of a non-ferromagnetic characteristic material; and an NMR metering probe having a signal transmitting member inserted into said body through said channel and opening, said probe being connected at one end to an NMR metering apparatus so as to transmit high frequency signals therefrom, and a loop-like antenna connected to the other end of said signal transmitting member to receive said high frequency signals, said loop-like antenna being projected out of the opening of said channel formed in said tip part to radiate said high frequency signals and generate a high frequency magnetic field such that a high frequency magnetic field is delivered to a body part by said antenna so as to cause NMR radiation from said body part, said NMR radiation being received by said antenna and delivered to said NMR metering apparatus to enable detection of a physiological variation in the body part, whereby location of the source of the radiation within said body can be visually identified by use of said observing means of said endoscope.

3. An endoscope apparatus according to claim 2 wherein said non-ferromagnetic characteristic material is at least one of a copper alloy, aluminum alloy, austenitic stainless steel and synthetic resin.

4. An endoscope apparatus according to claim 1 or 2 wherein said endoscope has formed in the tip part of the insertable part a containing part to contain said loop-like antenna.

5. An endoscope apparatus according to claim 4 wherein said antenna is in the form of a circular annulus having an outside diameter smaller than the outside diameter of the tip part of the insertable part of said endoscope and said containing part is a circular annular groove formed in said tip part in which said circular annular antenna is contained.

6. An endoscope apparatus according to claim 4 wherein said antenna is in a form of a semi-cylindrical saddle parallel with the axial direction of the tip part of the insertable part of said endoscope and said containing part is a semi-cylindrical groove part in which said saddle like antenna is contained.

7. An endoscope apparatus according to claim 1 or 2 wherein the loop in said antenna is in a plane substantially perpendicular to the axial direction of said signal transmitting member.

8. An endoscope apparatus according to claim 1 or 2 wherein the loop in said antenna is in a plane substantially parallel with the axial direction of said signal transmitting member.

9. An endoscope apparatus according to claim 1 or 2 wherein said antenna is so arranged that the center axis of the loop may be placed substantially parallel with the optical axis of said observing means within the visual field of said observing means at least at the time of metering NMR.

10. An endoscope apparatus according to claim 1 or 2 wherein said NMR metering probe is further provided with an expansible balloon to be projected out of an opening of said channel and said antenna is formed of wire embedded in said balloon.

11. An endoscope apparatus according to claim 1 or 2 wherein said NMR metering probe is further provided with a sucking path opening near said antenna projected out of the opening of said channel.

12. An endoscope apparatus according to claim 1 or 2 wherein said endoscope is further provided with a sucking path opening near said antenna projecting out of the opening of said channel.

13. An endoscope apparatus according to claim 1 or 2 wherein said NMR metering probe is provided with a first pipe line which can be projected out of the opening of said channel to become loop-like when filled at least with a fluid, a second pipe line inserted through said channel and feeding a fluid to said first pipe line and a conductive fluid with which said first and second pipe lines can be filled, said first pipe line becoming said antenna part when it is filled with said conductive fluid and said second pipe line becoming said signal transmitting member when it is filled with said conductive fluid.

14. An endoscope apparatus according to claim 13 wherein said conductive fluid is at least one of a conductive liquid, conductive gas, conductive powder, conductive gel and mixture of at least two of them.

15. An endoscope apparatus according to claim 1 or 2 wherein said NMR metering probe is further provided with a means for changing the direction of orientation of said antenna.

16. An endoscope apparatus according to claim 15 wherein said antenna is bendable and said means for changing the direction of said antenna has an angle changing means for changing the angle of said antenna part made with respect to the axial direction of said signal transmitting member.

17. An endoscope apparatus according to claim 15 wherein said means of changing the direction of said antenna has a rotating means rotating said antenna.

18. An endoscope apparatus according to claim 1 or 2 where said antenna is spirally wound and has resiliency in the axial direction of this spiral.

19. An endoscope apparatus according to claim 1 or 2 wherein said NMR metering probe has a tubular member to which at least a part of said signal transmitting member and said antenna are fitted.

20. An endoscope apparatus according to claim 1 or 2 wherein said NMR metering probe is provided with a retained tube having a tubular member to which at least a part of said signal transmitting member and said antenna are fitted and a flap made by projecting a part of the outer peripheral part of said tubular member outside in the radial direction.

21. An endoscope apparatus according to claim 20 wherein said antenna is formed by printing on a flexible printed substrate on the outer peripheral surface of said tubular member.

22. An endoscope apparatus according to claim 1 or 2 wherein said NMR metering probe is further provided with a spacer interposed between said antenna and an object to be examined, forming a predetermined gap between said antenna and said object to be examined and contacting said object.

23. An endoscope apparatus according to claim 1 or 2 wherein said observing means has an image forming optical system provided in the tip part of said insertable part, an eyepiece part provided on the rear end of said insertable part and an image transmitting optical system for transmitting to said eyepiece part an object image formed by said image forming optical system.

24. An endoscope apparatus according to claim 1 or 2 wherein said observing means has an image forming optical system provided in the tip part of said insertable part and an imaging means for imaging an object image formed by said image forming optical system.

25. An NMR metering endoscope system comprising:
an endoscope having an elongate insertable part having a tip part and an observing window and an illuminating window in the tip part, an observing means for observing an object to be imaged by receiving a light from the object entering through said observing window, an illuminating light output means for emitting an illuminating light through said illuminating window and a hollow channel formed within said insertable part including an opening in said tip part;
a static magnetic field generating means for creating a static magnetic field in an object to be metered;
an NMR metering apparatus having a high frequency generating means for outputting a high frequency corresponding to a radiating frequency of the object to be metered and a detecting means for detecting an NMR signal from the object corresponding to the high frequency output from said high frequency generating means; and
an NMR metering probe having a signal transmitting member inserted through said channel, said signal transmitting member being connected at one end to said NMR metering apparatus so as to transmit high frequency signals therefrom, and a loop-like antenna connected to the other end of said signal transmitting member to receive said high frequency signals, said loop-like antenna being projected out of the opening of said channel to radiate said high frequency signals and generate a high frequency magnetic field such that a high frequency magnetic field is delivered to said object by said antenna so as to cause NMR radiation from said object, said radiation being received by said antenna and delivered to said NMR metering apparatus to enable detection of physiological variation in the object, whereby location of the source of the radiation can be visually identified by use of said observing means of said endoscope.

26. An NMR metering endoscope system comprising:
an endoscope having an elongate insertable part having a tip part insertable into a body and an observing window and an illuminating window in the tip part, an observing means for observing an object to be imaged by receiving a light from the object entering through said observing window, an illuminating light output means for emitting an illuminating light through said illuminating window and a hollow channel formed within said insertable part and opening in said tip part, at least the tip part of said insertable part being formed of a non-ferromagnetic characteristic material;
a static magnetic field generating means for creating a static magnetic field in an object to be metered;
an NMR metering apparatus having a high frequency generating means for outputting a high frequency corresponding to a radiating frequency of the object to be metered and detecting means for detecting an NMR signal from the object corresponding to the high frequency output from said high frequency generating means; and
an NMR metering probe having a signal transmitting member inserted through said channel, said signal transmitting member being connected at one end to said NMR metering apparatus so as to transmit high frequency signals therefrom, and a loop-like antenna connected to the other end of said signal transmitting member to receive said high frequency signals, said loop-like antenna being projected out of the opening of said channel to radiate said high frequency signals and generate a high frequency magnetic field such that a high frequency magnetic field is delivered to a body part by said antenna so as to cause NMR radiation from said body part, said radiation being received by said antenna and delivered to said NMR metering apparatus to enable detection of physiological variation in the body part, whereby location of the source of the radiation can be visually identified by use of said observing means of said endoscope.

* * * * *